US008633155B2

(12) United States Patent
Gerber et al.

(10) Patent No.: US 8,633,155 B2
(45) Date of Patent: Jan. 21, 2014

(54) METHODS OF USING ANGIOPOIETIN-LIKE 4 PROTEIN TO STIMULATE PROLIFERATION OF PRE-ADIPOCYTES

(75) Inventors: Hanspeter Gerber, San Francisco, CA (US); Stuart Bunting, Half Moon Bay, CA (US); Xiao Huan Liang, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 264 days.

(21) Appl. No.: 12/573,832

(22) Filed: Oct. 5, 2009

(65) Prior Publication Data
US 2010/0172915 A1   Jul. 8, 2010

Related U.S. Application Data

(63) Continuation of application No. 11/540,430, filed on Sep. 28, 2006, now abandoned, which is a continuation of application No. 11/185,204, filed on Jul. 19, 2005, now Pat. No. 7,371,384.

(60) Provisional application No. 60/589,875, filed on Jul. 20, 2004.

(51) Int. Cl.
*A61K 38/16* (2006.01)
(52) U.S. Cl.
USPC ............................ 514/4.8; 514/13.3; 530/350
(58) Field of Classification Search
None
See application file for complete search history.

(56) References Cited

U.S. PATENT DOCUMENTS

| 5,227,158 | A  | 7/1993  | Jardieu       |
| 6,348,350 | B1 | 2/2002  | Goddard et al. |
| 6,372,491 | B1 | 4/2002  | Goddard et al. |
| 6,455,496 | B1 | 9/2002  | Goddard et al. |
| 6,475,753 | B1 | 11/2002 | Ruben et al.  |
| 6,627,741 | B2 | 9/2003  | Brewer et al. |
| 6,673,454 | B1 | 1/2004  | Tsuda et al.  |
| 6,673,545 | B2 | 1/2004  | Faris et al.  |
| 2002/0119463 | A1 | 8/2002  | Faris et al.  |
| 2003/0065151 | A1 | 4/2003  | Ruben et al.  |
| 2003/0099994 | A1 | 5/2003  | Holtzman et al. |
| 2003/0199058 | A1 | 10/2003 | Baker et al.  |
| 2003/0207348 | A1 | 11/2003 | Shimkets et al. |
| 2003/0207350 | A1 | 11/2003 | Baker et al.  |
| 2003/0207351 | A1 | 11/2003 | Baker et al.  |
| 2003/0207352 | A1 | 11/2003 | Baker et al.  |
| 2003/0207353 | A1 | 11/2003 | Baker et al.  |
| 2003/0207356 | A1 | 11/2003 | Baker et al.  |
| 2003/0207357 | A1 | 11/2003 | Baker et al.  |
| 2003/0207359 | A1 | 11/2003 | Baker et al.  |
| 2003/0207360 | A1 | 11/2003 | Baker et al.  |
| 2003/0207371 | A1 | 11/2003 | Baker et al.  |
| 2003/0207374 | A1 | 11/2003 | Baker et al.  |
| 2003/0207375 | A1 | 11/2003 | Baker et al.  |
| 2003/0207376 | A1 | 11/2003 | Baker et al.  |
| 2003/0207389 | A1 | 11/2003 | Baker et al.  |
| 2003/0207422 | A1 | 11/2003 | Baker et al.  |
| 2003/0207423 | A1 | 11/2003 | Baker et al.  |
| 2003/0207424 | A1 | 11/2003 | Baker et al.  |
| 2003/0207425 | A1 | 11/2003 | Baker et al.  |
| 2003/0207426 | A1 | 11/2003 | Baker et al.  |
| 2003/0207427 | A1 | 11/2003 | Baker et al.  |
| 2003/0208055 | A1 | 11/2003 | Baker et al.  |
| 2003/0215451 | A1 | 11/2003 | Ferrara et al. |
| 2003/0219885 | A1 | 11/2003 | Baker et al.  |
| 2004/0249141 | A1 | 12/2004 | Goddard et al. |
| 2005/0123925 | A1 | 6/2005  | Ashkenazi et al. |
| 2005/0233361 | A1 | 10/2005 | Clerc et al.  |
| 2005/0239706 | A1 | 10/2005 | Backhed et al. |
| 2006/0093607 | A1 | 5/2006  | Gerber et al. |
| 2006/0222645 | A1 | 10/2006 | Lee et al.    |
| 2007/0026002 | A1 | 2/2007  | Gerber et al. |

FOREIGN PATENT DOCUMENTS

| CN | 1315451       |   | 10/2001 |
| CN | 1343725       | * | 4/2002  |
| EP | 1 403 367 A1  |   | 3/2004  |
| JP | 2000-308488   |   | 11/2000 |
| WO | WO 99/32515   |   | 7/1999  |
| WO | WO 99/45135   |   | 9/1999  |
| WO | WO 99/66041   |   | 12/1999 |
| WO | WO 99/67382   |   | 12/1999 |
| WO | WO 9967382 A2 | * | 12/1999 |
| WO | WO 00/52165   |   | 9/2000  |
| WO | WO 00/61629   |   | 10/2000 |
| WO | WO 00/63380   |   | 10/2000 |
| WO | WO 01/02429 A2 |  | 1/2001  |
| WO | WO 01/05825 A2 |  | 1/2001  |
| WO | WO 01/05971 A2 |  | 1/2001  |

(Continued)

OTHER PUBLICATIONS

Pinkerton et al., Angiopoietin-like 4 exacerbates collagen-induced arthritis and increases the phosphorylation of Akt in mouse endothelial cells, FASEB J. 18(4-5):abstr.778.12, Apr. 2004.*
Accession No. NM_020581.1; Accession was first seen at NCBI on Sep. 18, 2000.
Accession No. NM_139314.1; Accession was first seen at NCBI on Jun. 21, 2002.
Accession No. Q9BY76; Accession was first seen at NCBI on Nov. 15, 2002.
Accession No. Q9Z1P8; Accession was first seen at NCBI on Nov. 15, 2002.
Ajioka, et al., "Expression of vascular endothelial growth factor promotes colonization, vascularization and growth of transplanted hepatic tissues in the mouse", Hepatology, 29:396-402, (1999).

(Continued)

*Primary Examiner* — Claire Kaufman
(74) *Attorney, Agent, or Firm* — Grant Kalinowski; Jeffery P. Bernhardt; Arnold & Porter LLP

(57) ABSTRACT

ANGPTL4 compositions and methods of using such compositions, and agonists or antagonists thereof, for the diagnosis and treatment of diseases or disorders are included, including methods to modulate cell proliferation, cell adhesion, and cell migration.

4 Claims, 14 Drawing Sheets

(56) References Cited

FOREIGN PATENT DOCUMENTS

| | | |
|---|---|---|
| WO | WO 01/53455 A2 | 7/2001 |
| WO | WO 01/53486 | 7/2001 |
| WO | WO 01/54477 A2 | 8/2001 |
| WO | WO 01/57188 A2 | 8/2001 |
| WO | WO 01/77151 A2 | 10/2001 |
| WO | WO 02/077013 A2 | 10/2002 |
| WO | WO 02/101039 A1 | 12/2002 |
| WO | WO 03/000865 A2 | 1/2003 |
| WO | WO 03/010205 | 2/2003 |
| WO | WO 03/025138 A2 | 3/2003 |
| WO | WO 03/040329 A2 | 5/2003 |
| WO | WO 03/040330 A2 | 5/2003 |
| WO | WO 03/048185 A2 | 6/2003 |
| WO | WO 03/060071 A2 | 7/2003 |
| WO | WO 03/103581 A2 | 12/2003 |
| WO | WO 2006/014678 A3 | 2/2006 |
| WO | WO 2006/014729 A2 | 2/2006 |

OTHER PUBLICATIONS

Akiyama, et al., "Conditional disruption of the peroxisome proliferator-activated receptor gamma gene in mice results in lowered expression of ABCA1, ABCG1 and apoE in macrophages and reduced cholesterol efflux", Molecular & Cellular Biology, 22(8):2607-2619, (2002).

Assy, et al., "Effect of vascular endothelial growth factor on hepatic regenerative activity following partial hepatectomy in rats", Journal of Hepatology, 30:911-915, (1999).

Baruch, et al., "Basic fibroblast growth factor is hapatotropic for rat liver in regeneration", J. Hepatol., 23:328-332, (1992).

Bouloumie, et al., "Leptin, the product of Ob gene, promotes angiogenesis", Circ Res., 83(10):1059-1066, (1998).

Camenisch, et al., "ANGPTL3 stimulates endothelial cell adhesion and migration via integrin alpha vbeta 3 and induces blood vessel formation in vivo", J. Bio. Chem., 277(19):17281-17290, (2002).

Campfield, et al., "Recombinant mouse ob protein: evidence for a peripheral signal linking adiposity and central neural networks", Science, 269:546-549, (1995).

Chehab, et al., "Correction of the sterility defect in homozygous obese female mice by treatment with the human recombinant leptin", Nat. Genet., 12(3):318-320, (1996).

Chen, et al., "Evidence that the diabetes gene encodes the leptin receptor: identification of a mutation in the leptin receptor gene in db/db mice", Cell, 84:491-495. (1996).

Cioffi, et al., "Novel B219/OB receptor isoforms: possible role of leptin in hematopoiesis and reproduction", Nature Medicine, 2(5):585-589, (1996).

Clement, et al.. "A mutation in the human leptin receptor gene causes obesity and pituitary dysfunction", Nature, 392(6674):398-401, (1998).

Desai, et al.. "Lipid-lowering effects of anti-angiopoietin-like 4 antibody recapitulate the lipid phenotype found in angiopoietin-like 4 knockout mice", PNAS, 104(28):11766-11771, (2007).

Drakes, et al.. "In vivo administration of flt3 ligand markedly stimulates generation of dendritic cell progenitors from mouse liver", J. Immunol., 159:4268-4278, (1997).

Eliceiri, et al., "Adhesion events in angiogenesis", Cum Opin. Cell Biol., 13(5):563-568, (2001).

Eliceiri, et al., "The role of alphav integrins during angiogenesis", Mol. Med., 4(12):741-750, (1998).

Eliceriri, et al., "The role of alphaV integrins during angiogenesis: insights into potential mechanisms of action and clinical development", J. Clin. Invest., 10399):1227-1230, (1999).

Ferrara, et al., "Clinical applications of angiogenic growth factors and their inhibitors", Nat. Med., 5(12):1359-1364, (1999).

Folkman, et al., "Blood vessel formation: what is its molecular basis?", Cell, 87(7):1153-1155, (1996).

Folkman, et al., "Angiogenic factors", Science, 235:442-447, (1987).

Friedlander, et al., "Definition of two angiogenic pathways by distinct alpha v integrins", Science, 270(5241):1500-1502, (1995).

Fujiwara, et al., "Stimulation of liver growth by exogenous human hepatocyte growth factor in normal and partially hepatectomized rats", Hepatol., 18:1443-1449, (1993).

Fukumura, et al., "Paracrine regulation of angiogenesis and adipocyte differentiation during in vivo adiopogenesis", Circ. Res., 93(9):e88-e97, (2003).

Gainsford, et al., "Leptin can induce proliferation, differentiation and functional activation of hemopoietic cells", PNAS, 93:14564-14568, (1996).

Gbaguidi, et al., "Peroxisome proliferator-activated receptor (PPAR) agonists decrease lipoprotein lipase secretion and glycated LDL uptake by human macrophages", FEBS Letters. 512(1-3):85-90, (2002).

Ge, et al., "Differential regulation and properties of angiopoietin-like proteins 3 and 4", J. Lipid. Res., 46(7):1484-1490, (2005).

Ge, et al., "Oligomerization and regulated proteolytic processing of angiopoietin-like protein 4", J. Biol. Chem., 279(3):2038-2045, (2004).

Ge, et al.. "Oligomerization state-dependent hyperlipidemic effect of angiopoietin-like protein 4", J. Lipid Res., 45(11):2071-2079, (2004).

Ge, et al., "Oligomerization and regulated proteolytic processing of angiopoietin-like protein 4", Diabetes, 53(Suppl.2):A576, (2004).

Gerber, et al., "VEGF is required for growth and survival in neonatal mice", Development, 126:1149-1159, (1999).

Goldspiel, et al., "Human gene therapy" Clinical Pharm., 12(7):488-505, (1993).

Gong, et al., "New progress in adipocytokine research", Current Opinion in Endocrinology and Diabetes, 10(2):115-121, (2003).

Gregoire, et al., "Understanding adipocyte differentiation", Physiol. Rev., 78(3):783-809, (1998).

Halaas, et al., "Weight-reducing effects of the plasma protein encoded by the obese gene", Science, 269:543-546, (1995).

Hermann, et al., "Angiopoietin-like-4 is a potential angiogenic mediator in arthritis", Clinical Immunol., 115(1):93-101, (2005).

Hesser, et al., "Down syndrome critical region protein 1 (DSCR1), a novel VEGF target gene that regulates expression of inflammatory markers on activated endothelial cells", Blood, 104(1):149-158, (2004).

Inukai, et al., "ANGPTL3 is increased in both insulin-deficient and resistant diabetic states", Biochemical and Biophysical Research Communications, 317:1075-1079, (2004).

Ito, et al., "Heparin-binding EGF0like growth factor is a potent mitogen for rat hepatocytes", Biochem. & Bioiphy. Res. Comm., 198:25-31, (1994).

Ito, et al., "Inhibition of angiogenesis and vascular leakiness by angiopoietin-related protein 4", Cancer Research, 63(20):6651-6657, (2003).

Kamohara, et al., "Acute stimulation of glucose metabolism in mice by leptin treatment", Nature, 389(6649):374-377, (1997).

Kersten, et al., "Characterization of the fasting-induced adipose factor F1AF, a novel peroxisome proliferator-activated receptor target gene", J. Biol. Chem., 275(37):28488-28493, (2000).

Kim, et al., "ADD1/SREBP1 promotes adipocyte differentiation and gene expression linked to fatty acid metabolism", Genes & Development, 10:1096-1107, (1996).

Kim, et al., "Hepatic expression, synthesis and secretion of a novel fibrinogen/angiopoietin-related protein that prevents endothelial-cell apoptosis", Biochemical Journal, 346(Pt 3):603-610, (2000).

Kimura, et al., "Stimulation of DNA synthesis and proliferation by prostaglandins in primary cultures of adult rat hepatocytes", European Journal of Pharmacology, 404(3):259-271, (2000).

Klagsbrun, et al.. "Regulators and angiogenesis", Ann. Rev. Physiol., 53:217-239, (1991).

Koishi et al., "Angptl3 regulates lipid metabolism in mice", Nat. Genet., 30(2):151-157, (2002).

Kolonin, et al., "Reversal of obesity by targeted ablation of adipose tissue", Nat. Med., 10(6):625-632, (2004).

Koster, et al., "Transgenie angiopoietin-like (angptl)4 overexpression and targeted disruption of angptl4 and angptl3: regulation of triglyceride metabolism", Endocrinology, 146(II):4943-4950, (2005).

(56) References Cited

OTHER PUBLICATIONS

Kubota, et al., "Ligand for peroxisome proliferation-activated receptor γ (troglitazone) has potent antitumor effect against human prostate cancer both in vitro and in vivo", Cancer Research, 58(15):3344-3352, (1998).
La cava, "The weight of leptin in immunity", Nat. Rev. Immunol., 4(5):371-379, (2004).
Landegren, "Measurement of cell numbers by means of the endogenous enzyme hexosaminidase. Applications to detection of lymphokines and cell surface antigens", J. Immunol. Methods, 67(2):379-388, (1984).
Le Jan, et al., "Angiopoietin-like 4 is a proangiogenic factor produced during ischemia and in conventional renal cell carcinoma", Am. J. Pathol., 162(5):1521-1528, (2003).
Lee, et al., "Abnormal splicing of the leptin receptor in diabetic mice", Nature, 379: 632-635, (1996).
Loffreda, et al., "Leptin regulates proinflammatory immune responses", FASEB J., 12(1):57-65, (1998).
Lord, et al., "Leptin modulates the T-cell immune response and reverse starvation-induced immunosuppression", Nature, 394(6696):897-901, (1998).
Maisonpierre, at al., "Angiopoietin-2, a natural antagonist for Tie2 that disrupts in vivo angiogenesis", Science, 277(5322):55-60,(1997).
Mandard, et al., "The direct peroxisome proliferator-activated receptor target fasting-induced adipose factor(FIAF/PGAR/ANGPTL4) is present in blood plasma as a truncated protein that is increased by fenofibrate treatment", J. Biol. Chem., 279(33):34411-34420, (2004).
Mandard, et al., "The fasting-induced adipose factor/angiopoietin-like protein 4 is physically associated with lipoproteins and governs plasma lipid levels and adiposity", J. biol. Chem., 281(2):934-944, (2006).
Marshall, et al., "The role of alpha v-integrins in tumor progression and metastasis", Semin. Cancer Biol., 7(3): 129-138, (1996).
Michalopoulos, at al., "Liver regeneration", Science, 276:60-65, (1997).
Millipore online catalogue, "Anti-inregrin αVβ5, clone PIF6", (2008).
Minn. et al., "Genes that mediate breast cancer metastasis to lung", Nature, 436(7050):518-524, (2005).
Mochida, et al., "Increased expression of vascular endothelial growth factor and its receptors, flt-1 and KDR/flk-1, in regenerating rat liver", Biochem.& Biophy. Res. Comm., 226:176-179, (1996).
Morgan, et al., "Human gene therapy", ann. Rev. Biochem., 62:191-217, (1993).
Mujumdar, et al., "Mechanisms of constructive vascular remodeling by homocysteine: role of PPAR", Am. J. Physiol. Cell Physiol., 282:C1009-C1015, (2002).
Nakamura, et al., "Partially purification and characterization of hepatocyte growth factor from serum of hepatectomized rats", Biochem. & Biophys. Res. Comm., 122(3):1450-1459, (1984).
Neijari, et al., "Expression, regulation and function of alphaV integrins in hepatocellular carcinoma: An vivo and in vitro study", Hepatology, 36(2):418-426, (2002).
Omori, et al., "Partial cloning of rat CD34 cDNA and expression during stem cell-dependent liver regeneration in adult rat", Hepatology, 26:720-727, (1997).
Pelleymounter, et al., "Effects of the obese gene product on body weight regulation in ob/ob mice", Science, 269:540-543, (1995).
Procopio, et al.. "Angiopoietin-1 and -2 coiled coil domains mediate distinct homo-oligomerization patterns but fibrinogen-like domains mediate ligand activity", J. Biol. Chem., 274(42):30196-30201, (1999).
Ramsay, et al.. "Hormonal regulation of postnatal chicken preadipocyte differentiation in vitro", Comparative Biochemistry and Physiology, Part B(136):245-253, (2003).
Ren, et al., "PPARgamma knockdown by engineered transcription factors: exogenous PPARgamma2 but not PPARgammal reactivates adipogenesis", Genes Dev., 16(1):27-32, (2002).

Rodgers, et al., "Histologic alterations in dermal repair after thermal injury effects of tropical Angiotensin II", J. Burn Care Rehabil., 18:381-388, (1997).
Rosen, et al., "Molecular regulation of adipogenesis", Annu. Rev. Cell Dev. Biol., 16:145-171, (2000).
Rosen, et al., "C/EBPalpha induces adiopogenesis though PPARgamma: a unified pathway", Genes Dev., 16(1): 22, (2002).
Rosen, et al., "PPAR gamma is required for the differentiation of adiopose tissue in vivo and in vitro", Mol. Cell. 494):611-617, (1999).
Rupnick, et al., "Adipose tissue mass can be regulated through the vasculature", PNAS, 99(16): 10730-10735, (2002).
Sato, "Molecular diagnosis of tumor angiogenesis and anti-angiogenic cancer therapy", Int. J. Clin. Oncol., 8(4):200-206, (2003).
Schmuth, et al., "Peroxisome proliferator-activated receptor (PPAR)-beta/delta stimulates differentiation and lipid accumulation in keratinocytes", Journal of Investigation Dermatology, 122:971-983, (2004).
Sears, et al., "Differentiation-dependent expression of the brown adipocyte uncoupling protein gene: regulation by peroxisome proliferation-activated receptor gamma", Mol. Cell Biol., 16(7):3410-3419, (1996).
Shimizugawa, et al., "ANGPTL3 decreases very low density lipoprotein triglyceride clearance by inhibition of lipoprotein lipase", The journal of Biological Chemistry, 277(37):33742-33748, (2002).
Shweiki, et al.. "Induction of vascular endothelial growth factor expression by hypoxia and by glucose deficiency in multicell spheroids: implications for tumor angiogenesis", PNAS, 92(3):768-772, (1995).
Sierra-Honigmann, et al., "Biological action of leptin as an angiogenic factor", Science, 281(5383):1683-1686, (1998).
Smith, et al., "Interaction of integrins alpha v beta 3 and glycoprotein IIb-IIIa with fibrinogen. Differential peptide recognition accounts for distinct binding sites", J. Biol. Chem., 265(21):12267-12271, (1990).
Strausberg, et al., "Generation and initial analysis of more than 15,000 full-length human and mouse cDNA sequences", PNAS, 99(26):16899-16903, (2002).
Streit, et al., "Angiogenesis, lymphangiogenesis and melanoma metastasis", Oncogene, 22(20):3172-3179. (2003).
Stroebel, et al., "A leptin missense mutation associated with hypogonadism and morbid obesity", Nat. Genet., 18:213-215, (1998).
Stupack, et al., "Get a ligand, get a life: integrins, signaling and cell survival", J. Cell Sci., 115(pt 19):3729-3738, (2002).
Suri, et al., "Requisite role of angiopoietin-1, a ligand for the TIE2 receptor, during embryonic angiogenesis", Cell, 87(7):1171-1180, (1996).
Suzuma, et al., "Vascular endothelial growth factor induces expression of connective tissue growth factor via KDR, Flt1, and phosphatidylinositol 3-kinase-akt-dependent pathways in retinal vascular cells", journal of Biological Chemistry, 275:40725-40731, (2000).
Tartaglia, et al., "Identification and expression cloning of a leptin receptor", ob-r, Cell, 83:1263-1271, (1995).
Tolstoshev, "Gene therapy, concepts, current trials and future directions", Annual review of pharmacology and taxicology, 32:573-596, (1993).
Tonini, et al., "Molecular basis of angiogenesis and cancer", Oncogene, 22(42):6549-6556, (2003).
Ward, et al., "The angiogenesis and Tie2/Tek: adding to the complexity of cardiovascular development", Semin. Cell Dev. Biol., 13(1):19-27, (2002).
Wiesner, et al., "food restriction regulates adipose-specific cytokines in pituitary gland but not in hypothalamus", J. Endocrinol., 180(3):R1-R6, (2004).
Wu, et al., "Delivery systems for gene therapy", Biotherapy, 3(1):87-95, (1991).
Wu, et al., "Transcriptional activation of adipogenesis", Curr. Opin. Cell Biol., II(6):689-694, (1999).
Xu, et al., "Angiopoietin-like protein 4 decreases blood glucose and improves glucose tolerance but induces hyperlipidemia and hepatic steatosis in mice", PNAS, 102(17):6086-6091, (2005).

(56) References Cited

OTHER PUBLICATIONS

Yamane, et al., "A new communication system between hepatocyte and sinusoidal endothelial cells in liver through vascular endothelial growth factor and Flt tyrosine kinase receptor family (Flt-1 and KDR/Flk-I)", Oncogene, 9:2683-2690, (1994).
Yang, et al., "Galactosylated alginate as a scaffold for hepatocytes entrapment", Biomaterials, 23:471-479, (2002).
Yang, et al., "Suppression of the Raf/MEK/ERK signalling cascade and inhibition of angiogenesis by carboxyl terminus of angiopoietin-like protein 4", Arteriosclerosis, Thrombosis & Vascular Biology, 28(5):835-840, (2008).
Yoon, et al., "Peroxisome proliferator-activated receptor gamma target gene encoding a novel angiopoietin-related protein associated with adipose differentiation", Mol. Cell Biol., 20(14):5343-5349, (2000).
Yoshida, et al., "Angiopoietin-like protein 4 is a potent hyperlipidemia-inducing factor in mice and inhibitor of lipoprotein lipase", J. Lipid Res., 43911):1770-1772, (2002).
Yoshimura, et al., "Expression of peroisome proliferator-activated receptors (PPARS) in human urinary bladder carcinoma and growth inhibition by its agonists", Int. J. Cancer, 104(5):597-602, (2003).
Yu, et al., "Inhibition of cardiac lipoprotein utilization by transgenic overexpression of Angptl4 in the heart", Natl. Acad. Sci., 102(5):1767-1772, (2005).
Zamecnik, et al., "Inhibition of pelication and expression of human T'Cell lyphotropic virus type III in cultured cells by exogenous synthetic oligonucleotides complementary to viral RNA", PNAS, 83:4143-4146, (1986).
Zhang, et al., "Crystal structure of the obese protein leptin-E100" Nature, 387(6629):206-209, (1997).
Zhang, et al., "Positional cloning of the mouse obese gene and its human homologue", Nature, 372:425-431, (1994).
Zhu, et al.. "Expression and function of hepatocellular carcinoma-related gene pp1158 (NCBI abstract)", 92002) ,Zhonghua Zhong Liu Za Zhi,24(2):123,Mar. 2002,abstract.
Collins, et al., "Generation and initial analysis of more than 15,000 full-length human and mouse cDNA sequences", PNAS, vol. 99, No. 26, pp. 16899-16903, (2002).
Mulligan, "The Basic Science of Gene Therapy", Science, vol. 260, pp. 926-932, (2002).
Ono, et al., "Protein region important for regulation of lipid metabolism in angiopoietin-like 3 (ANGPTL3)", The Journal of Biological Chemistry, vol. 278, No. 43, pp. 41804-41809, (2003).
Belinsky et al., "Analysis of the In Vivo Functions of Mrp3", Molecular Pharmacology, vol. 68, No. 1, pp. 160-168, (2005).
Karakashian et al., "Expression of neutral sphingomyelinase-2 (NSMase-2) in primary rat hepatocytes modulates IL-$\beta$-induced JNK activation", The FASEB Journal, vol. 1, pp. 968-970, (2004).
Kimura et al., "Stimulation of DNA synthesis and proliferation by prostaglandins in primary cultures of adult rat hepatocytes", Eur J. Pharmacol. 404, pp. 259-271, (2000).
Tien, ES. et al. "Identification of the CREB-binding protein/p300-interacting protein CITED2 as a peroxisome proliferator-activated receptor $\alpha$ coregulator", J. Biol. Chem. 279: 24053-24063, 2004.
Yoshida, K. et al. "Angiopoietin-like protein 4 is a potent hyperlipidemia-inducing factor in mice and inhibitor of lipoprotein lipase", J. Lipid Res. 43(11):1770-1772, Nov. 2002.

* cited by examiner

SEQ. ID NO:1:

```
GCCGAGCTGA GCGGATCCTC ACATGACTGT GATCCGATTC TTTCCAGCGG  50
CTTCTGCAAC CAAGCGGGTC TTACCCCCGG TCCTCCGCGT CTCCAGTCCT 100
CGCACCTGGA ACCCCAACGT CCCCGAGAGT CCCCGAATCC CCGCTCCCAG 150
GCTACCTAAG AGGATGAGCG GTGCTCCGAC GGCCGGGGCA GCCCTGATGC 200
TCTGCGCCGC CACCGCCGTG CTACTGAGCG CTCAGGGCGG ACCCGTGCAG 250
TCCAAGTCGC CGCGCTTTGC GTCCTGGGAC GAGATGAATG TCCTGGCGCA 300
CGGACTCCTG CAGCTCGGCC AGGGGCTGCG CGAACACGCG GAGCGCACCC 350
GCAGTCAGCT GAGCGCGCTG GAGCGGCGCC TGAGCGCGTG CGGGTCCGCC 400
TGTCAGGGAA CCGAGGGGTC CACCGACCTC CCGTTAGCCC CTGAGAGCCG 450
GGTGGACCCT GAGGTCCTTC ACAGCCTGCA GACACAACTC AAGGCTCAGA 500
ACAGCAGGAT CCAGCAACTC TTCCACAAGG TGGCCCAGCA GCAGCGGCAC 550
CTGGAGAAGC AGCACCTGCG AATTCAGCAT CTGCAAAGCC AGTTTGGCCT 600
CCTGGACCAC AAGCACCTAG ACCATGAGGT GGCCAAGCCT GCCCGAAGAA 650
AGAGGCTGCC CGAGATGGCC CAGCCAGTTG ACCCGGCTCA CAATGTCAGC 700
CGCCTGCACC GGCTGCCCAG GGATTGCCAG GAGCTGTTCC AGGTTGGGGA 750
GAGGCAGAGT GGACTATTTG AAATCCAGCC TCAGGGGTCT CCGCCATTTT 800
TGGTGAACTG CAAGATGACC TCAGATGGAG GCTGGACAGT AATTCAGAGG 850
CGCCACGATG GCTCAGTGGA CTTCAACCGG CCCTGGGAAG CCTACAAGGC 900
GGGGTTTGGG GATCCCCACG GCGAGTTCTG GCTGGGTCTG GAGAAGGTGC 950
ATAGCATCAC GGGGGACCGC AACAGCCGCC TGGCCGTGCA GCTGCGGGAC 1000
TGGGATGGCA ACGCCGAGTT GCTGCAGTTC TCCGTGCACC TGGGTGGCGA 1050
GGACACGGCC TATAGCCTGC AGCTCACTGC ACCCGTGGCC GGCCAGCTGG 1100
GCGCCACCAC CGTCCCACCC AGCGGCCTCT CCGTACCCTT CTCCACTTGG 1150
GACCAGGATC ACGACCTCCG CAGGGACAAG AACTGCGCCA AGAGCCTCTC 1200
```

*FIG._1A*

```
TGGAGGCTGG TGGTTTGGCA CCTGCAGCCA TTCCAACCTC AACGGCCAGT 1250

ACTTCCGCTC CATCCCACAG CAGCGGCAGA AGCTTAAGAA GGGAATCTTC 1300

TGGAAGACCT GGCGGGGCCG CTACTACCCG CTGCAGGCCA CCACCATGTT 1350

GATCCAGCCC ATGGCAGCAG AGGCAGCCTC CTAGCGTCCT GGCTGGGCCT 1400

GGTCCCAGGC CCACGAAAGA CGGTGACTCT TGGCTCTGCC CGAGGATGTG 1450

GCCGTTCCCT GCCTGGGCAG GGGCTCCAAG GAGGGGCCAT CTGGAAACTT 1500

GTGGACAGAG AAGAAGACCA CGACTGGAGA AGCCCCCTTT CTGAGTGCAG 1550

GGGGGCTGCA TGCGTTGCCT CCTGAGATCG AGGCTGCAGG ATATGCTCAG 1600

ACTCTAGAGG CGTGGACCAA GGGGCATGGA GCTTCACTCC TTGCTGGCCA 1650

GGGAGTTGGG GACTCAGAGG GACCACTTGG GGCCAGCCAG ACTGGCCTCA 1700

ATGGCGGACT CAGTCACATT GACTGACGGG GACCAGGGCT TGTGTGGGTC 1750

GAGAGCGCCC TCATGGTGCT GGTGCTGTTG TGTGTAGGTC CCCTGGGGAC 1800

ACAAGCAGGC GCCAATGGTA TCTGGGCGGA GCTCACAGAG TTCTTGGAAT 1850

AAAAGCAACC TCAGAACAC 1869
```

FIG._1B

SEQ. ID NO:2:

```
Met Ser Gly Ala Pro Thr Ala Gly Ala Ala Leu Met Leu Cys Ala
 1               5                  10                  15

Ala Thr Ala Val Leu Leu Ser Ala Gln Gly Gly Pro Val Gln Ser
                20                  25                  30

Lys Ser Pro Arg Phe Ala Ser Trp Asp Glu Met Asn Val Leu Ala
                35                  40                  45

His Gly Leu Leu Gln Leu Gly Gln Gly Leu Arg Glu His Ala Glu
                50                  55                  60

Arg Thr Arg Ser Gln Leu Ser Ala Leu Glu Arg Arg Leu Ser Ala
                65                  70                  75

Cys Gly Ser Ala Cys Gln Gly Thr Glu Gly Ser Thr Asp Leu Pro
                80                  85                  90

Leu Ala Pro Glu Ser Arg Val Asp Pro Glu Val Leu His Ser Leu
                95                  100                 105

Gln Thr Gln Leu Lys Ala Gln Asn Ser Arg Ile Gln Gln Leu Phe
                110                 115                 120

His Lys Val Ala Gln Gln Arg His Leu Glu Lys Gln His Leu
                125                 130                 135

Arg Ile Gln His Leu Gln Ser Gln Phe Gly Leu Leu Asp His Lys
                140                 145                 150

His Leu Asp His Glu Val Ala Lys Pro Ala Arg Arg Lys Arg Leu
                155                 160                 165

Pro Glu Met Ala Gln Pro Val Asp Pro Ala His Asn Val Ser Arg
                170                 175                 180

Leu His Arg Leu Pro Arg Asp Cys Gln Glu Leu Phe Gln Val Gly
                185                 190                 195

Glu Arg Gln Ser Gly Leu Phe Glu Ile Gln Pro Gln Gly Ser Pro
                200                 205                 210

Pro Phe Leu Val Asn Cys Lys Met Thr Ser Xaa Gly Gly Trp Thr
                215                 220                 225

Val Ile Gln Arg Arg His Asp Gly Ser Val Asp Phe Asn Arg Pro
                230                 235                 240
```

*FIG._2A*

```
Trp Glu Ala Tyr Lys Ala Gly Phe Gly Asp Pro His Gly Glu Phe
            245             250             255
Trp Leu Gly Leu Glu Lys Val His Ser Ile Thr Gly Asp Arg Asn
            260             265             270
Ser Arg Leu Ala Val Gln Leu Arg Asp Trp Asp Gly Asn Ala Glu
            275             280             285
Leu Leu Gln Phe Ser Val His Leu Gly Gly Glu Asp Thr Ala Tyr
            290             295             300
Ser Leu Gln Leu Thr Ala Pro Val Ala Gly Gln Leu Gly Ala Thr
            305             310             315
Thr Val Pro Pro Ser Gly Leu Ser Val Pro Phe Ser Thr Trp Asp
            320             325             330
Gln Asp His Asp Leu Arg Arg Asp Lys Asn Cys Ala Lys Ser Leu
            335             340             345
Ser Gly Gly Trp Trp Phe Gly Thr Cys Ser His Ser Asn Leu Asn
            350             355             360
Gly Gln Tyr Phe Arg Ser Ile Pro Gln Gln Arg Gln Lys Leu Lys
            365             370             375
Lys Gly Ile Phe Trp Lys Thr Trp Arg Gly Arg Tyr Tyr Pro Leu
            380             385             390
Gln Ala Thr Thr Met Leu Ile Gln Pro Met Ala Ala Glu Ala Ala
            395             400             405
Ser
406
```

FIG._2B

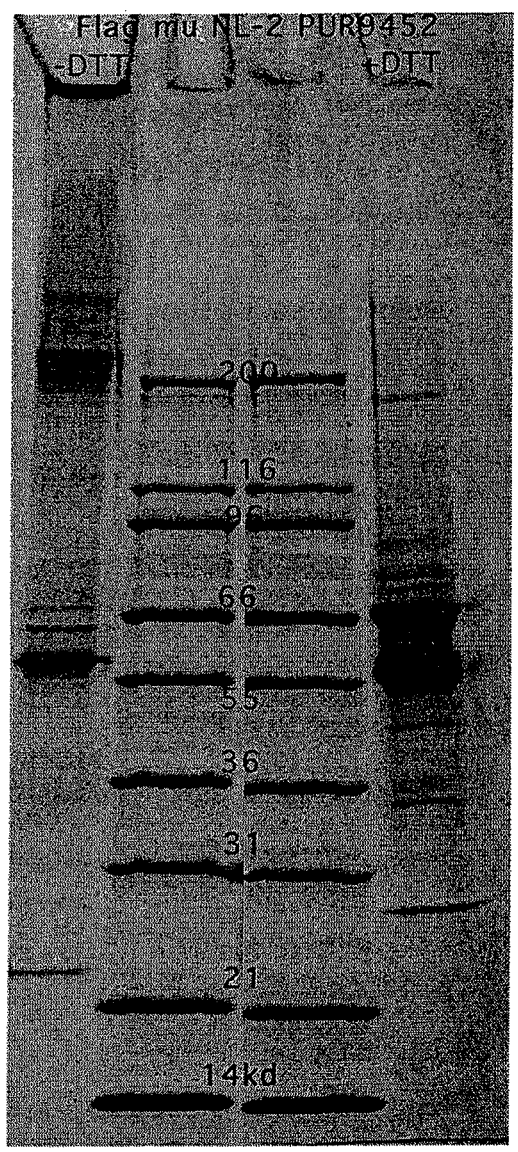
FIG._3A
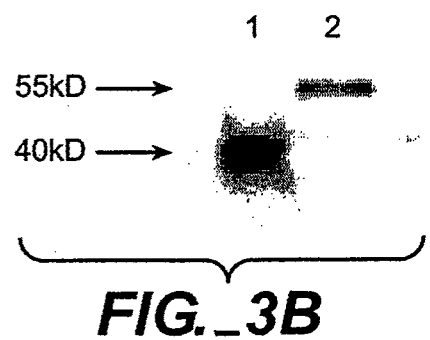
FIG._3B

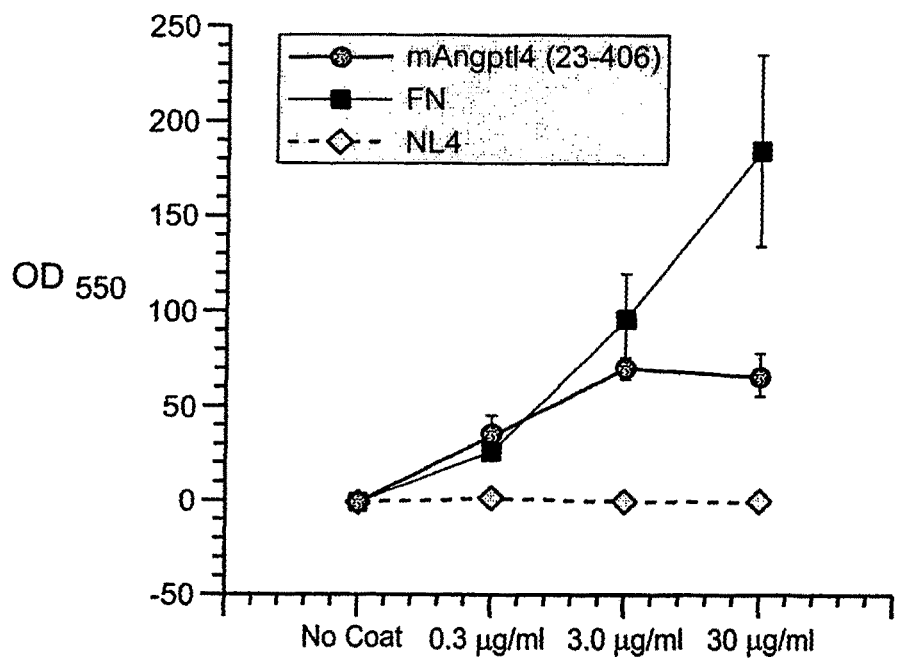
FIG._4
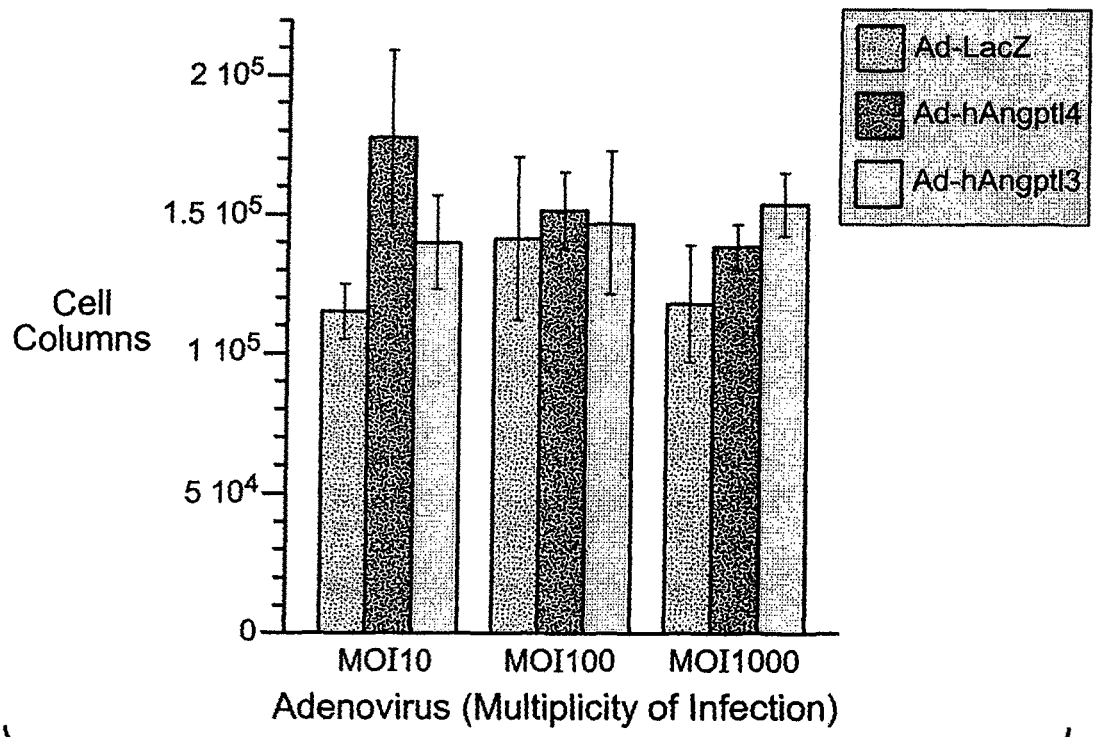
FIG._5

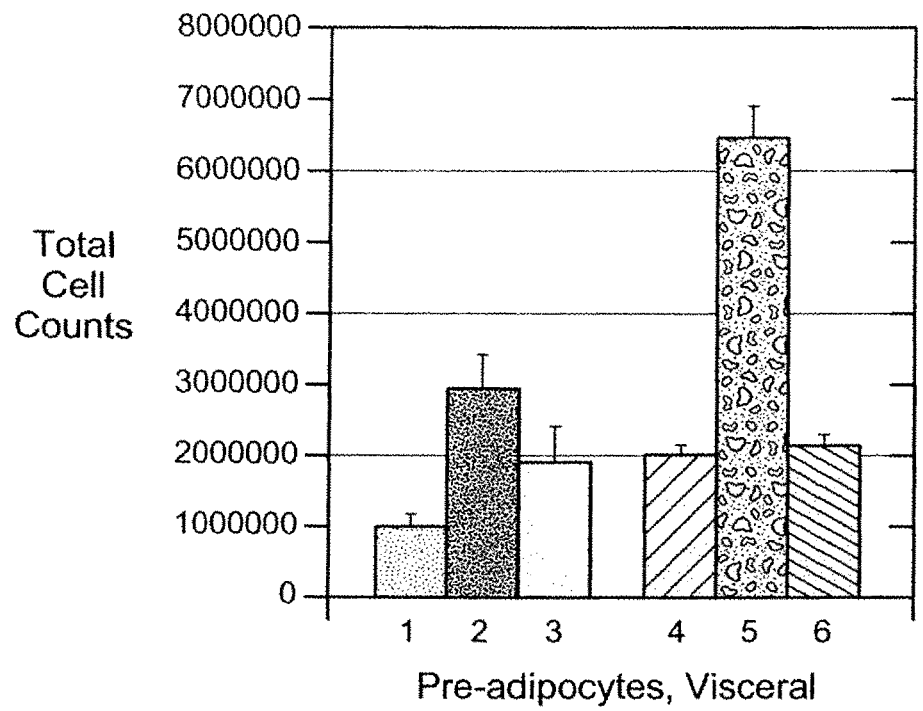
FIG._6A
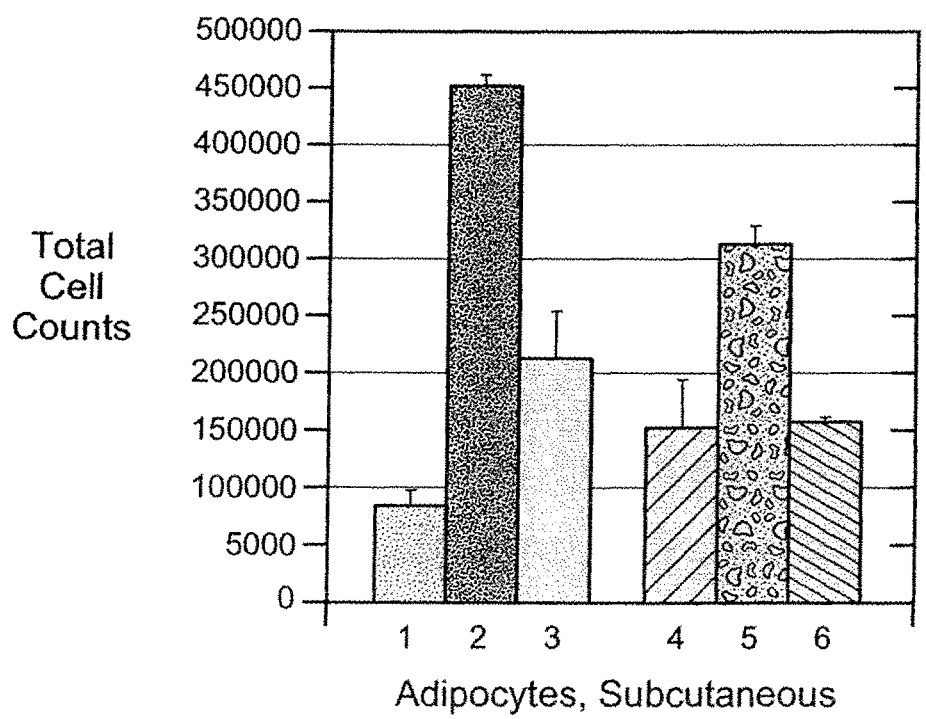
FIG._6B

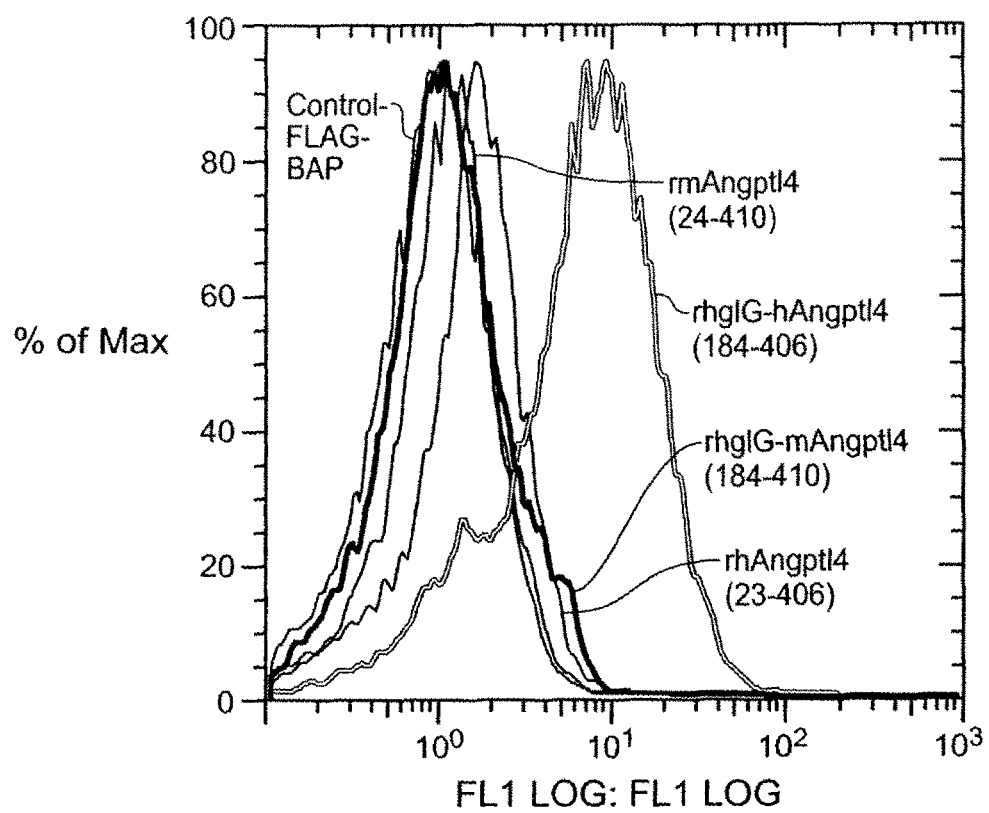
FIG. _7

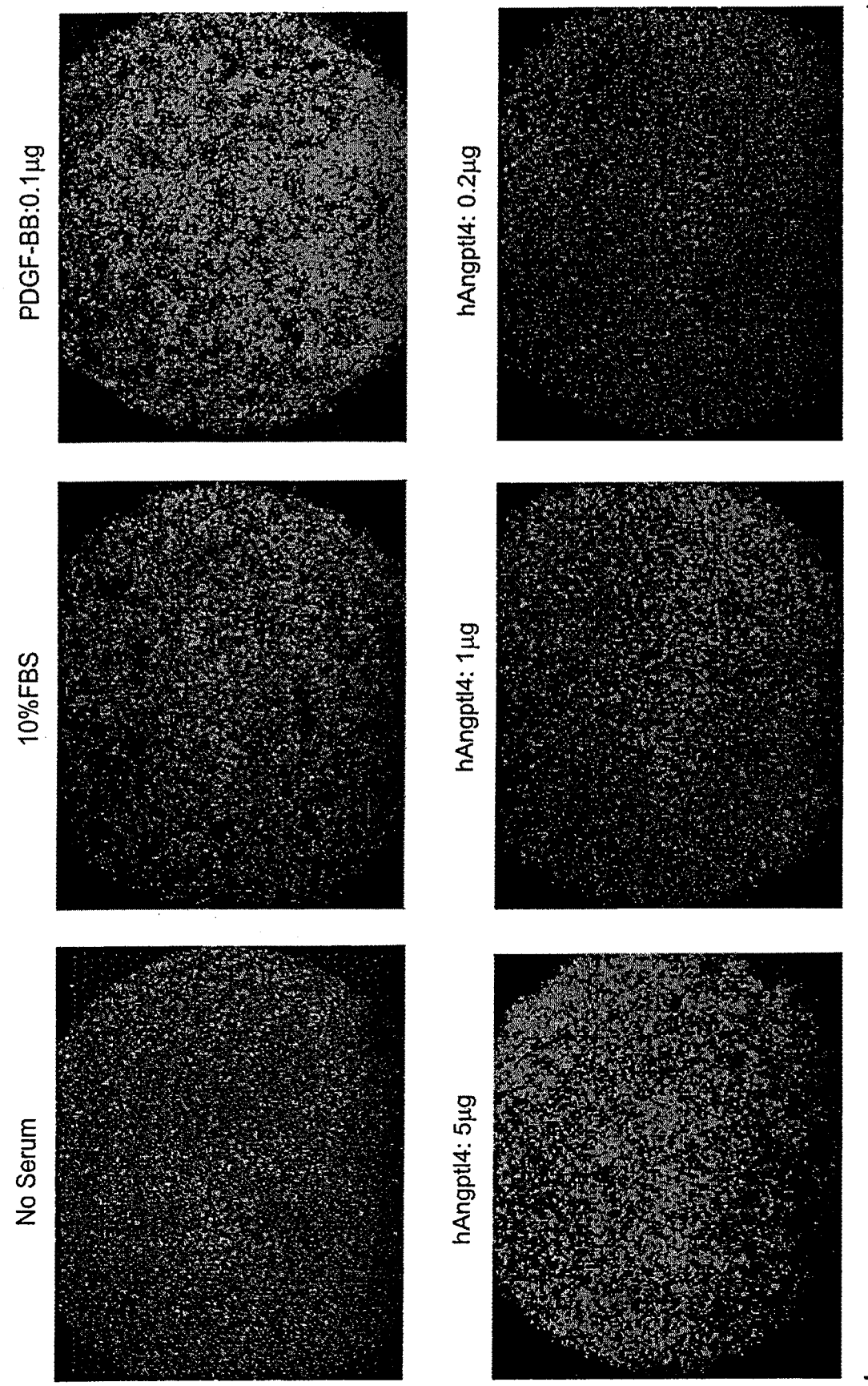

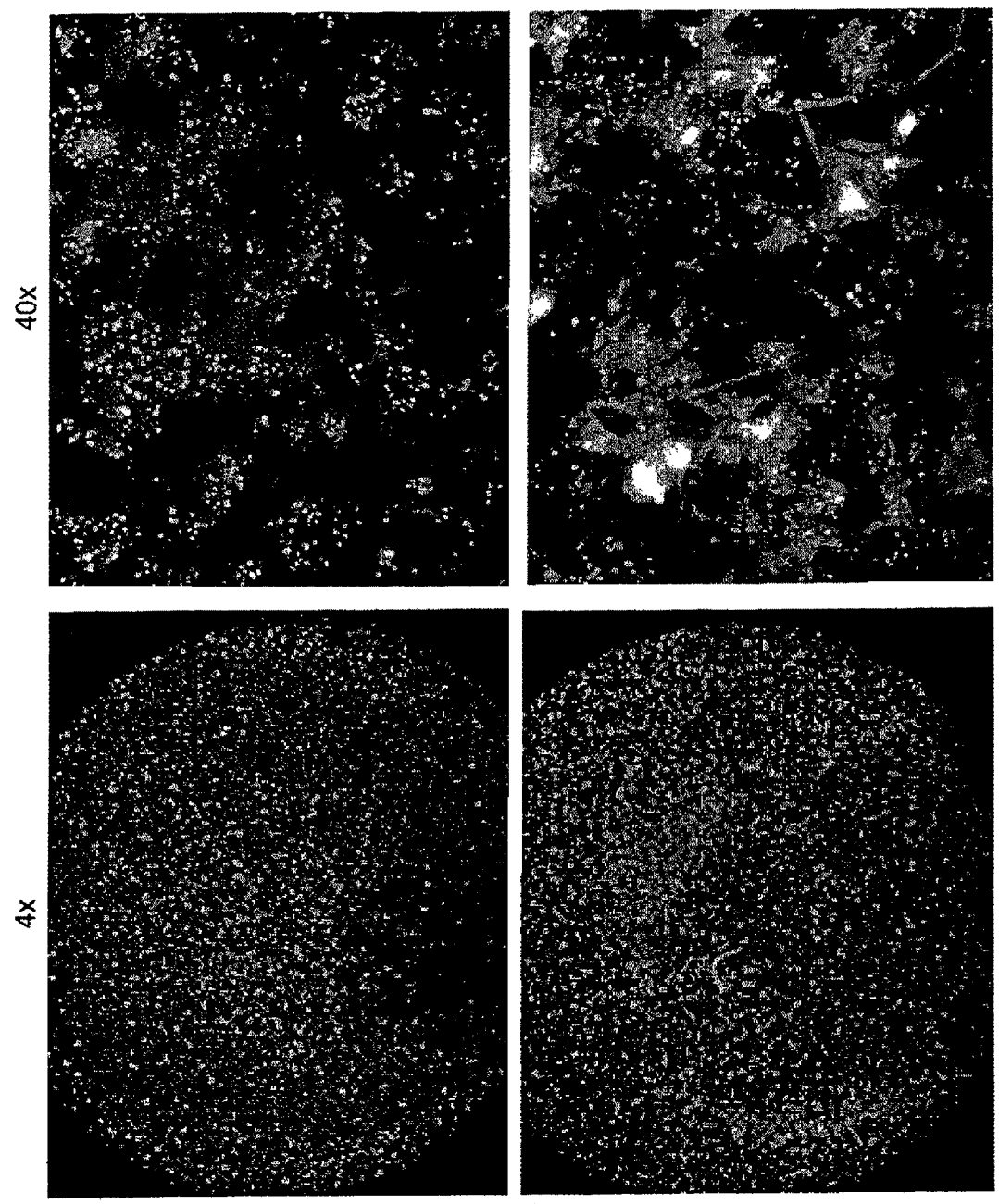
FIG._8B

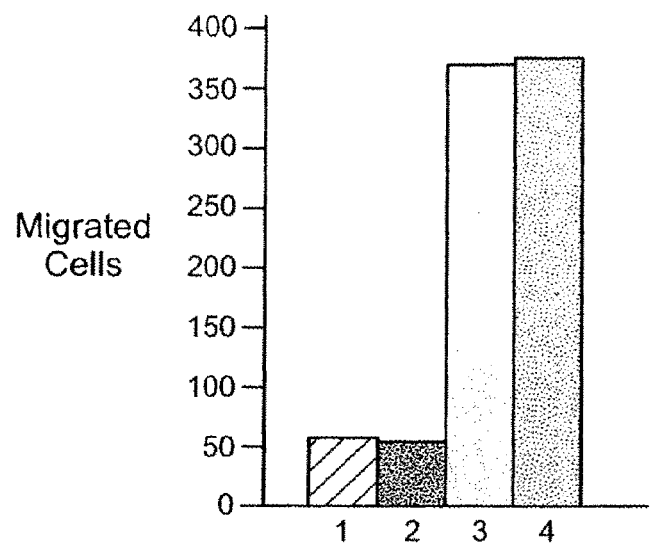
FIG._8C
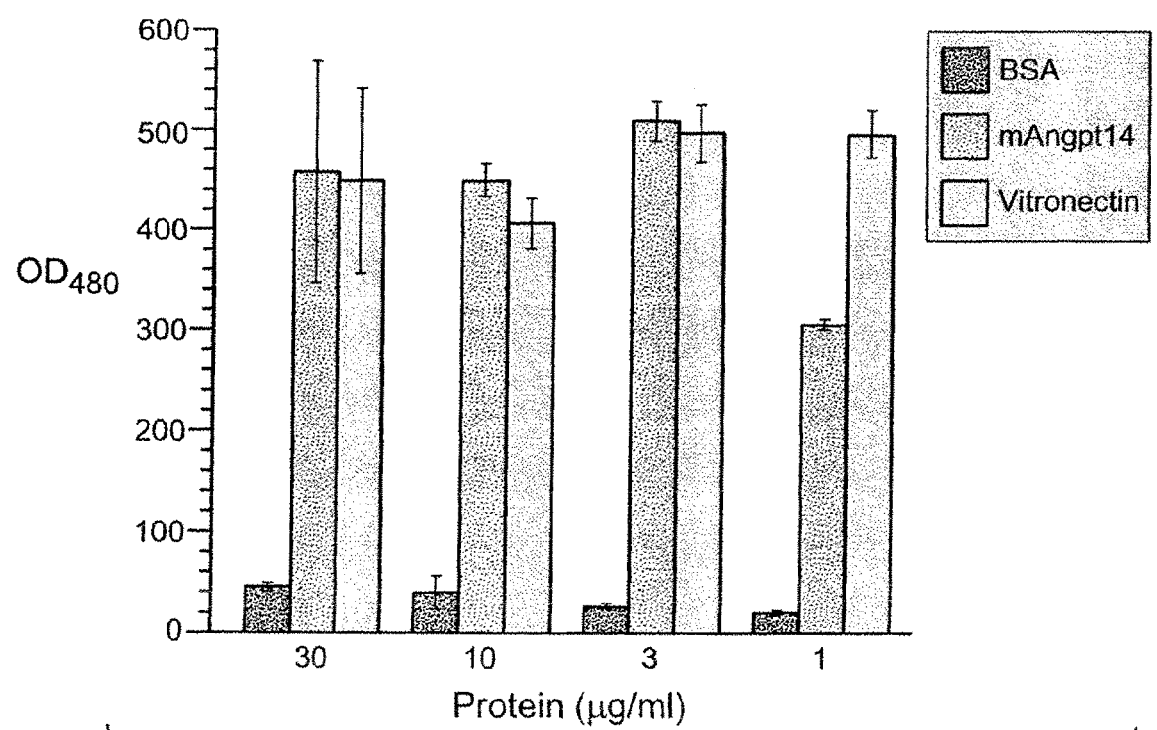
FIG._9A

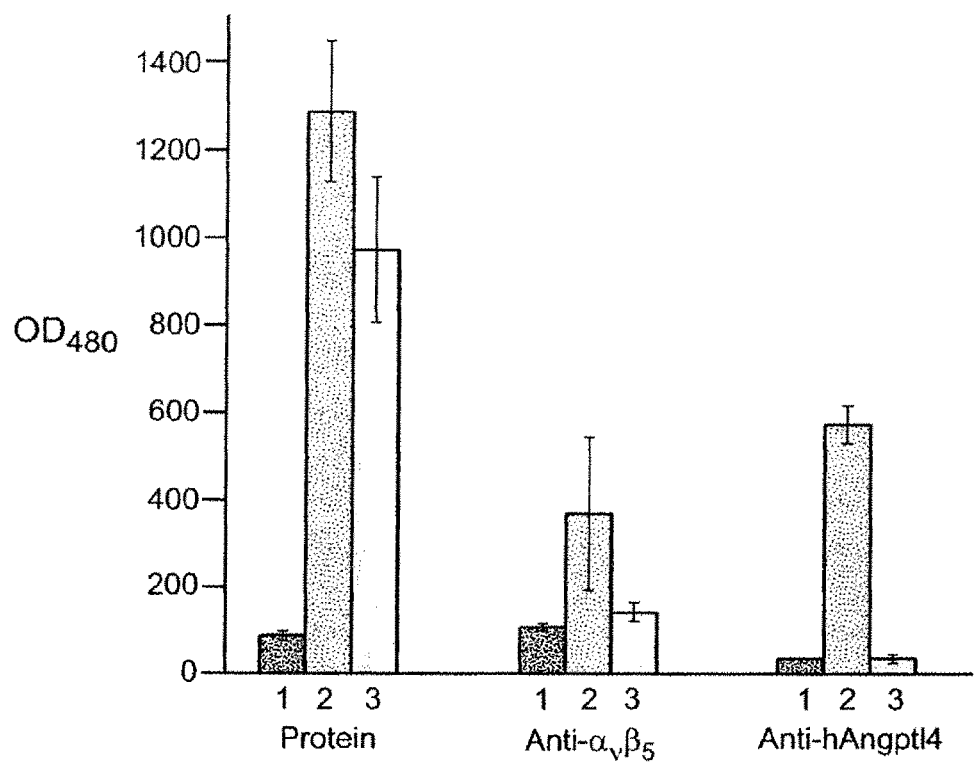
FIG._9B
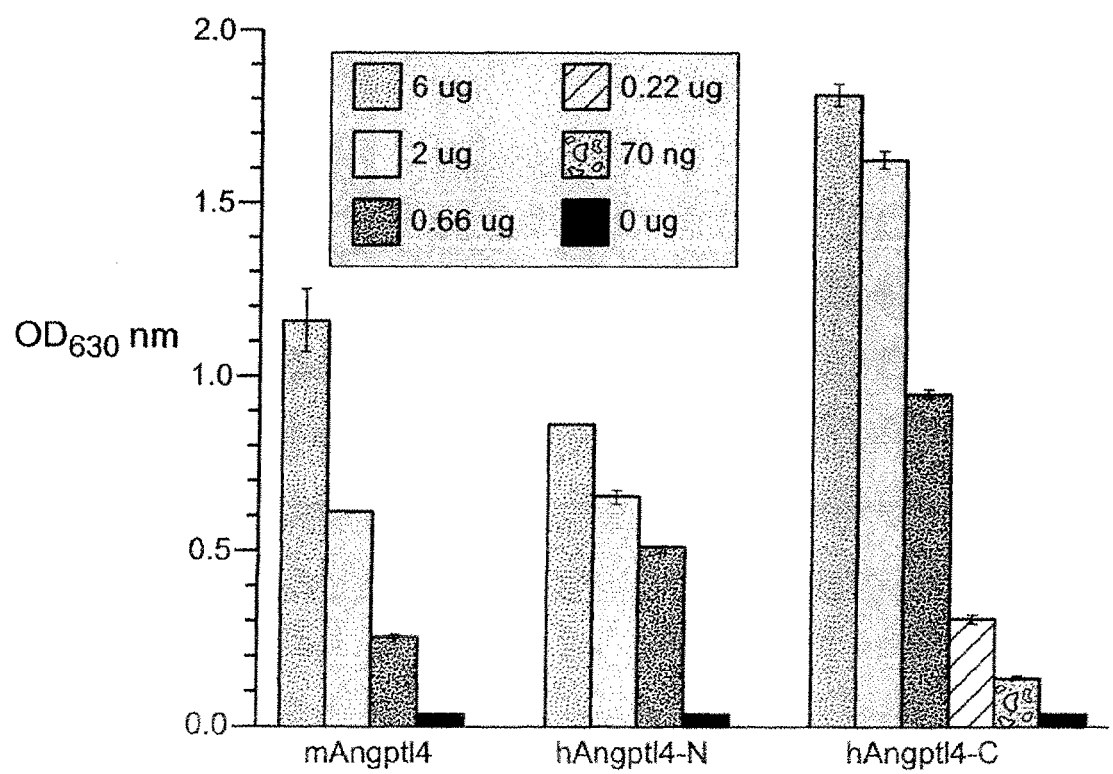
FIG._9C

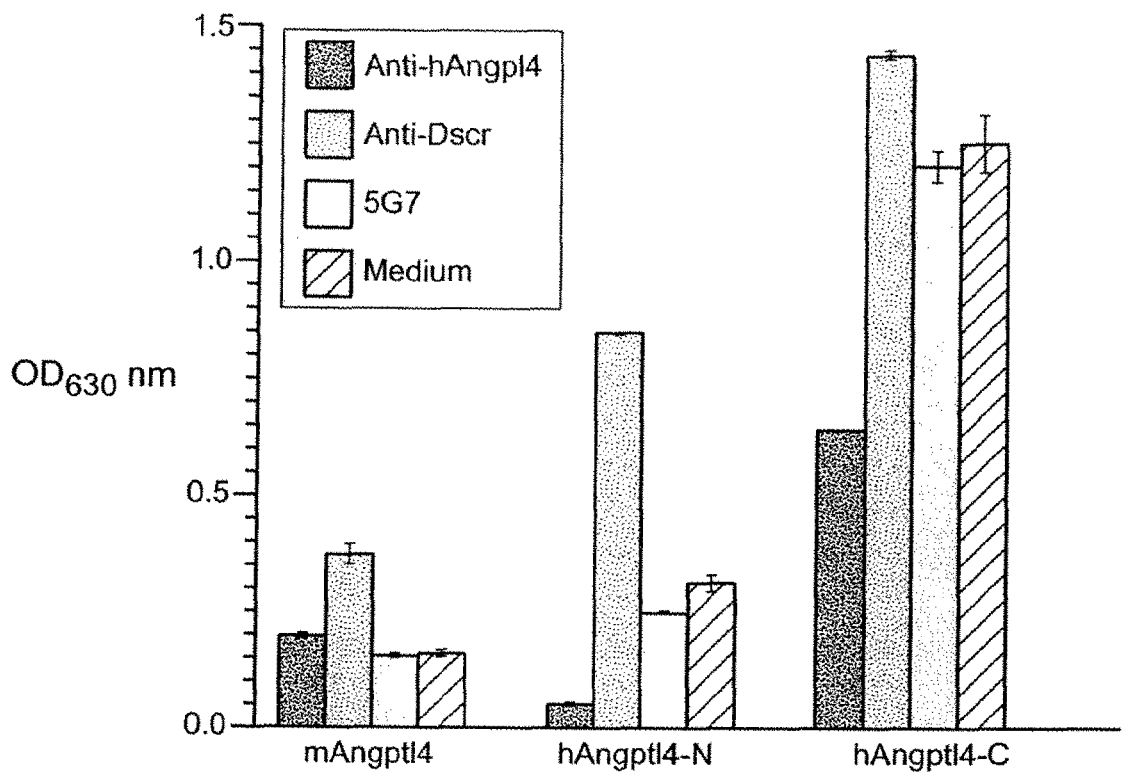
FIG._9D
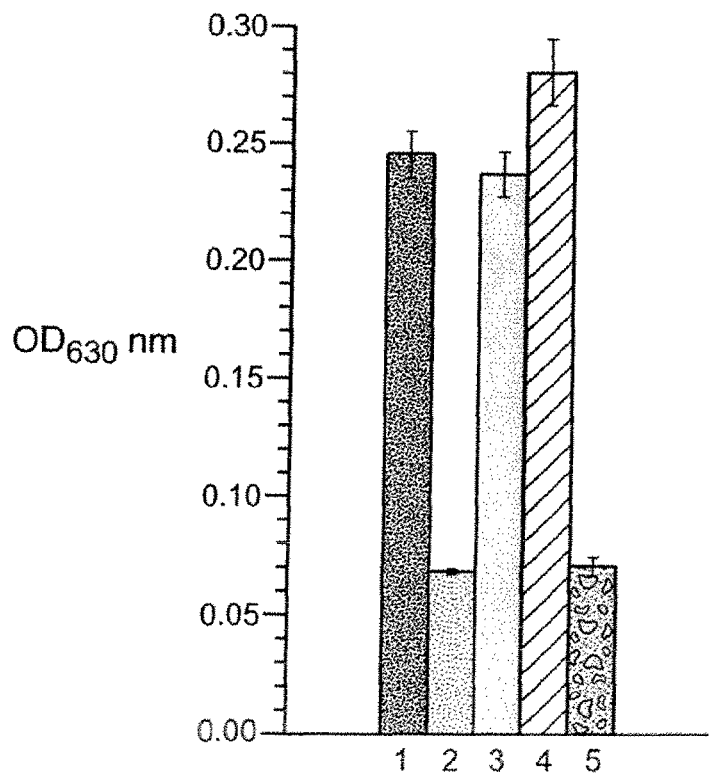
FIG._9E

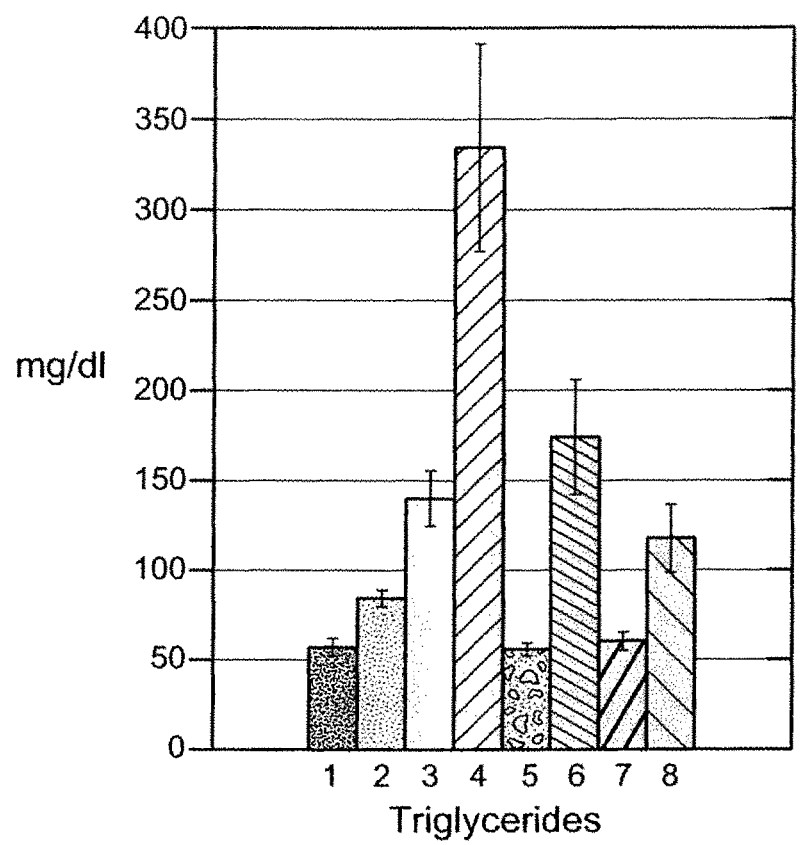
FIG._10

SEQUENCE LISTING

<160> NUMBER OF SEQ ID NOS: 30

<210> SEQ ID NO 1
<211> LENGTH: 1869
<212> TYPE: DNA
<213> ORGANISM: Homo sapiens

<400> SEQUENCE: 1

```
gccgagctga gcggatcctc acatgactgt gatccgattc tttccagcgg cttctgcaac      60
caagcgggtc ttaccccgg tcctccgcgt ctccagtcct cgcacctgga accccaacgt     120
ccccgagagt ccccgaatcc ccgctcccag gctacctaag aggatgagcg gtgctccgac     180
ggccggggca gccctgatgc tctgcgccgc caccgccgtg ctactgagcg ctcagggcgg     240
acccgtgcag tccaagtcgc cgcgctttgc gtcctgggac gagatgaatg tcctggcgca     300
cggactcctg cagctcggcc aggggctgcg cgaacacgcg gagcgcaccc gcagtcagct     360
gagcgcgctg gagcggcgcc tgagcgcgtg cgggtccgcc tgtcagggaa ccgagggtc     420 caccgacctc ccgttagccc ctgagagccg ggtggaccct gaggtccttc acagcctgca     480
gacacaactc aaggctcaga acagcaggat ccagcaactc ttccacaagg tggcccagca     540
gcagcggcac ctggagaagc agcacctgcg aattcagcat ctgcaaagcc agtttggcct     600
cctggaccac aagcacctag accatgaggt ggccaagcct gcccgaagaa agaggctgcc     660
cgagatggcc cagccagttg acccggctca caatgtcagc cgcctgcacc ggctgccag     720 ggattgccag gagctgttcc aggttgggga gaggcagagt ggactatttg aaatccagcc     780 tcagggtct ccgccatttt tggtgaactg caagatgacc tcagatggag gctggacagt     840
aattcagagg cgccacgatg gctcagtgga cttcaaccgg ccctgggaag cctacaaggc     900
ggggtttggg gatccccacg gcgagttctg gctgggtctg gagaaggtgc atagcatcac     960
gggggaccgc aacagccgcc tggccgtgca gctgcgggac tgggatggca acgccgagtt    1020
gctgcagttc tccgtgcacc tgggtggcga ggacacggcc tatagcctgc agctcactgc    1080
acccgtggcc ggccagctgg gcgccaccac cgtcccaccc agcggcctct ccgtacccct    1140
ctccacttgg gaccaggatc acgacctccg cagggacaag aactgcgcca agagcctct    1200 tggaggctgg tggtttggca cctgcagcca ttccaacctc aacggccagt acttccgctc    1260
catcccacag cagcggcaga agcttaagaa gggaatcttc tggaagacct ggcgggccg    1320 ctactacccg ctgcaggcca ccaccatgtt gatccagccc atggcagcag aggcagcctc    1380
ctagcgtcct ggctgggcct ggtcccaggc ccacgaaaga cggtgactct tggctctgcc    1440
cgaggatgtg gccgttccct gcctgggcag gggctccaag gaggggccat ctggaaactt    1500
gtggacagag aagaagacca cgactggaga agccccttt ctgagtgcag ggggctgca    1560
```

-continued

```
tgcgttgcct cctgagatcg aggctgcagg atatgctcag actctagagg cgtggaccaa    1620
ggggcatgga gcttcactcc ttgctggcca gggagttggg gactcagagg gaccacttgg    1680
ggccagccag actggcctca atggcggact cagtcacatt gactgacggg gaccagggct    1740
tgtgtgggtc gagagcgccc tcatggtgct ggtgctgttg tgtgtaggtc ccctggggac    1800
acaagcaggc gccaatggta tctgggcgga gctcacagag ttcttggaat aaaagcaacc    1860
tcagaacac                                                            1869

<210> SEQ ID NO 2
<211> LENGTH: 406
<212> TYPE: PRT
<213> ORGANISM: Homo sapiens
<220> FEATURE:
<221> NAME/KEY: MOD_RES
<222> LOCATION: (221)..(221)
<223> OTHER INFORMATION: Any amino acid

<400> SEQUENCE: 2

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
                20                  25                  30

Pro Arg Phe Ala Ser Trp Asp Glu Met Asn Val Leu Ala His Gly Leu
            35                  40                  45

Leu Gln Leu Gly Gln Gly Leu Arg Glu His Ala Glu Arg Thr Arg Ser
        50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Xaa Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
```

```
                290                 295                 300
Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
                340                 345                 350

Thr Cys Ser His Ser Asn Leu Asn Gly Gln Tyr Phe Arg Ser Ile Pro
                355                 360                 365

Gln Gln Arg Gln Lys Leu Lys Lys Gly Ile Phe Trp Lys Thr Trp Arg
                370                 375                 380

Gly Arg Tyr Tyr Pro Leu Gln Ala Thr Thr Met Leu Ile Gln Pro Met
385                 390                 395                 400

Ala Ala Glu Ala Ala Ser
                405

<210> SEQ ID NO 3
<211> LENGTH: 21
<212> TYPE: DNA
<213> ORGANISM: Homo sapiens

<400> SEQUENCE: 3
gtggccaagc ctgcccgaag a                                           21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ggccaagccu gcccgaagau u                                           21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ucuucgggca ggcuuggcca c                                           21

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ser Gly Ser
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 7

Gly Gly Gly Ser
1

<210> SEQ ID NO 8
<211> LENGTH: 384
<212> TYPE: PRT
<213> ORGANISM: Homo sapiens
<220> FEATURE:
<221> NAME/KEY: MOD_RES
<222> LOCATION: (199)..(199)
<223> OTHER INFORMATION: Any amino acid

<400> SEQUENCE: 8

Ala Gln Gly Gly Pro Val Gln Ser Lys Ser Pro Arg Phe Ala Ser Trp
1               5                   10                  15

Asp Glu Met Asn Val Leu Ala His Gly Leu Leu Gln Leu Gly Gln Gly
            20                  25                  30

Leu Arg Glu His Ala Glu Arg Thr Arg Ser Gln Leu Ser Ala Leu Glu
        35                  40                  45

Arg Arg Leu Ser Ala Cys Gly Ser Ala Cys Gln Gly Thr Glu Gly Ser
    50                  55                  60

Thr Asp Leu Pro Leu Ala Pro Glu Ser Arg Val Asp Pro Glu Val Leu
65                  70                  75                  80

His Ser Leu Gln Thr Gln Leu Lys Ala Gln Asn Ser Arg Ile Gln Gln
                85                  90                  95

Leu Phe His Lys Val Ala Gln Gln Arg His Leu Glu Lys Gln His
            100                 105                 110

Leu Arg Ile Gln His Leu Gln Ser Gln Phe Gly Leu Leu Asp His Lys
        115                 120                 125

His Leu Asp His Glu Val Ala Lys Pro Ala Arg Arg Lys Arg Leu Pro
    130                 135                 140

Glu Met Ala Gln Pro Val Asp Pro Ala His Asn Val Ser Arg Leu His
145                 150                 155                 160

Arg Leu Pro Arg Asp Cys Gln Glu Leu Phe Gln Val Gly Glu Arg Gln
                165                 170                 175

Ser Gly Leu Phe Glu Ile Gln Pro Gln Gly Ser Pro Pro Phe Leu Val
            180                 185                 190

Asn Cys Lys Met Thr Ser Xaa Gly Gly Trp Thr Val Ile Gln Arg Arg
        195                 200                 205

His Asp Gly Ser Val Asp Phe Asn Arg Pro Trp Glu Ala Tyr Lys Ala
    210                 215                 220

Gly Phe Gly Asp Pro His Gly Glu Phe Trp Leu Gly Leu Glu Lys Val
225                 230                 235                 240

His Ser Ile Thr Gly Asp Arg Asn Ser Arg Leu Ala Val Gln Leu Arg
                245                 250                 255

Asp Trp Asp Gly Asn Ala Glu Leu Leu Gln Phe Ser Val His Leu Gly
            260                 265                 270

Gly Glu Asp Thr Ala Tyr Ser Leu Gln Leu Thr Ala Pro Val Ala Gly
        275                 280                 285

Gln Leu Gly Ala Thr Thr Val Pro Pro Ser Gly Leu Ser Val Pro Phe
    290                 295                 300

Ser Thr Trp Asp Gln Asp His Asp Leu Arg Arg Asp Lys Asn Cys Ala
305                 310                 315                 320

Lys Ser Leu Ser Gly Gly Trp Trp Phe Gly Thr Cys Ser His Ser Asn

```
                      325                 330                 335
Leu Asn Gly Gln Tyr Phe Arg Ser Ile Pro Gln Gln Arg Gln Lys Leu
            340                 345                 350

Lys Lys Gly Ile Phe Trp Lys Thr Trp Arg Gly Arg Tyr Tyr Pro Leu
            355                 360                 365

Gln Ala Thr Thr Met Leu Ile Gln Pro Met Ala Ala Glu Ala Ala Ser
            370                 375                 380

<210> SEQ ID NO 9
<211> LENGTH: 140
<212> TYPE: PRT
<213> ORGANISM: Homo sapiens

<400> SEQUENCE: 9

Ala Gln Gly Gly Pro Val Gln Ser Lys Ser Pro Arg Phe Ala Ser Trp
1               5                   10                  15

Asp Glu Met Asn Val Leu Ala His Gly Leu Leu Gln Leu Gly Gln Gly
            20                  25                  30

Leu Arg Glu His Ala Glu Arg Thr Arg Ser Gln Leu Ser Ala Leu Glu
        35                  40                  45

Arg Arg Leu Ser Ala Cys Gly Ser Ala Cys Gln Gly Thr Glu Gly Ser
50                  55                  60

Thr Asp Leu Pro Leu Ala Pro Glu Ser Arg Val Asp Pro Glu Val Leu
65                  70                  75                  80

His Ser Leu Gln Thr Gln Leu Lys Ala Gln Asn Ser Arg Ile Gln Gln
                85                  90                  95

Leu Phe His Lys Val Ala Gln Gln Arg His Leu Glu Lys Gln His
            100                 105                 110

Leu Arg Ile Gln His Leu Gln Ser Gln Phe Gly Leu Leu Asp His Lys
        115                 120                 125

His Leu Asp His Glu Val Ala Lys Pro Ala Arg Arg
    130                 135                 140

<210> SEQ ID NO 10
<211> LENGTH: 183
<212> TYPE: PRT
<213> ORGANISM: Homo sapiens

<400> SEQUENCE: 10

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140
```

```
Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg
            180

<210> SEQ ID NO 11
<211> LENGTH: 161
<212> TYPE: PRT
<213> ORGANISM: Homo sapiens

<400> SEQUENCE: 11

Ala Gln Gly Gly Pro Val Gln Ser Lys Ser Pro Arg Phe Ala Ser Trp
1               5                   10                  15

Asp Glu Met Asn Val Leu Ala His Gly Leu Leu Gln Leu Gly Gln Gly
                20                  25                  30

Leu Arg Glu His Ala Glu Arg Thr Arg Ser Gln Leu Ser Ala Leu Glu
            35                  40                  45

Arg Arg Leu Ser Ala Cys Gly Ser Ala Cys Gln Gly Thr Glu Gly Ser
        50                  55                  60

Thr Asp Leu Pro Leu Ala Pro Glu Ser Arg Val Asp Pro Glu Val Leu
65                  70                  75                  80

His Ser Leu Gln Thr Gln Leu Lys Ala Gln Asn Ser Arg Ile Gln Gln
                85                  90                  95

Leu Phe His Lys Val Ala Gln Gln Gln Arg His Leu Glu Lys Gln His
                100                 105                 110

Leu Arg Ile Gln His Leu Gln Ser Gln Phe Gly Leu Leu Asp His Lys
            115                 120                 125

His Leu Asp His Glu Val Ala Lys Pro Ala Arg Arg Lys Arg Leu Pro
        130                 135                 140

Glu Met Ala Gln Pro Val Asp Pro Ala His Asn Val Ser Arg Leu His
145                 150                 155                 160

Arg

<210> SEQ ID NO 12
<211> LENGTH: 162
<212> TYPE: PRT
<213> ORGANISM: Homo sapiens

<400> SEQUENCE: 12

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
                20                  25                  30

Pro Arg Phe Ala Ser Trp Asp Glu Met Asn Val Leu Ala His Gly Leu
            35                  40                  45

Leu Gln Leu Gly Gln Gly Leu Arg Glu His Ala Glu Arg Thr Arg Ser
        50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
                100                 105                 110

Asn Ser Arg Ile Gln Gln Leu Phe His Lys Val Ala Gln Gln Gln Arg
```

```
                115                 120                 125
His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg

<210> SEQ ID NO 13
<211> LENGTH: 245
<212> TYPE: PRT
<213> ORGANISM: Homo sapiens
<220> FEATURE:
<221> NAME/KEY: MOD_RES
<222> LOCATION: (60)..(60)
<223> OTHER INFORMATION: Any amino acid

<400> SEQUENCE: 13

Arg Lys Arg Leu Pro Glu Met Ala Gln Pro Val Asp Pro Ala His Asn
1               5                   10                  15

Val Ser Arg Leu His Arg Leu Pro Arg Asp Cys Gln Glu Leu Phe Gln
            20                  25                  30

Val Gly Glu Arg Gln Ser Gly Leu Phe Glu Ile Gln Pro Gln Gly Ser
        35                  40                  45

Pro Pro Phe Leu Val Asn Cys Lys Met Thr Ser Xaa Gly Gly Trp Thr
    50                  55                  60

Val Ile Gln Arg Arg His Asp Gly Ser Val Asp Phe Asn Arg Pro Trp
65                  70                  75                  80

Glu Ala Tyr Lys Ala Gly Phe Gly Asp Pro His Gly Glu Phe Trp Leu
                85                  90                  95

Gly Leu Glu Lys Val His Ser Ile Thr Gly Asp Arg Asn Ser Arg Leu
            100                 105                 110

Ala Val Gln Leu Arg Asp Trp Asp Gly Asn Ala Glu Leu Leu Gln Phe
        115                 120                 125

Ser Val His Leu Gly Gly Glu Asp Thr Ala Tyr Ser Leu Gln Leu Thr
    130                 135                 140

Ala Pro Val Ala Gly Gln Leu Gly Ala Thr Thr Val Pro Pro Ser Gly
145                 150                 155                 160

Leu Ser Val Pro Phe Ser Thr Trp Asp Gln Asp His Asp Leu Arg Arg
                165                 170                 175

Asp Lys Asn Cys Ala Lys Ser Leu Ser Gly Gly Trp Trp Phe Gly Thr
            180                 185                 190

Cys Ser His Ser Asn Leu Asn Gly Gln Tyr Phe Arg Ser Ile Pro Gln
        195                 200                 205

Gln Arg Gln Lys Leu Lys Lys Gly Ile Phe Trp Lys Thr Trp Arg Gly
    210                 215                 220

Arg Tyr Tyr Pro Leu Gln Ala Thr Thr Met Leu Ile Gln Pro Met Ala
225                 230                 235                 240

Ala Glu Ala Ala Ser
                245

<210> SEQ ID NO 14
<211> LENGTH: 223
<212> TYPE: PRT
<213> ORGANISM: Homo sapiens
<220> FEATURE:
<221> NAME/KEY: MOD_RES
<222> LOCATION: (38)..(38)
<223> OTHER INFORMATION: Any amino acid
```

<400> SEQUENCE: 14

```
Leu Pro Arg Asp Cys Gln Glu Leu Phe Gln Val Gly Glu Arg Gln Ser
1               5                   10                  15

Gly Leu Phe Glu Ile Gln Pro Gln Gly Ser Pro Pro Phe Leu Val Asn
            20                  25                  30

Cys Lys Met Thr Ser Xaa Gly Gly Trp Thr Val Ile Gln Arg Arg His
                35                  40                  45

Asp Gly Ser Val Asp Phe Asn Arg Pro Trp Glu Ala Tyr Lys Ala Gly
        50                  55                  60

Phe Gly Asp Pro His Gly Glu Phe Trp Leu Gly Leu Glu Lys Val His
65                  70                  75                  80

Ser Ile Thr Gly Asp Arg Asn Ser Arg Leu Ala Val Gln Leu Arg Asp
                85                  90                  95

Trp Asp Gly Asn Ala Glu Leu Leu Gln Phe Ser Val His Leu Gly Gly
            100                 105                 110

Glu Asp Thr Ala Tyr Ser Leu Gln Leu Thr Ala Pro Val Ala Gly Gln
        115                 120                 125

Leu Gly Ala Thr Thr Val Pro Pro Ser Gly Leu Ser Val Pro Phe Ser
130                 135                 140

Thr Trp Asp Gln Asp His Asp Leu Arg Arg Asp Lys Asn Cys Ala Lys
145                 150                 155                 160

Ser Leu Ser Gly Gly Trp Trp Phe Gly Thr Cys Ser His Ser Asn Leu
                165                 170                 175

Asn Gly Gln Tyr Phe Arg Ser Ile Pro Gln Gln Arg Gln Lys Leu Lys
            180                 185                 190

Lys Gly Ile Phe Trp Lys Thr Trp Arg Gly Arg Tyr Tyr Pro Leu Gln
        195                 200                 205

Ala Thr Thr Met Leu Ile Gln Pro Met Ala Ala Glu Ala Ala Ser
    210                 215                 220
```

<210> SEQ ID NO 15
<211> LENGTH: 144
<212> TYPE: PRT
<213> ORGANISM: Homo sapiens

<400> SEQUENCE: 15

```
Glu Met Asn Val Leu Ala His Gly Leu Leu Gln Leu Gly Gln Gly Leu
1               5                   10                  15

Arg Glu His Ala Glu Arg Thr Arg Ser Gln Leu Ser Ala Leu Glu Arg
            20                  25                  30

Arg Leu Ser Ala Cys Gly Ser Ala Cys Gln Gly Thr Glu Gly Ser Thr
        35                  40                  45

Asp Leu Pro Leu Ala Pro Glu Ser Arg Val Asp Pro Glu Val Leu His
    50                  55                  60

Ser Leu Gln Thr Gln Leu Lys Ala Gln Asn Ser Arg Ile Gln Gln Leu
65                  70                  75                  80

Phe His Lys Val Ala Gln Gln Arg His Leu Glu Lys Gln His Leu Arg
                85                  90                  95

Arg Ile Gln His Leu Gln Ser Gln Phe Gly Leu Leu Asp His Lys His
            100                 105                 110

Leu Asp His Glu Val Ala Lys Pro Ala Arg Arg Lys Arg Leu Pro Glu
        115                 120                 125

Met Ala Gln Pro Val Asp Pro Ala His Asn Val Ser Arg Leu His Arg
    130                 135                 140
```

-continued

```
<210> SEQ ID NO 16
<211> LENGTH: 124
<212> TYPE: PRT
<213> ORGANISM: Homo sapiens

<400> SEQUENCE: 16

Glu Arg Thr Arg Ser Gln Leu Ser Ala Leu Glu Arg Arg Leu Ser Ala
1               5                   10                  15

Cys Gly Ser Ala Cys Gln Gly Thr Glu Gly Ser Thr Asp Leu Pro Leu
            20                  25                  30

Ala Pro Glu Ser Arg Val Asp Pro Glu Val Leu His Ser Leu Gln Thr
        35                  40                  45

Gln Leu Lys Ala Gln Asn Ser Arg Ile Gln Gln Leu Phe His Lys Val
    50                  55                  60

Ala Gln Gln Gln Arg His Leu Glu Lys Gln His Leu Arg Ile Gln His
65                  70                  75                  80

Leu Gln Ser Gln Phe Gly Leu Leu Asp His Lys His Leu Asp His Glu
                85                  90                  95

Val Ala Lys Pro Ala Arg Arg Lys Arg Leu Pro Glu Met Ala Gln Pro
            100                 105                 110

Val Asp Pro Ala His Asn Val Ser Arg Leu His Arg
            115                 120

<210> SEQ ID NO 17
<211> LENGTH: 104
<212> TYPE: PRT
<213> ORGANISM: Homo sapiens

<400> SEQUENCE: 17

Cys Gln Gly Thr Glu Gly Ser Thr Asp Leu Pro Leu Ala Pro Glu Ser
1               5                   10                  15

Arg Val Asp Pro Glu Val Leu His Ser Leu Gln Thr Gln Leu Lys Ala
            20                  25                  30

Gln Asn Ser Arg Ile Gln Gln Leu Phe His Lys Val Ala Gln Gln Gln
        35                  40                  45

Arg His Leu Glu Lys Gln His Leu Arg Ile Gln His Leu Gln Ser Gln
    50                  55                  60

Phe Gly Leu Leu Asp His Lys His Leu Asp His Glu Val Ala Lys Pro
65                  70                  75                  80

Ala Arg Arg Lys Arg Leu Pro Glu Met Ala Gln Pro Val Asp Pro Ala
                85                  90                  95

His Asn Val Ser Arg Leu His Arg
            100

<210> SEQ ID NO 18
<211> LENGTH: 84
<212> TYPE: PRT
<213> ORGANISM: Homo sapiens

<400> SEQUENCE: 18

Glu Val Leu His Ser Leu Gln Thr Gln Leu Lys Ala Gln Asn Ser Arg
1               5                   10                  15

Ile Gln Gln Leu Phe His Lys Val Ala Gln Gln Gln Arg His Leu Glu
            20                  25                  30

Lys Gln His Leu Arg Ile Gln His Leu Gln Ser Gln Phe Gly Leu Leu
        35                  40                  45

Asp His Lys His Leu Asp His Glu Val Ala Lys Pro Ala Arg Arg Lys
    50                  55                  60
```

```
Arg Leu Pro Glu Met Ala Gln Pro Val Asp Pro Ala His Asn Val Ser
 65                  70                  75                  80

Arg Leu His Arg

<210> SEQ ID NO 19
<211> LENGTH: 64
<212> TYPE: PRT
<213> ORGANISM: Homo sapiens

<400> SEQUENCE: 19

Phe His Lys Val Ala Gln Gln Arg His Leu Glu Lys Gln His Leu
  1               5                  10                  15

Arg Ile Gln His Leu Gln Ser Gln Phe Gly Leu Leu Asp His Lys His
                 20                  25                  30

Leu Asp His Glu Val Ala Lys Pro Ala Arg Arg Lys Arg Leu Pro Glu
             35                  40                  45

Met Ala Gln Pro Val Asp Pro Ala His Asn Val Ser Arg Leu His Arg
         50                  55                  60

<210> SEQ ID NO 20
<211> LENGTH: 44
<212> TYPE: PRT
<213> ORGANISM: Homo sapiens

<400> SEQUENCE: 20

Leu Gln Ser Gln Phe Gly Leu Leu Asp His Lys His Leu Asp His Glu
  1               5                  10                  15

Val Ala Lys Pro Ala Arg Arg Lys Arg Leu Pro Glu Met Ala Gln Pro
                 20                  25                  30

Val Asp Pro Ala His Asn Val Ser Arg Leu His Arg
             35                  40

<210> SEQ ID NO 21
<211> LENGTH: 367
<212> TYPE: PRT
<213> ORGANISM: Homo sapiens
<220> FEATURE:
<221> NAME/KEY: MOD_RES
<222> LOCATION: (182)..(182)
<223> OTHER INFORMATION: Any amino acid

<400> SEQUENCE: 21

Glu Met Asn Val Leu Ala His Gly Leu Leu Gln Leu Gly Gln Gly Leu
  1               5                  10                  15

Arg Glu His Ala Glu Arg Thr Arg Ser Gln Leu Ser Ala Leu Glu Arg
                 20                  25                  30

Arg Leu Ser Ala Cys Gly Ser Ala Cys Gln Gly Thr Glu Gly Ser Thr
             35                  40                  45

Asp Leu Pro Leu Ala Pro Glu Ser Arg Val Asp Pro Glu Val Leu His
         50                  55                  60

Ser Leu Gln Thr Gln Leu Lys Ala Gln Asn Ser Arg Ile Gln Gln Leu
 65                  70                  75                  80

Phe His Lys Val Ala Gln Gln Arg His Leu Glu Lys Gln His Leu
                 85                  90                  95

Arg Ile Gln His Leu Gln Ser Gln Phe Gly Leu Leu Asp His Lys His
                100                 105                 110

Leu Asp His Glu Val Ala Lys Pro Ala Arg Arg Lys Arg Leu Pro Glu
            115                 120                 125

Met Ala Gln Pro Val Asp Pro Ala His Asn Val Ser Arg Leu His Arg
        130                 135                 140
```

```
Leu Pro Arg Asp Cys Gln Glu Leu Phe Gln Val Gly Glu Arg Gln Ser
145                 150                 155                 160

Gly Leu Phe Glu Ile Gln Pro Gln Gly Ser Pro Pro Phe Leu Val Asn
            165                 170                 175

Cys Lys Met Thr Ser Xaa Gly Gly Trp Thr Val Ile Gln Arg Arg His
            180                 185                 190

Asp Gly Ser Val Asp Phe Asn Arg Pro Trp Glu Ala Tyr Lys Ala Gly
            195                 200                 205

Phe Gly Asp Pro His Gly Glu Phe Trp Leu Gly Leu Glu Lys Val His
            210                 215                 220

Ser Ile Thr Gly Asp Arg Asn Ser Arg Leu Ala Val Gln Leu Arg Asp
225                 230                 235                 240

Trp Asp Gly Asn Ala Glu Leu Leu Gln Phe Ser Val His Leu Gly Gly
                245                 250                 255

Glu Asp Thr Ala Tyr Ser Leu Gln Leu Thr Ala Pro Val Ala Gly Gln
            260                 265                 270

Leu Gly Ala Thr Thr Val Pro Pro Ser Gly Leu Ser Val Pro Phe Ser
            275                 280                 285

Thr Trp Asp Gln Asp His Asp Leu Arg Arg Asp Lys Asn Cys Ala Lys
            290                 295                 300

Ser Leu Ser Gly Gly Trp Trp Phe Gly Thr Cys Ser His Ser Asn Leu
305                 310                 315                 320

Asn Gly Gln Tyr Phe Arg Ser Ile Pro Gln Gln Arg Gln Lys Leu Lys
                325                 330                 335

Lys Gly Ile Phe Trp Lys Thr Trp Arg Gly Arg Tyr Tyr Pro Leu Gln
            340                 345                 350

Ala Thr Thr Met Leu Ile Gln Pro Met Ala Ala Glu Ala Ala Ser
            355                 360                 365

<210> SEQ ID NO 22
<211> LENGTH: 347
<212> TYPE: PRT
<213> ORGANISM: Homo sapiens
<220> FEATURE:
<221> NAME/KEY: MOD_RES
<222> LOCATION: (162)..(162)
<223> OTHER INFORMATION: Any amino acid

<400> SEQUENCE: 22

Glu Arg Thr Arg Ser Gln Leu Ser Ala Leu Glu Arg Arg Leu Ser Ala
1               5                   10                  15

Cys Gly Ser Ala Cys Gln Gly Thr Glu Gly Ser Thr Asp Leu Pro Leu
            20                  25                  30

Ala Pro Glu Ser Arg Val Asp Pro Glu Val Leu His Ser Leu Gln Thr
        35                  40                  45

Gln Leu Lys Ala Gln Asn Ser Arg Ile Gln Gln Leu Phe His Lys Val
    50                  55                  60

Ala Gln Gln Gln Arg His Leu Glu Lys Gln His Leu Arg Ile Gln His
65                  70                  75                  80

Leu Gln Ser Gln Phe Gly Leu Leu Asp His Lys His Leu Asp His Glu
                85                  90                  95

Val Ala Lys Pro Ala Arg Arg Lys Arg Leu Pro Glu Met Ala Gln Pro
            100                 105                 110

Val Asp Pro Ala His Asn Val Ser Arg Leu His Arg Leu Pro Arg Asp
        115                 120                 125

Cys Gln Glu Leu Phe Gln Val Gly Glu Arg Gln Ser Gly Leu Phe Glu
```

```
                130                 135                 140
Ile Gln Pro Gln Gly Ser Pro Pro Phe Leu Val Asn Cys Lys Met Thr
145                 150                 155                 160

Ser Xaa Gly Gly Trp Thr Val Ile Gln Arg Arg His Asp Gly Ser Val
                165                 170                 175

Asp Phe Asn Arg Pro Trp Glu Ala Tyr Lys Ala Gly Phe Gly Asp Pro
                180                 185                 190

His Gly Glu Phe Trp Leu Gly Leu Glu Lys Val His Ser Ile Thr Gly
                195                 200                 205

Asp Arg Asn Ser Arg Leu Ala Val Gln Leu Arg Asp Trp Asp Gly Asn
            210                 215                 220

Ala Glu Leu Leu Gln Phe Ser Val His Leu Gly Gly Glu Asp Thr Ala
225                 230                 235                 240

Tyr Ser Leu Gln Leu Thr Ala Pro Val Ala Gly Gln Leu Gly Ala Thr
                245                 250                 255

Thr Val Pro Pro Ser Gly Leu Ser Val Pro Phe Ser Thr Trp Asp Gln
                260                 265                 270

Asp His Asp Leu Arg Arg Asp Lys Asn Cys Ala Lys Ser Leu Ser Gly
            275                 280                 285

Gly Trp Trp Phe Gly Thr Cys Ser His Ser Asn Leu Asn Gly Gln Tyr
290                 295                 300

Phe Arg Ser Ile Pro Gln Gln Arg Gln Lys Leu Lys Lys Gly Ile Phe
305                 310                 315                 320

Trp Lys Thr Trp Arg Gly Arg Tyr Tyr Pro Leu Gln Ala Thr Thr Met
                325                 330                 335

Leu Ile Gln Pro Met Ala Ala Glu Ala Ala Ser
                340                 345

<210> SEQ ID NO 23
<211> LENGTH: 327
<212> TYPE: PRT
<213> ORGANISM: Homo sapiens
<220> FEATURE:
<221> NAME/KEY: MOD_RES
<222> LOCATION: (142)..(142)
<223> OTHER INFORMATION: Any amino acid

<400> SEQUENCE: 23

Cys Gln Gly Thr Glu Gly Ser Thr Asp Leu Pro Leu Ala Pro Glu Ser
1               5                   10                  15

Arg Val Asp Pro Glu Val Leu His Ser Leu Gln Thr Gln Leu Lys Ala
                20                  25                  30

Gln Asn Ser Arg Ile Gln Gln Leu Phe His Lys Val Ala Gln Gln Gln
            35                  40                  45

Arg His Leu Glu Lys Gln His Leu Arg Ile Gln His Leu Gln Ser Gln
        50                  55                  60

Phe Gly Leu Leu Asp His Lys His Leu Asp His Glu Val Ala Lys Pro
65                  70                  75                  80

Ala Arg Arg Lys Arg Leu Pro Glu Met Ala Gln Pro Val Asp Pro Ala
                85                  90                  95

His Asn Val Ser Arg Leu His Arg Leu Pro Arg Asp Cys Gln Glu Leu
                100                 105                 110

Phe Gln Val Gly Glu Arg Gln Ser Gly Leu Phe Glu Ile Gln Pro Gln
            115                 120                 125

Gly Ser Pro Pro Phe Leu Val Asn Cys Lys Met Thr Ser Xaa Gly Gly
        130                 135                 140
```

```
Trp Thr Val Ile Gln Arg Arg His Asp Gly Ser Val Asp Phe Asn Arg
145                 150                 155                 160

Pro Trp Glu Ala Tyr Lys Ala Gly Phe Gly Asp Pro His Gly Glu Phe
            165                 170                 175

Trp Leu Gly Leu Glu Lys Val His Ser Ile Thr Gly Asp Arg Asn Ser
            180                 185                 190

Arg Leu Ala Val Gln Leu Arg Asp Trp Asp Gly Asn Ala Glu Leu Leu
            195                 200                 205

Gln Phe Ser Val His Leu Gly Gly Glu Asp Thr Ala Tyr Ser Leu Gln
210                 215                 220

Leu Thr Ala Pro Val Ala Gly Gln Leu Gly Ala Thr Thr Val Pro Pro
225                 230                 235                 240

Ser Gly Leu Ser Val Pro Phe Ser Thr Trp Asp Gln Asp His Asp Leu
            245                 250                 255

Arg Arg Asp Lys Asn Cys Ala Lys Ser Leu Ser Gly Gly Trp Trp Phe
            260                 265                 270

Gly Thr Cys Ser His Ser Asn Leu Asn Gly Gln Tyr Phe Arg Ser Ile
            275                 280                 285

Pro Gln Gln Arg Gln Lys Leu Lys Lys Gly Ile Phe Trp Lys Thr Trp
            290                 295                 300

Arg Gly Arg Tyr Tyr Pro Leu Gln Ala Thr Thr Met Leu Ile Gln Pro
305                 310                 315                 320

Met Ala Ala Glu Ala Ala Ser
                325

<210> SEQ ID NO 24
<211> LENGTH: 307
<212> TYPE: PRT
<213> ORGANISM: Homo sapiens
<220> FEATURE:
<221> NAME/KEY: MOD_RES
<222> LOCATION: (122)..(122)
<223> OTHER INFORMATION: Any amino acid

<400> SEQUENCE: 24

Glu Val Leu His Ser Leu Gln Thr Gln Leu Lys Ala Gln Asn Ser Arg
1               5                   10                  15

Ile Gln Gln Leu Phe His Lys Val Ala Gln Gln Arg His Leu Glu
            20                  25                  30

Lys Gln His Leu Arg Ile Gln His Leu Gln Ser Gln Phe Gly Leu Leu
            35                  40                  45

Asp His Lys His Leu Asp His Glu Val Ala Lys Pro Ala Arg Arg Lys
        50                  55                  60

Arg Leu Pro Glu Met Ala Gln Pro Val Asp Pro Ala His Asn Val Ser
65                  70                  75                  80

Arg Leu His Arg Leu Pro Arg Asp Cys Gln Glu Leu Phe Gln Val Gly
            85                  90                  95

Glu Arg Gln Ser Gly Leu Phe Glu Ile Gln Pro Gln Gly Ser Pro Pro
            100                 105                 110

Phe Leu Val Asn Cys Lys Met Thr Ser Xaa Gly Gly Trp Thr Val Ile
            115                 120                 125

Gln Arg Arg His Asp Gly Ser Val Asp Phe Asn Arg Pro Trp Glu Ala
            130                 135                 140

Tyr Lys Ala Gly Phe Gly Asp Pro His Gly Glu Phe Trp Leu Gly Leu
145                 150                 155                 160

Glu Lys Val His Ser Ile Thr Gly Asp Arg Asn Ser Arg Leu Ala Val
            165                 170                 175
```

```
Gln Leu Arg Asp Trp Asp Gly Asn Ala Glu Leu Leu Gln Phe Ser Val
            180                 185                 190

His Leu Gly Gly Glu Asp Thr Ala Tyr Ser Leu Gln Leu Thr Ala Pro
        195                 200                 205

Val Ala Gly Gln Leu Gly Ala Thr Thr Val Pro Pro Ser Gly Leu Ser
210                 215                 220

Val Pro Phe Ser Thr Trp Asp Gln Asp His Asp Leu Arg Arg Asp Lys
225                 230                 235                 240

Asn Cys Ala Lys Ser Leu Ser Gly Gly Trp Trp Phe Gly Thr Cys Ser
                245                 250                 255

His Ser Asn Leu Asn Gly Gln Tyr Phe Arg Ser Ile Pro Gln Gln Arg
            260                 265                 270

Gln Lys Leu Lys Lys Gly Ile Phe Trp Lys Thr Trp Arg Gly Arg Tyr
        275                 280                 285

Tyr Pro Leu Gln Ala Thr Thr Met Leu Ile Gln Pro Met Ala Ala Glu
    290                 295                 300

Ala Ala Ser
305

<210> SEQ ID NO 25
<211> LENGTH: 287
<212> TYPE: PRT
<213> ORGANISM: Homo sapiens
<220> FEATURE:
<221> NAME/KEY: MOD_RES
<222> LOCATION: (102)..(102)
<223> OTHER INFORMATION: Any amino acid

<400> SEQUENCE: 25

Phe His Lys Val Ala Gln Gln Arg His Leu Glu Lys Gln His Leu
1               5                  10                  15

Arg Ile Gln His Leu Gln Ser Gln Phe Gly Leu Leu Asp His Lys His
            20                  25                  30

Leu Asp His Glu Val Ala Lys Pro Ala Arg Arg Lys Arg Leu Pro Glu
        35                  40                  45

Met Ala Gln Pro Val Asp Pro Ala His Asn Val Ser Arg Leu His Arg
    50                  55                  60

Leu Pro Arg Asp Cys Gln Glu Leu Phe Gln Val Gly Glu Arg Gln Ser
65                  70                  75                  80

Gly Leu Phe Glu Ile Gln Pro Gln Gly Ser Pro Pro Phe Leu Val Asn
                85                  90                  95

Cys Lys Met Thr Ser Xaa Gly Gly Trp Thr Val Ile Gln Arg Arg His
            100                 105                 110

Asp Gly Ser Val Asp Phe Asn Arg Pro Trp Glu Ala Tyr Lys Ala Gly
        115                 120                 125

Phe Gly Asp Pro His Gly Glu Phe Trp Leu Gly Leu Glu Lys Val His
    130                 135                 140

Ser Ile Thr Gly Asp Arg Asn Ser Arg Leu Ala Val Gln Leu Arg Asp
145                 150                 155                 160

Trp Asp Gly Asn Ala Glu Leu Leu Gln Phe Ser Val His Leu Gly Gly
                165                 170                 175

Glu Asp Thr Ala Tyr Ser Leu Gln Leu Thr Ala Pro Val Ala Gly Gln
            180                 185                 190

Leu Gly Ala Thr Thr Val Pro Pro Ser Gly Leu Ser Val Pro Phe Ser
        195                 200                 205

Thr Trp Asp Gln Asp His Asp Leu Arg Arg Asp Lys Asn Cys Ala Lys
```

```
                     210                 215                 220
Ser Leu Ser Gly Gly Trp Trp Phe Gly Thr Cys Ser His Ser Asn Leu
225                 230                 235                 240

Asn Gly Gln Tyr Phe Arg Ser Ile Pro Gln Gln Arg Gln Lys Leu Lys
            245                 250                 255

Lys Gly Ile Phe Trp Lys Thr Trp Arg Gly Arg Tyr Tyr Pro Leu Gln
        260                 265                 270

Ala Thr Thr Met Leu Ile Gln Pro Met Ala Ala Glu Ala Ala Ser
    275                 280                 285

<210> SEQ ID NO 26
<211> LENGTH: 267
<212> TYPE: PRT
<213> ORGANISM: Homo sapiens
<220> FEATURE:
<221> NAME/KEY: MOD_RES
<222> LOCATION: (82)..(82)
<223> OTHER INFORMATION: Any amino acid

<400> SEQUENCE: 26

Leu Gln Ser Gln Phe Gly Leu Leu Asp His Lys His Leu Asp His Glu
1               5                   10                  15

Val Ala Lys Pro Ala Arg Arg Lys Arg Leu Pro Glu Met Ala Gln Pro
            20                  25                  30

Val Asp Pro Ala His Asn Val Ser Arg Leu His Arg Leu Pro Arg Asp
        35                  40                  45

Cys Gln Glu Leu Phe Gln Val Gly Glu Arg Gln Ser Gly Leu Phe Glu
    50                  55                  60

Ile Gln Pro Gln Gly Ser Pro Pro Phe Leu Val Asn Cys Lys Met Thr
65                  70                  75                  80

Ser Xaa Gly Gly Trp Thr Val Ile Gln Arg Arg His Asp Gly Ser Val
                85                  90                  95

Asp Phe Asn Arg Pro Trp Glu Ala Tyr Lys Ala Gly Phe Gly Asp Pro
            100                 105                 110

His Gly Glu Phe Trp Leu Gly Leu Glu Lys Val His Ser Ile Thr Gly
        115                 120                 125

Asp Arg Asn Ser Arg Leu Ala Val Gln Leu Arg Asp Trp Asp Gly Asn
    130                 135                 140

Ala Glu Leu Leu Gln Phe Ser Val His Leu Gly Gly Glu Asp Thr Ala
145                 150                 155                 160

Tyr Ser Leu Gln Leu Thr Ala Pro Val Ala Gly Gln Leu Gly Ala Thr
                165                 170                 175

Thr Val Pro Pro Ser Gly Leu Ser Val Pro Phe Ser Thr Trp Asp Gln
            180                 185                 190

Asp His Asp Leu Arg Arg Asp Lys Asn Cys Ala Lys Ser Leu Ser Gly
        195                 200                 205

Gly Trp Trp Phe Gly Thr Cys Ser His Ser Asn Leu Asn Gly Gln Tyr
    210                 215                 220

Phe Arg Ser Ile Pro Gln Gln Arg Gln Lys Leu Lys Lys Gly Ile Phe
225                 230                 235                 240

Trp Lys Thr Trp Arg Gly Arg Tyr Tyr Pro Leu Gln Ala Thr Thr Met
                245                 250                 255

Leu Ile Gln Pro Met Ala Ala Glu Ala Ala Ser
            260                 265

<210> SEQ ID NO 27
<211> LENGTH: 247
```

```
<212> TYPE: PRT
<213> ORGANISM: Homo sapiens
<220> FEATURE:
<221> NAME/KEY: MOD_RES
<222> LOCATION: (62)..(62)
<223> OTHER INFORMATION: Any amino acid

<400> SEQUENCE: 27

Ala Arg Arg Lys Arg Leu Pro Glu Met Ala Gln Pro Val Asp Pro Ala
1               5                   10                  15

His Asn Val Ser Arg Leu His Arg Leu Pro Arg Asp Cys Gln Glu Leu
            20                  25                  30

Phe Gln Val Gly Glu Arg Gln Ser Gly Leu Phe Glu Ile Gln Pro Gln
        35                  40                  45

Gly Ser Pro Pro Phe Leu Val Asn Cys Lys Met Thr Ser Xaa Gly Gly
    50                  55                  60

Trp Thr Val Ile Gln Arg Arg His Asp Gly Ser Val Asp Phe Asn Arg
65                  70                  75                  80

Pro Trp Glu Ala Tyr Lys Ala Gly Phe Gly Asp Pro His Gly Glu Phe
                85                  90                  95

Trp Leu Gly Leu Glu Lys Val His Ser Ile Thr Gly Asp Arg Asn Ser
            100                 105                 110

Arg Leu Ala Val Gln Leu Arg Asp Trp Asp Gly Asn Ala Glu Leu Leu
        115                 120                 125

Gln Phe Ser Val His Leu Gly Gly Glu Asp Thr Ala Tyr Ser Leu Gln
    130                 135                 140

Leu Thr Ala Pro Val Ala Gly Gln Leu Gly Ala Thr Thr Val Pro Pro
145                 150                 155                 160

Ser Gly Leu Ser Val Pro Phe Ser Thr Trp Asp Gln Asp His Asp Leu
                165                 170                 175

Arg Arg Asp Lys Asn Cys Ala Lys Ser Leu Ser Gly Gly Trp Trp Phe
            180                 185                 190

Gly Thr Cys Ser His Ser Asn Leu Asn Gly Gln Tyr Phe Arg Ser Ile
        195                 200                 205

Pro Gln Gln Arg Gln Lys Leu Lys Lys Gly Ile Phe Trp Lys Thr Trp
    210                 215                 220

Arg Gly Arg Tyr Tyr Pro Leu Gln Ala Thr Thr Met Leu Ile Gln Pro
225                 230                 235                 240

Met Ala Ala Glu Ala Ala Ser
                245

<210> SEQ ID NO 28
<211> LENGTH: 406
<212> TYPE: PRT
<213> ORGANISM: Homo sapiens
<220> FEATURE:
<221> NAME/KEY: MOD_RES
<222> LOCATION: (221)..(221)
<223> OTHER INFORMATION: Any amino acid

<400> SEQUENCE: 28

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60
```

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
            85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
            115                 120                 125

His Leu Glu Lys Gln His Leu Arg Ile Gln His Leu Gln Ser Gln Phe
130                 135                 140

Gly Leu Leu Asp His Lys His Leu Asp His Glu Val Ala Lys Pro Ala
145                 150                 155                 160

Arg Gly Lys Glu Leu Pro Glu Met Ala Gln Pro Val Asp Pro Ala His
            165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
            195                 200                 205

Ser Pro Pro Phe Leu Val Asn Cys Lys Met Thr Ser Xaa Gly Gly Trp
210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
            245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
            275                 280                 285

Phe Ser Val His Leu Gly Gly Glu Asp Thr Ala Tyr Ser Leu Gln Leu
290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
            325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
            355                 360                 365

Gln Gln Arg Gln Lys Leu Lys Lys Gly Ile Phe Trp Lys Thr Trp Arg
370                 375                 380

Gly Arg Tyr Tyr Pro Leu Gln Ala Thr Thr Met Leu Ile Gln Pro Met
385                 390                 395                 400

Ala Ala Glu Ala Ala Ser
            405

<210> SEQ ID NO 29
<211> LENGTH: 140
<212> TYPE: PRT
<213> ORGANISM: Homo sapiens

<400> SEQUENCE: 29

Ala Gln Gly Gly Pro Val Gln Ser Lys Ser Pro Arg Phe Ala Ser Trp
1               5                   10                  15

Asp Glu Met Asn Val Leu Ala His Gly Leu Leu Gln Leu Gly Gln Gly
            20                  25                  30

```
Leu Arg Glu His Ala Glu Arg Thr Arg Ser Gln Leu Ser Ala Leu Glu
        35                  40                  45

Arg Arg Leu Ser Ala Cys Gly Ser Ala Cys Gln Gly Thr Glu Gly Ser
    50                  55                  60

Thr Asp Leu Pro Leu Ala Pro Glu Ser Arg Val Asp Pro Glu Val Leu
65                  70                  75                  80

His Ser Leu Gln Thr Gln Leu Lys Ala Gln Asn Ser Arg Ile Gln Gln
                85                  90                  95

Leu Phe His Lys Val Ala Gln Gln Gln Arg His Leu Glu Lys Gln His
            100                 105                 110

Leu Arg Ile Gln His Leu Gln Ser Gln Phe Gly Leu Leu Asp His Lys
        115                 120                 125

His Leu Asp His Glu Val Ala Lys Pro Ala Arg Arg
    130                 135                 140

<210> SEQ ID NO 30
<211> LENGTH: 162
<212> TYPE: PRT
<213> ORGANISM: Homo sapiens

<400> SEQUENCE: 30

Ala Gln Gly Gly Pro Val Gln Ser Lys Ser Pro Arg Phe Ala Ser Trp
1               5                   10                  15

Asp Glu Met Asn Val Leu Ala His Gly Leu Leu Gln Leu Gly Gln Gly
                20                  25                  30

Leu Arg Glu His Ala Glu Arg Thr Arg Ser Gln Leu Ser Ala Leu Glu
        35                  40                  45

Arg Arg Leu Ser Ala Cys Gly Ser Ala Cys Gln Gly Thr Glu Gly Ser
    50                  55                  60

Thr Asp Leu Pro Leu Ala Pro Glu Ser Arg Val Asp Pro Glu Val Leu
65                  70                  75                  80

His Ser Leu Gln Thr Gln Leu Lys Ala Gln Asn Ser Arg Ile Gln Gln
                85                  90                  95

Leu Phe His Lys Val Ala Gln Gln Gln Arg His Leu Glu Lys Gln His
            100                 105                 110

Leu Arg Ile Gln His Leu Gln Ser Gln Phe Gly Leu Leu Asp His Lys
        115                 120                 125

His Leu Asp His Glu Val Ala Lys Pro Ala Arg Arg Lys Arg Leu Pro
    130                 135                 140

Glu Met Ala Gln Pro Val Asp Pro Ala His Asn Val Ser Arg Leu His
145                 150                 155                 160

Arg Leu
```

METHODS OF USING ANGIOPOIETIN-LIKE 4 PROTEIN TO STIMULATE PROLIFERATION OF PRE-ADIPOCYTES

RELATED APPLICATIONS

This application is a continuation and claims the benefit under 35 U.S.C. §120 of U.S. patent application Ser. No. 11/540,430, filed Sep. 28, 2006 (abandoned), which is a continuation application and claims the benefit under 35 U.S.C. §120 of U.S. patent application Ser. No. 11/185,204, filed on Jul. 19, 2005 (now U.S. Pat. No. 7,371,384), which claims the benefit, under 35 U.S.C. §119, of U.S. Provisional Patent Application Ser. No. 60/589,875 filed Jul. 20, 2004, the contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Jun. 15, 2011, is named GNE208C1.txt and is 51,633 bytes in size.

FIELD OF THE INVENTION

The invention concerns angiopoietin-like 4 protein (ANGPTL4). The invention relates to compositions and methods of using ANGPTL4 and agonists and antagonists thereof, for the diagnosis and treatment of diseases or disorders.

BACKGROUND OF THE INVENTION

Angiopoietin-like 4 protein (ANGPTL4) is a member of the angiopoietin family of secreted proteins. Conserved regions of the angiopoietin family include a coiled-coil domain and a C-terminal fibrinogen (FBN)-like domain. See, e.g., Kim et al., *Biochem. J.* 346:603-610 (2000). Other members of the family include angiopoietin 1, angiopoietin 2 and angiopoietin 3. Angiopoietin 1, angiopoietin 2 and angiopoietin3/angiopoietin 4 bind to Tie2 receptor. See, e.g., Davis et al., *Cell* 87, 1161-1169 (1996); Maisonpierre et al., *Science* 277, 55-60 (1997); Valenzuela et al, *Proc. Natl. Acad. Sci. USA* 96, 1904-1909 (1999); and, U.S. Pat. Nos. 5,521,073; 5,650,490; and, 5,814,464. Angiopoietin 1 and 4 appear to be an agonist for the Tie2 receptor, while Angiopoietin 2 and 3 appear to be an antagonist (and possibly an agonist) for the Tie2 receptor. See, e.g., Folkman & D'Amore, *Cell*, 87:1153-1155 (1996); Suri et al., *Cell*, 87:1171-1180 (1996); Masionpierre et al., *Science* 277:55-60 (1997); and, Ward & Dumont, *Seminars in Cell & Developmental Biology*, 13:19-27 (2002). The Tie2 receptor belongs to a family of endothelial cell specific receptors tyrosine kinases, which also include the Tie1 orphan receptor. Another member of the family, angiopoietin-like 3 protein was found to bind to integrin $\alpha_V\beta_3$. See, e.g., US patent application 20030215451 and Camenisch et al., *J. Biol. Chem.*, 277(19):17281-17290 (2002).

ANGPTL4 is known by other terms. For example, ANGPTL4 is also known as hepatic fibrinogen/angiopoietin-related protein (HFARP) (Kim et al., *Biochem. J.* 346:603-610 (2000)), PPARγ angiopoietin related protein (PGAR) (Yoon, et al., *Mol. Cell Biol.*, 20:5343-5349 (2000)), and fasting induced adipose factor (FIAF) (Kerten et al., *J. Biol. Chem.*, 275:28488-28493 (2000)).

In vitro and in vivo studies and characterizations of ANGPTL4 can provide valuable identification and discovery of therapeutics and/or treatments useful in the prevention, amelioration or correction of diseases or dysfunctions associated with ANGPTL4 activity and/or expression. For example, tissue culture studies and genetically engineered mice have proven to be invaluable tools for the functional dissection of biological processes relevant to human disease, including immunology, cancer, neurobiology, cardiovascular biology, obesity and many others. There is a need to discover and understand the many biological functions of ANGPTL4. The invention addresses these and other needs, as will be apparent upon review of the following disclosure.

SUMMARY OF THE INVENTION

The invention concerns angiopoietin-like 4 protein (ANGPTL4). The invention provides the use of ANGPTL4 or subsequence thereof, or an agonist or antagonist thereof, to treat conditions or diseases characterized by aberrant ANGPTL4 expression or activity, and/or involving ANGPTL4 expression and/or activity.

Methods of modulating the proliferation of hepatocytes by ANGPTL4, or agonists or antagonists thereof, are provided. In certain embodiments, methods include inducing the proliferation of hepatocytes. For example, a method comprises administering an effective amount of an ANGPTL4 or ANGPTL4 agonist to a population of hepatocytes or pre-hepatocytes thereby inducing proliferation. In one aspect, the administration step comprises administering a nucleic acid that encodes for the ANGPTL4. Alternatively or additionally, an effective amount of an agent that induces production of ANGPTL4 in a hepatocyte or pre-hepatocyte can be administered to stimulate proliferation. ANGPTL4 or agonists of ANGPTL4 can be used in the treatment of liver dysfunction, diseases and damage by administering an effective amount of an ANGPTL4 or agonist. In one aspect, the ANGPTL4 is provided by a nucleic acid encoding the ANGPTL4. In one embodiment of the invention, an ANGPTL4 agonist is an agonist for an $\alpha_V\beta_5$ receptor.

Methods for inhibiting the proliferation of hepatocytes are also provided. In certain embodiments, the method includes administering an effective amount of a composition comprising an ANGPTL4 antagonist to a population of hepatocytes or pre-hepatocytes. In one aspect, the ANGPTL4 antagonist is an agent that inhibits ANGPTL4 protein production, e.g., an antisense or ribozyme molecule. In one aspect, the ANGPTL4 antagonist is an anti-ANGPTL4 antibody. In another aspect, the ANGPTL4 antagonist is an anti-$\alpha_V\beta_5$ antagonist antibody. In one embodiment, the ANGPTL4 antagonist is an ANGPTL4-SiRNA. ANGPTL4 antagonists can be used in the treatment, e.g., of liver cancer or undesired liver hypertrophy, by administering an effective amount of the ANGPTL4 antagonist to the hepatocytes.

Methods for modulating cell adhesion of hepatocytes are also provided. In certain embodiments, the methods include inducing cell adhesion of hepatocytes by administering an effective amount of a composition comprising an ANGPTL4 or ANGPTL4 agonist to a population of hepatocytes. In other embodiments, the methods include inhibiting cell adhesion of hepatocytes by administering an effective amount of a composition comprising an ANGPTL4 antagonist to a population of hepatocytes, thereby inhibiting cell adhesion of the hepatocytes.

In addition to modulating proliferation and cell adhesion of hepatocytes, which are involved in lipid homeostasis, ANGPTL4 modulates triglyceride and cholesterol levels in serum, and stimulates pre-adipocyte proliferation, which are also involved in lipid homeostasis. The invention provides methods of modulating a number of various aspects of lipid homeostasis. For example, methods of the invention include stimulating proliferation of pre-adipocytes by administering an effective amount of a composition comprising an ANGPTL4 or ANGPTL4 agonist to a population of preadipocytes, thereby inducing the proliferation of pre-adipocytes. Methods of inhibiting the proliferation of pre-adipocytes are also provided. For example, methods include administering an effective amount of a composition comprising an ANGPTL4 antagonist to a population of preadipocytes. Methods of modulation cell migration of pre-adipocytes is also included. For example, methods of the invention include inducing cell migration of pre-adipocytes by administering an effective amount of ANGPTL4 or ANGPTL4 agonist to a population of pre-adipocytes. Methods of inhibiting cell migration of pre-adipocytes is also provided, which include, e.g., administering an effective amount of an ANGPTL4 antagonist to a population of pre-adipocytes, thereby inhibiting cell migration.

Methods of modulating serum levels of triglycerides or cholesterol in a subject are also provided in the invention. For example, methods include administering an effective amount of a composition comprising an ANGPTL4 or ANGPTL4 agonist or an ANGPTL4 antagonist to a subject, thereby modulation the serum levels of triglycerides and/or cholesterol in a subject. In one embodiment, an ANGPTL4 or ANGPTL4 agonist is administered, which results in an accumulation of triglycerides and/or cholesterol in the serum of a subject compared to a control. In another embodiment, an effective amount of an ANGPTL4 antagonist is administered to a subject, thereby reducing the level of at least one triglyceride, free fatty acids and/or cholesterol in the serum of the subject. In certain embodiments of the invention, a control is serum from a subject before treatment, or a subject with no treatment or reduced treatment, etc.

An ANGPTL4 and ANGPTL4 modulator (agonist or antagonist thereof) can be used in treatment of lipid homeostasis disorders by administering an effective amount of the molecule to a subject. See "Lipid homeostasis disorder" under the definitions herein. For example, a method comprises administering to a subject a composition comprising ANGPTL4 antagonist in an amount effective to treat hyperlipidemia.

Methods of treating obesity and/or reducing total body mass in a subject are also provided. For example, a method includes administering to a subject an effective amount of ANGPTL4 modulator, thereby treating obesity and/or reducing total body mass in the subject compared to no treatment or treatment with a control. In one embodiment, adiposity (fat) of a subject is reduced. In this manner, conditions related to obesity can also be treated, e.g., cardiovascular disease, diabetes, etc.

In certain embodiments of the invention, the cells, e.g., the hepatocytes, pre-adipocytes, are in a subject. Typically, the subject is a human.

An ANGPTL4 of the invention includes full-length protein as well as biological active molecules, e.g., residues corresponding the N-terminal, N-terminal coiled-coil domain, C-terminal, C-terminal fibrinogen-like domain, or ANGPTL4 (1-183) (SEQ ID NO: 10), ANGPTL4 (23-183) (SEQ ID NO: 11), ANGPTL4 (1 to about 162) (SEQ ID NO: 12), ANGPTL4 (about 162-406) (SEQ ID NO: 13), ANGPTL4 (23-406) (SEQ ID NO: 8), or ANGPTL4 (184-406) (SEQ ID NO: 14) amino acid subsequence of human ANGPTL4, and/or mANGPTL4 (1-183), mANGPTL4 (23-183), mANGPTL4 (1 to about 165), mANGPTL4(23 to about 165), mANGPTL4 (23-410) or mANGPTL4 (184-410) amino acid subsequence of the murine ANGPTL4. Other subsequences also include, but not limited to, e.g., 40-183 (SEQ ID NO: 15), 60-183 (SEQ ID NO: 16), 80-183 (SEQ ID NO: 17), 100-183 (SEQ ID NO: 18), 120-183 (SEQ ID NO: 19), 140-183 (SEQ ID NO: 20), 40-406 (SEQ ID NO: 21), 60-406 (SEQ ID NO: 22), 80-406 (SEQ ID NO: 23), 100-406 (SEQ ID NO: 24), 120-406 (SEQ ID NO: 25), 140-406 (SEQ ID NO: 26), and 160-406 (SEQ ID NO: 27) of hANGPTL4 and, e.g., 40-183, 60-183, 80-183, 100-183, 120-183, 140-183, 40-410, 60-410, 80-410, 100-410, 120-410, 140-410 and 160-410 of mANGPTL4. Agonists ANGPTL4 include molecules that activate ANGPTL4 or produce ANGPTL4 activities, e.g., active polypeptides, small molecules, and molecules that increase activity or expression of ANGPTL4. ANGPTL4 agonists also include $\alpha_v\beta_5$ agonists.

ANGPTL4 antagonists of the invention are molecules that inhibit or reduce the activity of ANGPTL4. An ANGPTL4 inhibitor can include a small molecular weight substance, an polynucleotide, antisense molecules, RNA aptamers, ribozymes against ANGPTL4 or its receptor polypeptides, an polypeptide, antagonist variants of ANGPTL4, an isolated protein, a recombinant protein, an antibody, or conjugates or fusion proteins thereof, that inhibits an ANGPTL4 activity, directly or indirectly. In certain embodiments of the invention, an antagonist ANGPTL4 antibody is an antibody that inhibits or reduces the activity of ANGPTL4 by binding to a specific subsequence or region of the ANGPTL4 protein, e.g., N-terminal, N-terminal coiled-coil domain, C-terminal, C-terminal fibrinogen-like domain, or ANGPTL4 (1-183) (SEQ ID NO: 10), ANGPTL4 (23-183) (SEQ ID NO: 11), ANGPTL4 (1 to about 162) (SEQ ID NO: 12), ANGPTL4 (about 162-406) (SEQ ID NO: 13), ANGPTL4 (23-406) (SEQ ID NO: 8), or ANGPTL4 (184-406) (SEQ ID NO: 14) amino acid subsequence of human ANGPTL4, and/or mANGPTL4 (1-183), mANGPTL4 (23-183), mANGPTL4 (1 to about 165), mANGPTL4(23 to about 165), mANGPTL4 (23-410) or mANGPTL4 (184-410) amino acid subsequence of the murine ANGPTL4. Other subsequences also include, but are not limited to, e.g., 40-183 (SEQ ID NO: 15), 60-183 (SEQ ID NO: 16), 80-183 (SEQ ID NO: 17), 100-183 (SEQ ID NO: 18), 120-183 (SEQ ID NO: 19), 140-183 (SEQ ID NO: 20), 40-406 (SEQ ID NO: 21), 60-406 (SEQ ID NO: 22), 80-406 (SEQ ID NO: n, 100-406 (SEQ ID NO: 24), 120-406 (SEQ ID NO: 25), 140-406 (SEQ ID NO: 26), and 160-406 (SEQ ID NO: 27) of hANGPTL4 and, e.g., 40-183, 60-183, 80-183, 100-183, 120-183, 140-183, 40-410, 60-410, 80-410, 100-410, 120-410, 140-410 and 160-410 of mANGPTL4. In certain embodiments of the invention, an antagonist of ANGPTL4 includes an anti-$\alpha_v\beta_5$ antibody, e.g., an antagonist anti-$\alpha_v\beta_5$ antibody. In certain embodiments, the antibodies of the invention are humanized antibodies. In certain embodiments of the invention, an ANGPTL4 antagonist is a SiRNA molecule. In one embodiment, the SiRNA molecule is an ANGPTL4-SiRNA molecule, where the molecule targets a DNA sequence (e.g., GTGGCCAAGCCTGC-CCGAAGA (SEQ ID NO: 3)) of a nucleic acid encoding ANGPTL4. An immunoadhesin of ANGPTL4 comprises at least the receptor-binding region of ANGPTL4 fused to an immunoglobulin sequence. In certain embodiments, ANGPTL4, agonist or antagonist is with a carrier, e.g., a pharmaceutically acceptable carrier.

ANGPTL4 transgenic and knockout animals are described and uses of these transgenic animals are also provided. The invention also provides an isolated cell derived from a non human transgenic animal whose genome comprises a disruption of a gene which encodes for an ANGPTL4. In certain embodiments, the isolated cell comprises a murine cell (e.g., an embryonic stem cell).

Mutated gene disruptions of ANGPTL4 have resulted in phenotypic observations related to various disease conditions or dysfunctions including: cardiovascular, endothelial or angiogenic disorders including atherosclerosis; abnormal metabolic disorders including lipid homeostasis disorders; or immunological and inflammatory disorders. Methods of the invention include treating a cardiovascular, endothelial or angiogenic disorder; abnormal metabolic disorder, immunological disorder; a lipid homeostasis disorder, or oncological disorder associated with the disruption of a gene which encodes for an ANGPTL4 or associated with an ANGPTL4 activity by administering to a subject an effective amount of an ANGPTL4, an agonist or antagonist of an ANGPTL4, thereby effectively treating said disorder or disease.

Methods of identifying a phenotype associated with a disruption of a gene which encodes for an ANGPTL4 are also provided. For example, the method includes (a) measuring a physiological characteristic of a non human transgenic animal whose genome comprises a disruption of a gene which encodes for an ANGPTL4; and (b) comparing the measured physiological characteristic with that of a gender matched wild type animal. A phenotype resulting from the gene disruption is identified as the physiological characteristic of the non human transgenic animal that differs from the physiological characteristic of the wild type animal. The non-human transgenic animal can be homozygous or heterozygous for the disruption of a gene which encodes for an ANGPTL4.

Methods for identifying an agent that modulates a phenotype associated with a disruption of a gene that encodes for an ANGPTL4 are also provided. For example, a method includes (a) measuring a physiological characteristic of a non human transgenic animal whose genome comprises a disruption of the gene which encodes for the ANGPTL4; and (b) comparing the measured physiological characteristic of (a) with that of a gender matched wild type animal. A phenotype resulting from the gene disruption in the non human transgenic animal is a physiological characteristic of the non human transgenic animal that differs from the physiological characteristic of the wild type animal. A test agent is administered to the non human transgenic animal of (a); and, it is determined whether the test agent modulates the identified phenotype associated with gene disruption. A test agent that modulates the phenotype is an agent that modulates that phenotype.

In certain embodiments, a phenotype associated with the ANGPTL4 gene disruption or phenotype exhibited by the non human transgenic animal as compared with gender matched wild type littermates is at least one of the following, but is not limited to, e.g., a cardiovascular, endothelial or angiogenic disorder; an immunological disorder; a lipid homeostasis disorder; or an abnormal metabolic disorder.

Methods of identifying an agent that modulates a physiological characteristic associated with a disruption of the gene which encodes for an ANGPTL4 are also provided. In certain embodiments, the method includes (a) measuring a physiological characteristic exhibited by a non human transgenic animal whose genome comprises a disruption of the gene which encodes for an ANGPTL4; and (b) comparing the measured physiological characteristic of (a) with that of a gender matched wild type animal. A physiological characteristic exhibited by the non human transgenic animal that differs from the physiological characteristic exhibited by the wild type animal is identified as a physiological characteristic associated with gene disruption. A test agent is administered to the non human transgenic animal of (a); and, it is determined whether the physiological characteristic associated with gene disruption is modulated. A test agent that modulates the physiological characteristics is an agent that modulates that characteristic.

In certain embodiments, the non human transgenic animal exhibits at least one of the following physiological characteristics compared with gender matched wildtype littermates, e.g., a modulation in mean serum cholesterol levels, a modulation in mean serum triglyceride levels, a modulation in a glucose tolerance test, a modulation in glucose homeostasis, a decreased mean serum glucose level; an increased mean serum insulin level; a decreased mean serum insulin level; an increased mean serum IgM level and increased mean absolute neutrophil count, an increased mean percent body fat; a decreased body weight and length, decreased total tissue mass and lean body mass, decreased total fat mass, growth retardation with decreased body weight and length, and/or decreased mean percent of total body fat, total tissue mass. In one embodiment, the modulation in the mean serum cholesterol levels is a decreased mean serum cholesterol level. In one embodiment, the modulation in the mean serum triglyceride level is a decrease mean serum triglyceride level. In another embodiment, the modulation in the glucose tolerance test is an enhanced glucose tolerance.

Methods of identifying an agent that ameliorates a cardiovascular, endothelial or angiogenic disorder; an immunological disorder; an oncological disorder; a lipid metabolic disorder; or an abnormal metabolic disorder associated with a disruption in the gene which encodes for an ANGPTL4 are provided. For example, a method includes (a) administering a test agent to a non human transgenic animal comprising a disruption in an ANGPTL4 gene; and (b) determining whether the test agent ameliorates the cardiovascular, endothelial or angiogenic disorder; immunological disorder; oncological disorder; lipid metabolic disorder; or metabolic disorder associated with the gene disruption in the non human transgenic animal.

The invention provides methods of evaluating a therapeutic agent capable of affecting a condition associated with a disruption of a gene that encodes for an ANGPTL4. For example, a method includes (a) measuring a physiological characteristic of a non human transgenic animal whose genome comprises a disruption of the gene which encodes for the ANGPTL4; (b) comparing the measured physiological characteristic of (a) with that of a gender matched wild type animal; (c) administering a test agent to the non human transgenic animal of (a); and, (d) evaluating the effects of the test agent on the identified condition associated with gene disruption in the non human transgenic animal. The physiological characteristic of the non human transgenic animal that differs from the physiological characteristic of the wild type animal is identified as a condition resulting from the gene disruption in the non human transgenic animal. For example, the condition is a cardiovascular, endothelial or angiogenic disorder; an immunological disorder; an oncological disorder; a lipid homeostasis disorder; or a metabolic disorder.

Methods of identifying an agent that modulates the expression of an ANGPTL4 are also provided. For example, a method includes (a) contacting a test agent with a host cell expressing an ANGPTL4; and (b) determining whether the test agent modulates the expression of the ANGPTL4 by the host cell.

An agent identified by any of above methods is also included in the invention. In one embodiment, the agent comprises an agonist. In another embodiment, the agent comprises an antagonist of an ANGPTL4. Agents that are therapeutic agents are also included in the invention along with a pharmaceutical composition including the therapeutic agent.

In various methods of the invention, a molecule of the invention, e.g., ANGPTL4, an agonist or antagonist of ANGPTL4, an agent, etc., can be administered to the subject through a systemic delivery system. In one aspect, the systemic delivery system includes a cell preparation comprising mammalian cells (e.g., CHO cells) expressing a recombinant form of the subject agent. In another aspect, the systemic delivery system can comprise a slow release preparation comprising purified agent and a polymer matrix. In certain embodiments, the molecule is administered to a subject with a pharmaceutically acceptable carrier. Alternatively, the molecule of the invention can be administered via a tissue-targeted (e.g., adipocytes, liver, etc.) gene delivery vector comprising a nucleic acid encoding the molecule. Well established viral or nonviral vectors for gene therapy can be used as the tissue-targeted gene delivery vector in the invention.

BRIEF DESCRIPTION OF THE FIGURES

FIG. 1 illustrate a nucleic acid sequence of human ANGPTL4 (SEQ ID NO:1).

FIG. 2 illustrates an amino acid sequence of human ANGPTL4 (SEQ ID NO:2) derived from the coding sequence of SEQ ID NO:1 shown in FIG. 1.

FIG. 3, Panel A illustrates purified recombinant murine ANGPTL4 (23-410) separated on SDS polyacrylamide gel electrophoresis (SDS-PAGE) (4-20%) in the presence (10 mM) or absence of dithiothreitol (DTT). FIG. 3, Panel B illustrates wild type (lane 1) and variant hANGPTL4 (lane 2) separated on a SDS gel and detected by western blotting, where the variant hANGPTL4 has a R162G and R164E substitution (SEQ ID NO: 28).

FIG. 4 schematically illustrates ANGPTL4 induces cell-adhesion of human hepatocytes.

FIG. 5 schematically illustrates ANGPTL4 induces hepatocyte proliferation.

FIG. 6, Panels A and B schematically illustrate extracellular ANGPTL4 induces primary human pre-adipocyte visceral proliferation (Panel A) and pre-adipocyte subcutaneous proliferation (Panel B).

FIG. 7 schematically illustrates ANGPTL4 (23-406) (SEQ ID NO: 8) and IgG-chimera human ANGPTL4 forms bind to subcutaneous primary human adipocytes by FACS analysis.

FIG. 8, Panels A, B and C illustrate that ANGPTL4 induces cell migration of primary human pre-adipocytes, subcutaneous. Panels A and B illustrate ANGPTL4 induces cell migration of primary pre-adipocytes overnight (Panel A) and 7 hours (Panel B). Panel C schematically illustrates migration of primary pre-adipocytes with ANGPTL4 at 7 hours, where (1) is no serum added, (2) is 10% fetal calf serum (FCS), (3) is PDGF-BB, and (4) mANGPTL4.

FIG. 9, Panels A, B, C, D and E illustrate binding of ANGPTL4 to integrin $\alpha_v\beta_5$. Panel A illustrates the adhesion of 293-1953 ($\alpha_v\beta_5$) cells to a plate coated with either mANGPTL4 or vitronectin at the concentration indicated at the bottom in (μg/ml), where BSA is used as a control. Panel B illustrates that anti-$\alpha_v\beta_5$ and anti-hANGPTL4 antibodies abolishes ANGPTL4 cell adhesion activity, where (1) is BSA, (2) is vitronectin and (3) is mANGPTL4. Panel C illustrates binding of protein (mANGPTL4, hANGPTL4-N$_{terminal}$, or hANGPTL4-C$_{terminal}$) using the amount indicated to $\alpha_v\beta_5$ coated plates. Panel D illustrates inhibition of binding of protein (mANGPTL4, hANGPTL4-N$_{terminal}$, or hANGPTL4-C$_{terminal}$) to $\alpha_v\beta_5$ coated plates with anti-hANGPTL4, where anti-down syndrome critical region 1 protein (Dscr) antibody control, 5G7 or medium are used as controls. Panel E illustrates binding of ANGPTL4 and $\alpha_v\beta_5$, where (1) is hANGPTL4-Cterminal coated on the plate, (2) is hANGPTL4-Cterminal coated on plate and incubated with anti-hANGPTL4, (3) is hANGPTL4-Cterminal coated on the plate and incubated anti-Dscr, (4) is Vitronectin coated on the plate and (5) is BSA coated on the plate, before adding $\alpha_v\beta_5$.

FIG. 10 illustrates triglyceride levels of mice with intravenous tail injection of ANGPTL4 and variants of ANGPTL4, where (1) is Ad-GFP, (2) is Ad-Gd, (3) is ANGPTL4 (1-406) (SEQ ID NO: 2), (4) ANGPTL4(1-183) (SEQ ID NO: 10), (5) is ANGPTL4(184-406) (SEQ ID NO: 14), (6) is ANGPTL4 variant R162G and R164E (SEQ ID NO: 28), (7) is ANGPTL4 (1-408) and (8) is a control.

DETAILED DESCRIPTION

Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like. Unless defined otherwise, all scientific and technical terms are understood to have the same meaning as commonly used in the art to which they pertain. For the purpose of the invention, the following terms are defined below.

The term "ANGPTL4 or "Angptl4" refers to angiopoietin-like 4 polypeptide or protein, along with naturally occurring allelic, secreted, and processed forms thereof. For example, ANGPTL4 from human is a 406 amino acid protein, while the mouse ANGPTL4 is a 410 amino acid protein. The term "ANGPTL4" is also used to refer to fragments (e.g., subsequences, truncated forms, etc.) of the polypeptide comprising, e.g., N-terminal fragment, Coiled-coil domain, C-terminal fragment, fibrinogen-like domain, amino acids 1-183 (SEQ ID NO: 10), 23-183 (SEQ ID NO: 11), 1 to about 162 (SEQ ID NO: 12), 23 to about 162 (SEQ ID NO: 29), 23-406 (SEQ ID NO: 8), 184-406 (SEQ ID NO: 14), about 162-406 (SEQ ID NO: 13), or 23-184 (SEQ ID NO: 30) of the human angiopoietin-like 4 protein, and amino acids 1-183, 23-183, 1 to about 165, 23 to about 165, 23-410, or 184-410 of the murine angiopoietin-like 4 protein. Other fragments include but are not limited to, e.g., 40-183 (SEQ ID NO: 15), 60-183 (SEQ ID NO: 16), 80-183 (SEQ ID NO: 17), 100-183 (SEQ ID NO: 18), 120-183 (SEQ ID NO: 19), 140-183 (SEQ ID NO: 20), 40-406 (SEQ ID NO: 21), 60-406 (SEQ ID NO: 22), 80-406 (SEQ ID NO: 23), 100-406 (SEQ ID NO: 24), 120-406 (SEQ ID NO: 25), 140-406 (SEQ ID NO: 26), and 160-406 (SEQ ID NO: 27) of hANGPTL4 and, e.g., 40-183, 60-183, 80-183, 100-183, 120-183, 140-183, 40-410, 60-410, 80-410, 100-410, 120-410, 140-410 and 160-410 of mANGPTL4. Reference to any such forms of ANGPTL4 can also be identified in the application, e.g., by "ANGPTL4 (23-406) (SEQ ID NO: 8)," "ANGPTL4 (184-406) (SEQ ID NO: 14)," "ANGPTL4 (23-183) (SEQ ID NO: 11)," "mANGPTL4 (23-410)," "mANGPTL4 (184-410)," etc., where m indicates murine sequence. The amino acid position for a fragment native ANGPTL4 are numbered as indicated in the native ANGPTL4 sequence. For example, amino acid position 22(Ser) in a fragment ANGPTL4 is also position 22(Ser) in native human ANGPTL4, e.g., see FIG. 2. Generally, the fragment native ANGPTL4 has biological activity.

A "native sequence" polypeptide comprises a polypeptide having the same amino acid sequence as a polypeptide derived from nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (e.g., an extracellular domain sequence), naturally occurring variant forms (e.g., alternatively spliced forms) and naturally occurring allelic variants of the polypeptide.

A polypeptide "variant" means a biologically active polypeptide having at least about 80% amino acid sequence identity with the corresponding native sequence polypeptide, or fragment thereof. Such variants include, for instance, polypeptides wherein one or more amino acid residues are added, or deleted, at the N- and/or C-terminus of the polypeptide. Ordinarily, a variant will have at least about 80% amino acid sequence identity, or at least about 90% amino acid sequence identity, or at least about 95% or more amino acid sequence identity with the native sequence polypeptide, or fragment thereof.

The term "ANGPTL4 variant" as used herein refers to a variant as described above and/or an ANGPTL4 which includes one or more amino acid mutations in the native ANGPTL4 sequence. Optionally, the one or more amino acid mutations include amino acid substitution(s). ANGPTL4 and variants thereof for use in the invention can be prepared by a variety of methods well known in the art. Amino acid sequence variants of ANGPTL4 can be prepared by mutations in the ANGPTL4 DNA. Such variants include, for example, deletions from, insertions into or substitutions of residues within the amino acid sequence of ANGPTL4, e.g., a human amino acid sequence encoded by the nucleic acid deposited under ATCC deposit number 209284, or as shown in FIG. 2. Any combination of deletion, insertion, and substitution may be made to arrive at the final construct having the desired activity. The mutations that will be made in the DNA encoding the variant must not place the sequence out of reading frame and preferably will not create complementary regions that could produce secondary mRNA structure. EP 75,444A.

The ANGPTL4 variants optionally are prepared by site-directed mutagenesis of nucleotides in the DNA encoding the native ANGPTL4 or phage display techniques, thereby producing DNA encoding the variant, and thereafter expressing the DNA in recombinant cell culture.

While the site for introducing an amino acid sequence variation is predetermined, the mutation per se need not be predetermined. For example, to optimize the performance of a mutation at a given site, random mutagenesis may be conducted at the target codon or region and the expressed ANGPTL4 variants screened for the optimal combination of desired activity. Techniques for making substitution mutations at predetermined sites in DNA having a known sequence are well-known, such as, for example, site-specific mutagenesis. Preparation of the ANGPTL4 variants described herein can be achieved by phage display techniques, such as those described in the PCT publication WO 00/63380.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, optionally 1 to 10 residues, optionally 1 to 5 or less, and typically are contiguous.

Amino acid sequence insertions include amino- and/or carboxyl-terminal fusions of from one residue to polypeptides of essentially unrestricted length as well as intrasequence insertions of single or multiple amino acid residues. Intrasequence insertions (i.e., insertions within the native ANGPTL4 sequence) may range generally from about 1 to 10 residues, optionally 1 to 5, or optionally 1 to 3. An example of a terminal insertion includes a fusion of a signal sequence, whether heterologous or homologous to the host cell, to the N-terminus to facilitate the secretion from recombinant hosts.

Additional ANGPTL4 variants are those in which at least one amino acid residue in the native ANGPTL4 has been removed and a different residue inserted in its place. In one embodiment of the invention, ANGPTL4 variant includes a substitution at 162 and/or 164 of ANGPTL4 or a substitution at 169 of mANGPTL4. Such substitutions may be made in accordance with those shown in Table 1. ANGPTL4 variants can also comprise unnatural amino acids as described herein.

Amino acids may be grouped according to similarities in the properties of their side chains (in A. L. Lehninger, in *Biochemistry*, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

"Naturally occurring amino acid residues" (i.e. amino acid residues encoded by the genetic code) may be selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include, e.g., norleucine, ornithine, norvaline, homoserine and other amino acid residue analogues such as those described in Ellman et al. *Meth. Enzym.* 202:301-336 (1991) & US Patent application publications 20030108885 and 20030082575. Briefly, these procedures involve activating a suppressor tRNA with a non-naturally occurring amino acid residue followed by in vitro or in vivo transcription and translation of the RNA. See, e.g., US Patent application publications 20030108885 and 20030082575; Noren et al. *Science* 244:182 (1989); and, Ellman et al., supra.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, e.g., digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In certain embodiments, the polypeptide will be purified (1) to greater than 95% by weight of polypeptide as determined by the Lowry method, or more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue, or silver stain. Isolated polypeptide includes the polypeptide in situ within recombinant cells since at least one component of the polypeptide's natural environment will not be present. Ordinarily, however, isolated polypeptide will be prepared by at least one purification step.

The term "ANGPTL4 modulator" refers to a molecule that can activate, e.g., an agonist, ANGPTL4 or its expression, or that can inhibit, e.g., an antagonist (or inhibitor), the activity of ANGPTL4 or its expression. ANGPTL4 agonists include antibodies and active fragments. An ANGPTL4 antagonist refers to a molecule capable of neutralizing, blocking, inhibiting, abrogating, reducing or interfering with ANGPTL4 activities, e.g., cell proliferation or growth, migration, adhesion or metabolic, e.g., lipid, modulation, or its expression including its binding to an ANGPTL4 receptor, e.g., $\alpha_v\beta_5$. ANGPTL4 antagonists include, e.g., anti-ANGPTL4 antibodies and antigen-binding fragments thereof, receptor molecules and derivatives which bind specifically to ANGPTL4 thereby sequestering its binding to one or more receptors, anti-ANGPTL4 receptor antibodies and ANGPTL4 receptor antagonists such as small molecule inhibitors of the receptor. Other ANGPTL4 antagonists also include antagonist variants of ANGPTL4, antisense molecules (e.g., ANGPTL4—SiRNA), RNA aptamers, and ribozymes against ANGPTL4 or its receptor. In certain embodiments, antagonist ANGPTL4 antibodies are antibodies that inhibit or reduce the activity of ANGPTL4 by binding to a specific subsequence or region of ANGPTL4, e.g., N-terminal fragment, Coiled-coil domain, C-terminal fragment, fibrinogen-like domain, amino acids 1-183 (SEQ ID NO: 10), 23-183 (SEQ ID NO: 11), 1 to about 162 (SEQ ID NO: 12), 23 to about 162 (SEQ ID NO: 29), 23-406 (SEQ ID NO: 8), 184-406 (SEQ ID NO: 14), about 162-406 (SEQ ID NO: 13) or 23-184 (SEQ ID NO: 30) of the human angiopoietin-like 4 protein, and amino acids 1-183, 23-183, 1 to about 165, 23 to about 165, 23-410, or 184-410 of the murine angiopoietin-like 4 protein. Other subsequences also include, but not limited to, e.g., 40-183 (SEQ ID NO: 15), 60-183 (SEQ ID NO: 16), 80-183 (SEQ ID NO: 17), 100-183 (SEQ ID NO: 18), 120-183 (SEQ ID NO: 19), 140-183 (SEQ ID NO: 20), 40-406 (SEQ ID NO: 21), 60-406 (SEQ ID NO: 22), 80-406 (SEQ ID NO: 23), 100-406 (SEQ ID NO: 24), 120-406 (SEQ ID NO: 25), 140-406 (SEQ ID NO: 26), and 160-406 (SEQ ID NO: 27) of hANGPTL4 and, e.g., 40-183, 60-183, 80-183, 100-183, 120-183, 140-183, 40-410, 60-410, 80-410, 100-410, 120-410, 140-410 and 160-410 of mANGPTL4.

Modulators of ANGPTL4 are molecules that modulate the activity of ANGPTL4, e.g., agonists and antagonists. The term "agonist" is used to refer to peptide and non-peptide analogs of ANGPTL4, and to antibodies specifically binding such ANGPTL4 molecules, provided they have the ability to signal through a native ANGPTL4 receptor (e.g., $\alpha_v\beta_5$ integrin). The term "agonist" is defined in the context of the biological role of an ANGPTL4 receptor (e.g., $\alpha_v\beta_5$). In certain embodiments, agonists possess the biological activities of a native ANGPTL4, as defined above, such as the promotion of proliferation, migration, and/or adhesion of cells, and/or modulation of lipid homeostasis.

The term "antagonist" is used to refer to molecules that have the ability to inhibit the biological activity of ANGPTL4 regardless of whether they have the ability to bind ANGPTL4 or its receptor, e.g., $\alpha_v\beta_5$. For example, antagonists that have the ability to bind ANGPTL4 or its receptor include anti-ANGPTL4 and anti-$\alpha_v\beta_5$ antibodies. Antagonist that inhibit expression of ANGPTL4 are included, e.g., ANGPTL4-SiRNA. Antagonist ANGPTL4 can be assessed by, e.g., by inhibiting the activity of ANGPTL4, e.g., adhesion, migration, proliferation, and/or modulation of lipid homeostasis activity of ANGPTL4. With regard to $\alpha_v\beta_5$ integrin receptor activity, a modulator of an $\alpha_v\beta_5$ integrin receptor can be determined by methods known in the art. For example, the method described by J. W. Smith et al. in *J. Biol. Chem.* 265:12267-12271 (1990) can be used.

The term "Anti-ANGPTL4 antibody" is an antibody that binds to ANGPTL4 with sufficient affinity and specificity. In certain embodiments of the invention, the anti-ANGPTL4 antibody of the invention can be used as a therapeutic agent in targeting and interfering with diseases or conditions wherein ANGPTL4 activity is involved. Generally, an anti-ANGPTL4 antibody will usually not bind to other ANGPTL4 homologues, e.g., ANGPTL3.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments (see below) so long as they exhibit the desired biological activity.

Unless indicated otherwise, the expression "multivalent antibody" is used throughout this specification to denote an antibody comprising three or more antigen binding sites. The multivalent antibody is typically engineered to have the three or more antigen binding sites and is generally not a native sequence IgM or IgA antibody.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., *Nature* 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g. single chain Fv; scFv) (Bird et al., *Science* 242:423-426 (1988); and Huston et al., *PNAS* (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., *Proc. Natl. Acad. Sci. USA*, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. *Protein Eng.* 8(10):1057 1062 (1995); and U.S. Pat. No. 5,641,870).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) or Marks et al., *J. Mol. Biol.* 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. *Nature Biotechnology* 14:309-314 (1996): Sheets et al. *PNAS (USA)* 95:6157-6162 (1998)); Hoogenboom and Winter, *J. Mol. Biol.*, 227:381 (1991); Marks et al., *J. Mol. Biol.*, 222:581

(1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., *Bio/Technology* 10: 779-783 (1992); Lonberg et al., *Nature* 368: 856-859 (1994); Morrison, *Nature* 368:812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody-dependent cell-mediated cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., $IgG_1$ (including non-A and A allotypes), $IgG_2$, $IgG_3$, $IgG_4$, IgA, and $IgA_2$. The heavy-chain constant domains that correspond to the different classes of antibodies are called α, δ, ε, γ and respectively. The subunit structures and three-dimensional configurations of different classes of immunoglobulins are well known.

The light chains of antibodies from any vertebrate species can be assigned to one of two clearly distinct types, called kappa (6) and lambda (8), based on the amino acid sequences of their constant domains.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

The "CH2 domain" of a human IgG Fc region (also referred to as "Cg2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protroberance" in one chain thereof and a corresponding introduced "cavity" in the other chain thereof; see U.S. Pat. No. 5,821,333, expressly incorporated herein by reference). Such variant CH3 domains may be used to make multispecific (e.g. bispecific) antibodies as herein described.

"Hinge region" is generally defined as stretching from about Glu216, or about Cys226, to about Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor;

BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature.

A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will typically possess, e.g., at least about 80% sequence identity with a native sequence Fc region and/or with an Fc region of a parent polypeptide, or at least about 90% sequence identity therewith, or at least about 95% sequence or more identity therewith.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Typically, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being generally preferred. The effector cells may be isolated from a native source thereof, e.g. from blood or PBMCs as described herein.

The terms "Fc receptor" and "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976); and Kim et al., *J. Immunol.* 24:249 (1994)).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

The term "immunoadhesin" refers to antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as $IgG_1$, $IgG_2$, $IgG_3$, or $IgG_4$ subtypes, IgA (including $IgA_1$ and $IgA_2$), IgE, IgD or IgM.

"Active" or "activity" for the purposes herein refers to form(s) of ANGPTL4 which retain a biological and/or an immunological activity of native or naturally-occurring ANGPTL4, wherein "biological" activity refers to a biological function (either inhibitory or stimulatory) caused by a native or naturally-occurring ANGPTL4 other than the ability to induce the production of an antibody against an antigenic epitope possessed by a native or naturally-occurring ANGPTL4 and an "immunological" activity refers to the ability to induce the production of an antibody against an antigenic epitope possessed by a native or naturally-occurring ANGPTL4.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For the multimeric antibodies herein, the number of functional antigen binding sites can be evaluated using ultracentrifugation analysis. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

An antibody having a "biological characteristic" of a designated antibody is one which possesses one or more of the biological characteristics of that antibody which distinguish it from other antibodies that bind to the same antigen. In order to screen for antibodies which bind to an epitope on an antigen bound by an antibody of interest, a routine cross-blocking assay such as that described in *Antibodies, A Laboratory Manual*, Cold Spring Harbor Laboratory, Ed Harlow and David Lane (1988), can be performed.

A "polypeptide chain" is a polypeptide wherein each of the domains thereof is joined to other domain(s) by peptide bond(s), as opposed to non-covalent interactions or disulfide bonds.

A "flexible linker" herein refers to a peptide comprising two or more amino acid residues joined by peptide bond(s), and provides more rotational freedom for two polypeptides (such as two Fd regions) linked thereby. Such rotational freedom allows two or more antigen binding sites joined by the flexible linker to each access target antigen(s) more efficiently. Examples of suitable flexible linker peptide sequences include gly-ser, gly-ser-gly-ser (SEQ ID NO: 6), ala-ser, and gly-gly-gly-ser (SEQ ID NO: 7).

A "dimerization domain" is formed by the association of at least two amino acid residues (generally cysteine residues) or of at least two peptides or polypeptides (which may have the same, or different, amino acid sequences). The peptides or polypeptides may interact with each other through covalent and/or non-covalent association(s). Examples of dimerization domains herein include an Fc region; a hinge region; a CH3 domain; a CH4 domain; a $CH_1$—CL pair; an "interface" with an engineered "knob" and/or "protruberance" as described in U.S. Pat. No. 5,821,333, expressly incorporated herein by reference; a leucine zipper (e.g. a jun/fos leucine zipper, see Kostelney et al., *J. Immunol.*, 148: 1547-1553 (1992); or a yeast GCN4 leucine zipper); an isoleucine zipper; a receptor dimer pair (e.g., interleukin-8 receptor (IL-8R); and integrin heterodimers such as LFA-1 and GPIIIb/IIIa), or the dimerization region(s) thereof; dimeric ligand polypeptides (e.g. nerve growth factor (NGF), neurotrophin-3 (NT-3), interleukin-8 (IL-8), vascular endothelial growth factor (VEGF), VEGF-C, VEGF-D, PDGF members, and brain-derived neurotrophic factor (BDNF); see Arakawa et al. *J. Biol. Chem.* 269(45): 27833-27839 (1994) and Radziejewski et al. *Biochem.* 32(48): 1350 (1993)), or the dimerization region(s) thereof; a pair of cysteine residues able to form a disulfide bond; a pair of peptides or polypeptides, each comprising at least one cysteine residue (e.g. from about one, two or three to about ten cysteine residues) such that disulfide bond(s) can form between the peptides or polypeptides (hereinafter "a synthetic hinge"); and antibody variable domains. The most preferred dimerization domain herein is an Fc region or a hinge region.

The phrase "stimulating proliferation of a cell" encompasses the step of increasing the extent of growth and/or reproduction of the cell relative to an untreated cell or a reduced treated cell either in vitro or in vivo. An increase in cell proliferation in cell culture can be detected by counting the number of cells before and after exposure to a molecule of interest. The extent of proliferation can be quantified via microscopic examination of the degree of confluence. Cell proliferation can also be quantified using assays known in the art, e.g., thymidine incorporation assay, and commercially available assays. The phrase "inhibiting proliferation of a cell" encompasses the step of decreasing the extent of growth and/or reproduction of the cell relative to an untreated cell or a reduced treated cell either in vitro or in vivo. It can be quantified as described above.

Administration "in combination with" one or more further therapeutic agents includes simultaneous (concurrent) and/or consecutive administration in any order.

"Subject" for purposes of treatment refers to any animal. Generally, the animal is a mammal. "Mammal" for purposes of treatment refers to any animal classified as a mammal, including humans, domestic and farm animals, and zoo, sports, or pet animals, such as dogs, horses, cats, cows, sheep, pigs, etc. Typically, the mammal is a human.

The term "ameliorates" or "amelioration" as used herein refers to a decrease, reduction or elimination of a condition, disease, disorder, or phenotype, including an abnormality or symptom.

A "disorder" is any condition that would benefit from treatment with a molecule of the invention. This includes chronic and acute disorders or diseases including those pathological conditions which predispose the subject to the disorder in question.

The term "effective amount" or "therapeutically effective amount" refers to an amount of a drug effective to treat a disease or disorder in a subject.

"Treatment" refers to both therapeutic treatment and prophylactic or preventative measures. Those in need of treatment include those already with the disorder as well as those in which the disorder is to be prevented.

"Hypertrophy," as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. For example, hypertrophic growth of adipocytes is an increase in size of the adipocyte stimulated by lipid accumulation. Hyperplastic growth of adipocytes is an increase in number of adipocytes in adipose tissue.

The phrases "cardiovascular and endothelial disorder," "cardiovascular and endothelial dysfunction" and "cardiovascular, endothelial or angiogenic disorder" are used interchangeably and refer to disorders, typically systemic, that stimulate angiogenesis and/or cardiovascularization. This includes diseases that affect vessels, as well as diseases of the vessels themselves, such as of the arteries, capillaries, veins, and/or lymphatics. Such disorders include, but are not limited to, e.g., arterial disease, such as atherosclerosis, diabetes mellitus, hypertension, inflammatory vasculitides, Reynaud's disease and Reynaud's phenomenon, aneurysms, and arterial restenosis; venous and lymphatic disorders such as thrombophlebitis, lymphangitis, and lymphedema; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; and other vascular disorders such as peripheral vascular disease, trauma such as wounds, burns, and other injured tissue, implant fixation, scarring, ischemia reperfusion injury, rheumatoid arthritis, cerebrovascular disease, renal diseases such as acute renal failure; stroke, coronary artery disease, hypercholesterolemia, hypertriglyceridemia, and/or osteoporosis. This would also include angina, myocardial infarctions such as acute myocardial infarctions, cardiac hypertrophy, and heart failure such as congestive heart failure (CHF). Cardiovascular diseases associated with dyslipidemia are also included, e.g., but not limited to, hypertension, atherosclerosis, heart failure, stroke, various coronary artery diseases, obesity, diabetes, etc.

The term a "lipid homeostasis disorder" includes a disorder, disease, or condition associated with, caused by, and/or linked to abnormal regulation (e.g., upregulation or downregulation) of lipid metabolism. Lipid homeostasis disorders may be caused by or associated with aberrant lipolysis, aberrant lipid uptake, aberrant lipid synthesis and/or secretion, aberrant intracellular lipid release and/or turnover, aberrant intracellular triglyceride release and/or turnover, aberrant intracellular lipid and/or triglyceride mass, and/or aberrant secreted lipid and/or triglyceride mass within or from a cell, e.g., a liver cell. Lipid homeostasis disorders include, but are not limited to, atherosclerosis, obesity, conditions related to obesity, diabetes, insulin resistance, hyperlipidemia, hypolipidemia, dyslipidemia, hypercholesterolemia, hypocholesterolemia, triglyceride storage disease, cardiovascular disease, coronary artery disease, hypertension, stroke, overweight, anorexia, cachexia, hyperlipoproteinemia, hypolipoproteinemia, Niemann Pick disease, hypertriglyceridemia, hypotriglyceridemia, pancreatitis, diffuse idiopathic skeletal hyperostosis (DISH), atherogenic lipoprotein phenotype (ALP), epilepsy, liver disease, fatty liver, steatohepatitis, polycystic ovarian syndrome, cancer, etc. The term "lipid metabolic disorder" refers to abnormal clinical chemistry levels of cholesterol and triglycerides. The term "Hyperlipidemia" or "Hyperlipemia" refers to a condition where there are higher levels than normal of serum lipid levels. Serum lipids include cholesterol (ester and free), lipoproteins, triglycerides, free fatty acids, and other sterols. In one aspect, elevated levels of these lipids are an indication for atherosclerosis.

The term "Obesity" refers to a condition whereby a mammal has a Body Mass Index (BMI), which is calculated as weight (kg) per height$^2$ (meters$^2$), of at least 25.9. Conventionally, those persons with normal weight have a BMI of 19.9 to less than 25.9. The obesity herein may be due to any cause, whether genetic or environmental. Examples of disorders that may result in obesity or be the cause of obesity include, e.g., but are not limited to, overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. An "obesity-determining property" includes fat cells and tissue, such as fat pads, total body weight, triglyceride levels in muscle, liver and fat and fasting and non-fasting levels of leptin, free fatty acids and triglycerides in the blood.

The term "Conditions related to obesity" refer to conditions which are the result of or which are exasperated by obesity, such as, but not limited to dermatological disorders such as infections, varicose veins, *Acanthosis nigricans*, and eczema, exercise intolerance, diabetes mellitus, insulin resistance, hypertension, hypercholesterolemia, cholelithiasis, osteoarthritis, orthopedic injury, thromboembolic disease, cancer (e.g., breast cancer, colon cancer, prostate cancer, etc.), and coronary (or cardiovascular) heart disease, particular those cardiovascular conditions associated with high triglycerides and free fatty acids in a subject.

Obesity represents the most prevalent of body weight disorders, affecting an estimated 30 to 50% of the middle-aged population in the western world. Other body weight disorders, such as anorexia nervosa and bulimia nervosa, which together affect approximately 0.2% of the female population of the western world, also pose serious health threats. Further, such disorders as anorexia and cachexia (wasting) are also prominent features of other diseases such as cancer, cystic fibrosis, and AIDS.

The term "wasting" disorders (e.g., wasting syndrome, cachexia, sarcopenia) refers to a disorder caused by undesirable and/or unhealthy loss of weight or loss of body cell mass. In the elderly as well as in AIDS and cancer patients, wasting disease can result in undesired loss of body weight, including both the fat and the fat-free compartments. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, extraintestinal Crohn's disease, psychogenic disease, chronic heart failure or other severe trauma, frequently suffer from wasting disease which is sometimes also referred to as cachexia, a metabolic and, sometimes, an eating disorder. Cachexia is additionally characterized by hypermetabolism and hypercatabolism. Although cachexia and wasting disease are frequently used interchangeably to refer to wasting conditions, there is at least one body of research which differentiates cachexia from wasting syndrome as a loss of fat-free mass, and particularly, body cell mass (Mayer, 1999, *J. Nutr.* 129(1S Suppl.):256S-259S). Sarcopenia, yet another such disorder which can affect the aging individual, is typically characterized by loss of muscle mass. End stage wasting disease as described above can develop in individuals suffering from either cachexia or sarcopenia.

Diabetes is a chronic disorder affecting carbohydrate, fat and protein metabolism in animals. Diabetes is the leading cause of blindness, renal failure, and lower limb amputations in adults and is a major risk factor for cardiovascular disease and stroke.

Type I diabetes mellitus (or insulin-dependent diabetes mellitus ("IDDM") or juvenile-onset diabetes) comprises approximately 10% of all diabetes cases. The disease is characterized by a progressive loss of insulin secretory function by beta cells of the pancreas. This characteristic is also shared by non-idiopathic, or "secondary", diabetes having its origins in pancreatic disease. Type I diabetes mellitus is associated with the following clinical signs or symptoms, e.g., persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Type II diabetes mellitus (non-insulin-dependent diabetes mellitus or NIDDM) is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from type II diabetes mellitus have a relative insulin deficiency—that is, patients have lower than predicted insulin levels for a given plasma glucose concentration. Type II diabetes mellitus is characterized by the following clinical signs or symptoms, e.g., persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Syndrome X, also termed Insulin Resistance Syndrome (IRS), Metabolic Syndrome, or Metabolic Syndrome X, is recognized in some 2% of diagnostic coronary catheterizations. Often disabling, it presents symptoms or risk factors for the development of Type II diabetes mellitus and cardiovascular disease, including, e.g., impaired glucose tolerance (IGT), impaired fasting glucose (IFG), hyperinsulinemia, insulin resistance, dyslipidemia (e.g., high triglycerides, low HDL), hypertension and obesity.

An immunological disorders include, but is not limited to, e.g., systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barr syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonias, idiopathic pulmonary fibrosis and hypersensitivity pneumonitis; and/or transplantation associated diseases including graft rejection and graft-versus-host disease. Other disorders can be present, such as a developmental disorder (e.g., embryonic lethality), a neurological disorder (e.g., a decreased anxiety like response during open field activity testing, an abnormal circadian rhythm during home cage activity testing, etc.) an eye abnormality (e.g., a retinal abnormality); and/or a bone metabolic abnormality or disorder (e.g., arthritis, osteoporosis, and/or osteopetrosis).

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "gene" refers to (a) a gene containing a DNA sequence encoding ANGPTL4, e.g., ATCC deposit number 209284, or see FIG. 1; (b) any DNA sequence that encodes an ANGPTL4 amino acid sequence (see, e.g., FIG. 2), and/or; (c) any DNA sequence that hybridizes to the complement of the coding sequences disclosed herein. In certain embodiments, the term includes coding as well as noncoding regions, and preferably includes all sequences necessary for normal gene expression.

The term "gene targeting" refers to a type of homologous recombination that occurs when a fragment of genomic DNA is introduced into a mammalian cell and that fragment locates and recombines with endogenous homologous sequences. Gene targeting by homologous recombination employs recombinant DNA technologies to replace specific genomic sequences with exogenous DNA of particular design.

The term "homologous recombination" refers to the exchange of DNA fragments between two DNA molecules or chromatids at the site of homologous nucleotide sequences.

The term "target gene" (alternatively referred to as "target gene sequence" or "target DNA sequence") refers to any nucleic acid molecule, polynucleotide, or gene to be modified by homologous recombination. The target sequence includes an intact gene, an exon or intron, a regulatory sequence or any region between genes. The target gene may comprise a portion of a particular gene or genetic locus in the individual's genomic DNA.

"Disruption" of an ANGPTL4 gene occurs when a fragment of genomic DNA locates and recombines with an endogenous homologous sequence wherein the disruption is a deletion of the native gene or a portion thereof, or a mutation in the native gene or wherein the disruption is the functional inactivation of the native gene. Alternatively, sequence disruptions may be generated by nonspecific insertional inactivation using a gene trap vector (i.e. non-human transgenic animals containing and expressing a randomly inserted transgene; see for example U.S. Pat. No. 6,436,707 issued Aug. 20, 2002). These sequence disruptions or modifications may include insertions, missense, frameshift, deletion, or substitutions, or replacements of DNA sequence, or any combination thereof. Insertions include the insertion of entire genes, which may be of animal, plant, fungal, insect, prokaryotic, or viral origin. Disruption, for example, can alter the normal gene product by inhibiting its production partially or completely or by enhancing the normal gene product's activity. In one embodiment, the disruption is a null disruption, wherein there is no significant expression of the ANGPTL4 gene.

The term "native expression" refers to the expression of the full-length polypeptide encoded by the ANGPTL4 gene, at expression levels present in the wild-type mouse. Thus, a disruption in which there is "no native expression" of the endogenous ANGPTL4 gene refers to a partial or complete reduction of the expression of at least a portion of a polypeptide encoded by an endogenous ANGPTL4 gene of a single cell, selected cells, or all of the cells of a mammal.

The term "knockout" refers to the disruption of an ANGPTL4 gene wherein the disruption results in: the functional inactivation of the native gene; the deletion of the native gene or a portion thereof; or a mutation in the native gene.

The term "knock-in" refers to the replacement of the mouse ortholog (or other mouse gene) with a human cDNA encoding ANGPTL4-encoding genes or variants thereof (ie. the disruption results in a replacement of a native mouse gene with a native human gene).

The term "construct" refers to an artificially assembled DNA segment to be transferred into a target tissue, cell line or animal. Typically, the construct will include a gene or a nucleic acid sequence of particular interest, a marker gene and appropriate control sequences. As provided herein, a targeting ANGPTL4 construct includes a DNA sequence homologous to at least one portion of an ANGPTL4 gene and is capable of producing a disruption in an ANGPTL4 gene in a host cell.

The term "transgenic cell" refers to a cell containing within its genome an ANGPTL4 gene that has been disrupted, modified, altered, or replaced completely or partially by the method of gene targeting.

The term "transgenic animal" refers town animal that contains within its genome a specific gene that has been disrupted or otherwise modified or mutated by the methods described herein or methods otherwise well known in the art. In certain embodiments, the non-human transgenic animal is a mammal. In one embodiment, the mammal is a rodent such as a rat or mouse. In addition, a "transgenic animal" may be a heterozygous animal (i.e., one defective allele and one wild-type allele) or a homozygous animal (i.e., two defective alleles). An embryo is considered to fall within the definition of an animal. The provision of an animal includes the provision of an embryo or foetus in utero, whether by mating or otherwise, and whether or not the embryo goes to term.

As used herein, the terms "selective marker" and "position selection marker" refer to a gene encoding a product that enables only the cells that carry the gene to survive and/or grow under certain conditions. For example, plant and animal cells that express the introduced neomycin resistance (Neo$^r$) gene are resistant to the compound G418. Cells that do not carry the Neo$^r$ gene marker are killed by G418. Other positive selection markers are known to, or are within the purview of, those of ordinary skill in the art.

The term "modulates" or "modulation" as used herein refers to the decrease, inhibition, reduction, amelioration, increase or enhancement of an ANGPTL4 gene function, expression, activity, or alternatively a phenotype associated with ANGPTL4 gene.

The term "abnormality" refers to any disease, disorder, condition, or phenotype in which ANGPTL4 is implicated, including pathological conditions and behavioral observations.

ANGPTL4

The invention results from the desire to further elucidate the biological function of ANGPTL4 and its role in disease states. ANGPTL4 expression is found primarily in the placenta, adipose, liver and kidney tissues. This invention provides additional uses of ANGPTL4 and modulators of ANGPTL4 in the areas of hepatocytes, adipocytes and lipid homeostasis. The invention also describes transgenic or knockout mice containing a disruption in the ANGPTL4 gene, and uses thereof.

Angiopoietin-like 4 protein (ANGPTL4) is a secreted protein and is a member of the angiopoietin family. It is also known as hepatic fibrinogen/angiopoietin-related protein (HFARP) (Kim et al., *Biochem. J.* 346:603-610 (2000)), PGAR (PPARγ angiopoietin related protein) (Yoon, et al., *Mol. Cell Biol.*, 20:5343-5349 (2000)), fasting induced adipose factor (FIAF) (Kerten et al., *J. Biol. Chem.*, 275:28488-28493 (2000)); angiopoietin-related protein (ARP-4); NL2 (see U.S. Pat. Nos. 6,348,350; 6,372,491; and 6,455,496); and Ang6.

The ANGPTL4 protein from human is a 406 amino acid protein (e.g., U.S. Pat. Nos. 6,348,350, 6,372,491 & 6,455, 496), while the mouse ANGPTL4 is a 410 amino acid protein (Kim et al., *Biochem. J.* 346:603-610 (2000)). The mouse and human share about 75% identity at the amino acid level. Kim et al., *Biochem. J.* 346:603-610 (2000). ANGPTL4 has a signal peptide, three potential N-glycosylation sites, and four cysteines that can be involved in intramolecular disulfide bonding. ANGPTL4 forms higher molecular structures, e.g., as indicated in FIG. 3, Panel A. See also, e.g., Ge et al., *J. Biol. Chem.*, 279(3):2038-2045 (2004); Ge et al., *J. Lipid Res.* 45:2071-2079 (2004); and, Mandard et al., *J. of Biol. Chem.*, 279(33):34411-34420 (2004). ANGPTL4 can also be proteolytically processed, e.g., the substitution of R162G and R164E of ANGPTL4 (SEQ ID NO: 28) results in the variant ANGPTL4 running at a higher molecular weight on an SDS-Gel than the wild type protein (see FIG. 3, Panel B). See also, e.g., Ge et al., *J. Biol. Chem.*, 279(3):2038-2045 (2004); and, Mandard et al., *J. of Biol. Chem.*, 279(33):34411-34420 (2004).

Conserved regions of the angiopoietin family include a coiled-coil domain and a C-terminal fibrinogen (FBN)-like domain. See, e.g., Kim et al., *Biochem. J.* 346:603-610 (2000). It is suggested that ANGPTL4 is proteolytically processed in a regulated way to release the C-terminal fibrinogen-like domain. See, e.g., Ge et al., *J. Biol. Chem.*, 279(3): 2038-2045 (2004).

ANGPTL4 binds to integrin $\alpha_v\beta_5$. See, e.g., FIG. 9, Panels A-E. Another member of the family, angiopoietin-like 3 protein (ANGPTL3) is an angiogenic factor that binds to integrin $\alpha_v\beta_3$. See, e.g., US patent application 20030215451, published on Nov. 20, 2003, and Camenisch et al., *J. Biol. Chem.*, 277(19):17281-17290 (2002). ANGPTL3 does not appear to bind to receptor Tie2. Camenish et al., *Journal of Biol. Chem.*

277(19):17281-17290 (2002). ANGPTL3 is also a regulator of plasma lipid levels. See, e.g., Koishi et al., *Nat. Genetics* 30:151-157 (2002).

Integrin $\alpha_v\beta 5$ is a receptor for extracellular matrix proteins including vitronectin, and Del-1 (see, e.g., Stupack and Cheresh, *Journal of Cell Science* 115:3729-3738 (2002)). Alpha v-integrins have been implicated in tumour progression and metastasis. See, e.g., Marshall, J F and Hart, I R *Semin. Cancer Biol.* 7(3): 129-38 (1996). In addition, a role of alpha v-integrins during angiogenesis has also been shown. See, e.g., Eliceiri, B P and Cheresh, D A *Molecular Medicine* 4: 741-750 (1998). For example, a monoclonal antibody for $\alpha_v\beta_5$ was shown to inhibit VEGF-induced angiogenesis in rabbit cornea and the chick chorioallantoic membrane model. See, e.g., M. C. Friedlander, et al., *Science* 270:1500-1502 (1995). Antagonists of $\alpha_v\beta 3$ and $\alpha_v\beta 5$ were also shown to inhibit growth-factor and tumor-induced angiogenesis. See, e.g., Eliceiri and Cheresh, *Current Opinion in Cell Biology*, 13:563-568 (2001).

Use of ANGPTL4 and Modulators of ANGPTL4

The invention provides uses of ANGPTL4 or, an agonist or antagonist thereof, to modulate a variety of cell activities and processes, e.g., hepatocyte proliferation and/or cell adhesion, and pre-adipocyte proliferation and/or pre-adipocyte cell migration. ANGPTL4 is involved in modulating serum levels of triglyceride and cholesterol. In addition, ANGPTL4 can also be a negative regulator of inflammatory responses. Modulators of ANGPTL4 can be used to treat disorders and diseases related to these activities.

Liver

ANGPTL4 stimulates the proliferation of hepatocytes and the adhesion of hepatocytes. The liver is the major organ for cholesterol homeostasis. See also the section "Lipid Homeostasis" herein. Liver is responsible for cholesterol biosynthesis and catabolism of cholesterol. The liver synthesis and secretes very low density lipoproteins (VLDL). In the circulation, VLDL is metabolized to become low density lipoproteins (LDL), which are the major cholesterol carrying lipoproteins in the plasma.

The liver acts as a guardian interposed between the digestive tract and the rest of the body. A major hepatic function involves effective uptake, storage, metabolism and distribution to blood and bile large amounts of substances such as carbohydrates, lipids, amino acids, vitamins and trace elements. Another function of the liver is the detoxification of xenobiotic pollutants, drugs and endogenous metabolites, through both phase I (oxidation/reduction) and phase II (conjugation) mechanisms.

The liver is the major metabolic control organ of the human body that comprises thousands of minute lobules (lobuli hepatis), the functional units of the organ. Liver tissue contains two major differentiated cell types: parenchymal cells (i.e., hepatocytes) and non-parenchymal cells. The complex functions of liver are exerted to a large extent by hepatocytes, whereas non-parenchymal cells such as Kupffer cells, Ito cells and liver sinusoidal endothelial cells (LSEC) play important roles in supporting and providing supplies to hepatocytes. Mochida et al. *Biochem. Biophy. Res. Comm.* 226: 176-179 (1996).

In addition to normal growth during early development, liver tissue has a unique ability to regenerate at adult stage. Liver regeneration after the loss of hepatic tissue is a fundamental component of the recovery process in response to various forms of liver injury such as hepatotoxicity, viral infection, vascular injury and partial hepatectomy. Following partial hepatectomy, for example, the liver size is usually restored to its original mass within about six days. Liver growth and regeneration involves proliferation of both hepatocytes and non-parenchymal cells such as sinusoidal endothelial cells. Typically, hepatocytes are the first to proliferate, and other cells of the liver enter into DNA synthesis about 24 hours after the hepatocytes. Michalopoulos and DeFrances *Science* 276:60-66 (1997).

The invention provides methods for promoting liver growth and/or hepatocyte cell proliferation by administering an effective amount of ANGPTL4 or agonist thereof. The promoting effects of the invention can be assessed either in vitro or in vivo, using methods known in the art. See, e.g., Drakes et al. *J. Immunol.* 159:4268-4278 (1997); Omori et al. *Hepatology* 26:720-727 (1997); and, U.S. Pat. No. 5,227,158. For example, cell proliferation is assessed during culture using methods known in the art, including but not limited to, measuring the rate of DNA synthesis (see, e.g., Nakamura et al. *Biochem. Biophy. Res. Comm.* 122:1450 (1984), trypan blue dye exclusion/hemacytometer counting (see, e.g., Omiri et al. (1997) supra), or flow cytometry (see, e.g., Drakes (1997) supra).

In certain embodiments of the invention, ANGPTL4 or an agonist thereof is administered to induce cell adhesion of hepatocytes. Adhesion of hepatocytes can be assayed by methods known in the art, including, e.g., crystal violet assay. See also, Landegren, U. *J. Immunological Methods,* 67:379-388 (1984). In one embodiment of the invention, hepatocytes and other nonparenchymal liver cells are isolated from the target livers and resuspended in appropriate tissue culture medium with ANGPTL4 or an agonist thereof to induce cell adherence. If necessary, different cell fractions can be further separated (e.g., parenchymal cells from nonparenchymal cells) by centrifugation at different speeds for different length of time.

In another embodiment, the proliferative effect of an ANGPTL4 or ANGPTL4 agonist on hepatic cells and liver organ as a whole is measured in vivo using, for example, histochemistry assays of the liver tissue samples. In one aspect, in vivo proliferation of hepatic cells is assessed by reactivity to an antibody directed against a protein known to be present in higher concentrations in proliferating cells than in non-proliferating cells, such as proliferating cell nuclear antigen (PCNA or cyclin). Rodgers et al. *J. Burn Care Rehabil.* 18:381-388 (1997). In another aspect, a BrdU immunohistochemistry assay can be used as described by Gerber et al. *Development* 126:1149-1159 (1999).

Because of its essential role to life, liver dysfunction and diseases are often debilitating and life threatening. A number of acute or chronic pathological conditions are associated with structural and/or functional abnormalities of the liver. These include, but are not limited to, liver failure, hepatitis (acute, chronic or alcohol), liver cirrhosis, toxic liver damage, medicamentary liver damage, hepatic encephalopathy, hepatic coma or hepatic necrosis. Cellular growth enhancement of hepatocytes can be useful in treating liver disease. The compounds and methods of the invention can provide for the repair of liver damage. Not to be bound by theory, it is believed that this can be accomplished, either directly or indirectly, by stimulating liver cells to grow and divide. According to one embodiment, the invention provides methods for treating a pathological liver condition in a subject by administering an effective amount of an ANGPTL4 or ANGPTL4 agonist of the invention.

The phrase "pathological liver condition" is used interchangeably with "liver disorder" or "liver disease" to indicate any structural and/or functional liver abnormalities. Non-limiting examples of pathological liver condition include those conditions associated with liver failure, hepatitis (acute, chronic or alcohol), liver cirrhosis, toxic liver damage, medicamentary liver damage, hepatic encephalopathy, hepatic coma or hepatic necrosis.

In one aspect, the invention provides methods for protecting liver from damage in a subject susceptible to conditions or factors causative of liver damage. The phrase "liver damage" is used herein in the broadest sense, and indicates any structural or functional liver injury resulting, directly or indirectly, from internal or external factors or their combinations. Liver damage can be induced by a number of factors including, but not limited to, exposure to hepatotoxic compounds, radiation exposure, mechanical liver injuries, genetic predisposition, viral infections, autoimmune disease, such as, autoimmune chronic hepatitis and as a result of elevated in vivo levels of proteins, such as activin and TGF-β. Liver damage induced by hepatotoxic compounds includes direct cytotoxicity including drug hypersensitivity reactions, cholestasis, and injury to the vascular endothelium.

Many chemical and biological agents, either therapeutic or purely harmful, can induce liver damages and thus are hepatotoxic. Hepatotoxic compounds are also an important cause of chronic liver disease including fatty liver, hepatitis, cirrhosis and vascular and neoplastic lesions of the liver. (Sinclair et al., *Textbook of Internal Medicine,* 569-575 (1992) (editor, Kelley; Publisher, J. B. Lippincott Co.). Provided in the invention are methods for protecting liver in a subject from damage due to exposure to a hepatotoxic agent, comprising administering to the subject an ANGPTL4 or agonist, where said ANGPTL4 or ANGPTL4 agonist effectively protects liver from damage. In one aspect, the ANGPTL4 or ANGPTL4 agonist is administered prior to or concurrent with the exposure of said subject to the hepatotoxic agent, said hepatotoxic agent being a therapeutic agent such as a chemotherapeutic or radiation agent for treating cancers. As such, the methods serve to enhance the efficacy of the treatment by permitting the subject tolerance to high doses of the therapeutic agents. In another aspect, the ANGPTL4 or ANGPTL4 agonist is administered after the exposure of the subject to a hepatotoxic agent but prior to any detectable liver damage in the subject. Such methods can be useful for treating liver damages due to accidental exposure of the subject to a hepatotoxic agent.

Hepatotoxic agents may induce liver damage by cytotoxicity to the liver directly or through the production of toxic metabolites (this category includes the hypersensitivity reaction which mimics a drug allergy); cholestasis, an arrest in the flow of bile due to obstruction of the bile ducts; and vascular lesions, such as in veno occlusive disease (VOD), where injury to the vascular endothelium results in hepatic vein thrombosis. Individual susceptibility to liver damage induced by hepatotoxic agents is influenced by genetic factors, age, sex, nutritional status, exposure to other drugs, and systemic diseases (Sinclair et al., *Textbook of Internal Medicine,* supra).

Many hepatotoxic compounds unpredictably produce liver damage in a small proportion of recipients. In some patients, the liver damage is referred to as a hypersensitivity reaction and is like that of a drug reaction, where the patient presents with fever, rash and eosinophilia and has a recurrence of symptoms upon rechallenge of the drug. In other situations, the mechanism for injury is unknown and may represent aberrant metabolism in susceptible patients that permits the production or accumulation of hepatotoxic metabolites.

Those drugs inducing cytotoxicity by direct chemical attack include the following: Anesthetics, such as Enflurane, Fluoroxene, Halothane, and Methoxyflurane; Neuropsychotropics, such as, Cocaine, Hydrazides, Methylphenidate, and Tricyclics; Anticonvulsants, such as, Phenyloin and Valproic acid; Analgesics, such as, Acetaminophen, Chlorzoxazone, Dantrolene, Diclofenac, Ibuprofen, Indomethacin, Salicylates, Tolmetin, and Zoxazolamine; Hormones, such as, Acetohexamide, Carbutamide, Glipizide, Metahexamide, Propylthiouracil, Tamoxifen, Diethylstilbestrol; Antimicrobials, such as, Amphotericin B, Clindamycin, Ketoconazole, Mebendazole, Metronidazole, Oxacillin, Paraminosalicylic acid, Penicillin, Rifampicin, Sulfonamides, Tetracycline, and Zidovudine; Cardiovascular drugs, such as, Amiodarone, Dilitiazem, a-Methyldopa, Mexiletine, Hydrazaline, Nicotinic acid, Papaverine, Perhexyline, Procainamide, Quinidine, and Tocainamide; and Immunosuppressives and Antineoplastics, such as, Asparaginase, Cisplatin, Cyclophosphamide, Dacarbazine, Doxorubicin, Fluorouracil, Methotrexate, Mithramycin, 6-MP, Nitrosoureas, Tamoxifen, Thioguanine, and Vincristine; and Miscellaneous drugs, such as, Disulfuram, Iodide ion, Oxyphenisatin, Vitamin A and Paraminobenzoic acid.

Those hepatotoxic compounds producing hypersensitivity reaction in the liver include the following: Phenyloin, Paramino salicylic acid, Chlorpromazine, Sulfonamides, Erythromycin estolate, Isoniazid, Halothane, Methyldopa, and Valproic acid.

Hepatotoxic compounds including cholestasis, an arrest in the flow of bile, may take several forms. Centribular cholestasis is accompanied by portal inflammatory changes. Bile duct changes have been reported with some drugs such as erythromycin, while pure canalicular cholestasis is characteristic of other drugs such as the anabolic steroids. Chronic cholestasis has been linked to such drugs as methyltestosterone and estradiol.

Those hepatotoxic compounds inducing cholestatic disease include the following: Contraceptive steroids, androgenic steroids, anabolic steroids, Acetylsalicylic acid, Azathioprine, Benzodiazepine, Chenodeoxycholic acid, Chlordiazepoxide, Erythromycin estolate, Fluphenazine, Furosemide, Griseofulvin, Haloperidol, Imipramine, 6-Mercaptopurine, Methimazole, Methotrexate, Methyldopa, Methylenediamine, Methyltestosterone, Naproxen, Nitrofurantoin, Penicillamine, Perphenazine, Prochlorperazine, Promazine, Thiobendazole, Thioridazine, Tolbutamide, Trimethoprimsulfamethoxazole, Arsenic, Copper, and Paraquat.

Some drugs, although primarily cholestatic, can also produce hepatoxicity, and therefore the liver injury they cause is mixed. The drugs causing mixed liver injury include, for example, the following: Chlorpromazine, Phenylbutazone, Halothane, Chlordiazepoxide, Diazepam, Allopurinol, Phenobarbital, Naproxen, Propylthiouracil, Chloramphenicol, Trimethoprimsulfamethoxazxole, Amrinone, Disopyramide, Azathioprine, Cimetidine, and Ranitidine.

Vascular lesions of the liver, including thrombosis of the hepatic veins, occlusion of the hepatic venules or veno occlusive disease (VOD), and peliosis hepatitis, can be produced by drugs. In addition, lesions including sinusoidal dilation, perisinusoidal fibrosis, and hepatoportal sclerosis can occur. Midzonal and pericentral sinusoidal dilatation was first reported as a complication of oral contraceptive therapy. Peliosis hepatitis is a condition consisting of large blood-filled cavities that results from leakage of red blood cells through the endothelial barrier, followed by perisinusoidal fibrosis. It has been described in patients taking oral contraceptives, anabolic steroids, azathioprine and danazol. Injury and occlusion of the central hepatic venules is also known to be related to the ingestion of pyrrolizidine alkaloids, such as bush teas. The initial lesion is central necrosis accompanied by a progressive decrease in venule caliber. All of these lesions may be only partially reversible when the drug is stopped and cirrhosis can develop.

Several types of benign and malignant hepatic neoplasm can result from the administration of hepatotoxic compounds. Adenomas, a lesion restricted to women in the childbearing years, is related to the use of contraceptive steroids and the risk increases with duration of use. Hepatocellular carcinoma may also be seen in patients taking androgenic hormones for aplastic anemia or hypopituitarism.

Hepatotoxic compounds known to cause hepatic lesions include the following: Contraceptive steroids, Pyrriolizidine alkaloids, Urethane, Azathioprine, 6-Mercaptopurine, 6-Thioguanine, Mitomycin, BCNU, Vincristine, Adriamycin, Intravenous Vitamin E, Anabolic-androgenic steroids, Azathioprine, Medroxyprogesterone acetate, Estrone sulfate, Tamoxifen, inorganic arsenicals, Thorium dioxide, Vitamin A, methotrexate, Methylamphetamine hydrochloride, Vitamin A, Corticosteroids, Thorium dioxide, and Radium therapy.

Liver damage caused by other factors usually takes similar forms. Liver damage, whether caused by the hepatotoxicity of a compound, radiation therapy, genetic predisposition, mechanical injury or any combination of such and other factors, can be detected by several means. Biochemical tests have been used clinically for many years as the standard measure of hepatotoxicity. Most biochemical tests generally fall into two categories: tests which measure specific liver markers, for example, prothrombin clotting time, and/or hepatic blood flow, or tests which analyze serum markers, for detection of necrosis, cholestasis, progressive fibrogenesis, or hepatoma (Cornelius, C. in *Hepatotoxicology*, Meeks et al. eds., pgs. 181-185 (1991)). The importance of such tests lies in their simplicity and the fact that they are non-invasive. The rationale for the use of serum enzymes in assessing liver damage is that these enzymes, normally contained in the liver cells, gain entry into the general circulation when liver cells are injured.

Elevated serum enzyme activity suggests necrosis and/or cholestasis. Elevated levels of serum bilirubin conjugates suggest intra or extra hepatic cholestasis. However, there are certain limitations for the use of serum enzyme levels as single means of diagnosing liver injury. Serum enzyme levels may increase as a result of leakage from cells with altered permeability due to systemic effects of an agent rather than specific liver injury caused by a chemical. Histopathological examination of the liver is the next logical step in identifying and quantifying the nature and extent of liver injury.

The serum enzymes as markers of liver injury can be divided into four groups based on specificity and sensitivity to liver damage (Kodavanti et al., *Toxicologic Pathology* 20(4): 556-69 (1992); Kodavanti et al., *Archives of Toxicology* 63(5): 367-75 (1989).

Group I: these enzymes indicate more selectively hepatic cholestasis when elevated, e.g. alkaline phosphatase (AP), 5'-nucleotidase (5'-ND), and a-glutamyl transpeptidase (G-GT) and leucine aminopeptidase (LAP). Group II: These enzymes indicate parenchymal injury when elevated, e.g., aspartate transaminase (AST), alanine transaminase (ALT), fructose-1,6-diphosphate aldolase (ALD), lactate dehydrogenase (LDH), isocitrate dehydrogenase (ICDH), ornithine-carbamoyl-transferase (OCT), and sorbitol dehydrogenase (SDH) arginase and guanase. Group III: These enzymes represent injury of other tissue when elevated e.g., creatine phosphokinase (CPK). Group IV: These enzymes are depressed in hepatic injury, e.g., cholinesterase (ChE).

Other serum markers include, procollagen type III peptide levels (PIIIP) to assess if hepatic fibrogenesis is active; ammonia blood levels in hepatoencephalopathies; ligand in levels in necrosis and hepatoma; hyaluronate levels due to hepatic endothelial cell damage; a-1-fetoprotein (AFP) levels to detect hepatoma; carcinoembryonic antigen (CEA) levels to detect cancer metastasis to the liver; elevations of antibodies against a variety of cellular components, such as, mitochondrial, and nuclear and specific liver membrane protein; and detection of proteins, such as, albumin, globin, amino acids, cholesterol, and other lipids. Also, biochemical analysis of a variety of minerals, metabolites, and enzymes obtained from liver biopsies can be useful in studying specific biochemical defects in inherited, acquired, and experimentally induced liver disorders.

Liver function tests can be performed to assess liver injury. Liver function tests include the following: Group I assessment of hepatic clearance of organic anions, such as, bilirubin, indocyanine green (ICG), sulfobromophthalein (BSP) and bile acids; Group II assessment of hepatic blood flow by measurements of galactose and ICG clearance; and, Group III assessment of hepatic microsomal function, through the use of the aminopyrine breath test and caffeine clearance test. For example, serum bilirubin can be measured to confirm the presence and severity of jaundice and to determine the extent of hyperbilirubinemia, as seen in parenchymal liver disease. Aminotransferase (transaminase) elevations reflect the severity of active hepatocellular damage, while alkaline phosphatase elevations are found with cholestasis and hepatic infiltrates (Isselbacher, K. and Podolsky, D. in *Harrisson's Principles of Internal Medicine,* 12*th edition*, Wilson et al. eds., 2:1301-1308 (1991)). Methods for performing serum enzyme analysis are known in the art and are, for example, described in Kodavanti et al. supra.

Because extensive liver injury may lead to decreased blood levels of albumin, prothrombin, fibrinogen, and other proteins synthesized exclusively by hepatocytes, these protein levels may be measured as indicators of liver injury. In contrast to measurements of serum enzymes, serum protein levels reflect liver synthetic function rather than just cell injury (Podolsky, D. Harrison's *Principles of Internal Medicine,* 12*th edition*, Wilson et al. eds., 2: 1308-1311 (1991)).

In many patients, computed tomography (CT), ultrasound, scintiscans, or liver biopsy may be needed to determine the nature of the liver disease (Isselbacher, K, and Friedman, L. and Needleman, L. in *Harrison's Principles of Internal Medicine,* 12*th edition*, Wilson et al. eds., 2: 1303-1307 (1991)).

The invention provides methods for enhancing the effect of therapy in a subject, said methods comprising administering to the subject an ANGPTL4 or ANGPTL4 agonist in a manner effective to protect the liver of the subject from damage caused by a hepatoxic compound prior to, or simultaneous with, the therapy, thereby increasing the subject's tolerance to the therapy. For example, the chemotherapeutic agents used during the course of chemotherapy can have cytotoxic effects upon hepatic cells, therefore limiting the dosage and/or duration of the chemotherapeutic agent being administered to the patient. By exposing the liver to a composition comprising an ANGPTL4 or ANGPTL4 agonist, such toxic effects can be prevented or reduced. As such, the dosage of the chemotherapeutic agents can be increased, thereby enhancing the efficacy of the cancer therapy.

An ANGPTL4 or ANGPTL4 agonist can be combined with other agents in the methods described herein. For example, several growth factors and cytokines have been implicated as being able to induce liver regeneration, most notably hepatocyte growth factor (HGF), epidermal growth factor (EGF), transforming growth factor-(TGF-), interleukin-6 (IL-6), tumor necrosis factor-(TNF-α), basic and acidic fibroblast growth factors, CTGF, HB-EGF, and norepinephrine. Fujiwara et al. *Hepatol.* 18:1443-9 (1993); Baruch et al. *J. Hepatol.* 23:328-32 (1995); Ito et al. *Biochem. Biophys. Res. Commun.* 198:25-31 (1994); Suzuma et al. *J. Biol. Chem.* 275: 40725-31 (2000); and, Michalopoulos and DeFrances (1997) supra. These can be combined with ANGPTL4 or ANGPTL4 agonist.

Around HGF, one of the most potent liver mitogens, was first identified as a factor capable of stimulating DNA synthesis in cultured hepatocytes but is now known to have multiple distinct functions on a variety of epithelial cells. Nakamura et al. *Biochem. Biophys. Res. Comm.* 122:1450 (1984); and, Russell et al. *J. Cell. Physiol.* 119:183-192 (1984). HGF is also known as Scatter factor (SF), leading to the designation HGF/SF. Stoker and Perryman *J. Cell Sci.* 77:209-223 (1985); and, Gherardi and Stoker *Nature* 346:228 (1990). The biological effects of HGF are transduced via a single tyrosine kinase receptor, Met, the product of the Met protooncogene. In the liver, HGF is expressed in non-hepatocyte cells such as Ito cells and LSECs, whereas met transcripts are strongly expressed in hepatocytes. Hu et al. *Am. J. Pathol.* 142:1823-1830 (1993). After chemical or mechanical liver injury, HGF levels sharply increase, leading to a strong hepatocyte proliferation. Horimoto et al. *J. Hepatol.* 23:174-183 (1995). Livers from transgenic mice with liver-specific overexpression of HGF are twice the size of livers of control animals and they regenerate much faster after partial hepatectomy. Sakata et al. (1996) *Cell Growth Differ.* 7:1513-1523; Shiota et al. (1994) *Hepatol.* 19:962-972.

Angiogenesis is an important cellular event in which vascular endothelial cells proliferate, prune and reorganize to form new vessels from preexisting vascular network. There are compelling evidences that the development of a vascular supply is essential for normal and pathological proliferative processes (Folkman and Klagsbrun (1987) *Science* 235:442-447). Regenerating liver, in analogy to rapidly growing tumors, must synthesize new stroma and blood vessels. See, e.g., WO03/103581; Yamane et al. *Oncogene* 9:2683-2690 (1994); Mochida et al. *Biochem. Biophy. Res. Comm.* 226: 176-179 (1996); Ajioka et al. *Hepatology* 29:396-402 (1999); and, Assy et al. *J. Hepatol.* 30:911-915 (1999). Michalopoulos and DeFrances (1997) supra; Mochida et al. (1996). In one embodiment of the invention, ANGPTL4 or ANGPTL4 agonist is administered in combination with an angiogenic agent, e.g., VEGF or activators of VEGFRs. An "angiogenic factor or agent" is a growth factor which stimulates the development of blood vessels, e.g., promotes angiogenesis, endothelial cell growth, stability of blood vessels, and/or vasculogenesis, etc. For example, angiogenic factors, include, but are not limited to, e.g., VEGF and members of the VEGF family (A, B, C, D, and E), PlGF, PDGF family, fibroblast growth factor family (FGFs), TIE ligands (Angiopoietins), ANGPTL3, ephrins, etc. It would also include factors that accelerate wound healing, such as growth hormone, insulin-like growth factor-I (IGF-I), VIGF, epidermal growth factor (EGF), CTGF and members of its family, and TGF-α and TGF-β. See, e.g., Klagsbrun and D'Amore, *Annu. Rev. Physiol.,* 53:217-39 (1991); Streit and Detmar, *Oncogene,* 22:3172-3179 (2003); Ferrara & Alitalo, *Nature Medicine* 5(12):1359-1364 (1999); Tonini et al., *Oncogene,* 22:6549-6556 (2003) (e.g., Table 1 listing known angiogenic factors); and, Sato *Int. J. Clin. Oncol.,* 8:200-206 (2003).

Lipid Homeostasis

ANGPTL4 is implicated in modulating other aspects of energy homeostasis, besides the liver. ANGPTL4 is associated with adipose differentiation, systemic lipid metabolism, and angiogenesis. See, e.g., Yoon et al., *Molecular and Cellular Biology,* 20(14):5343-5349 (2000); Le Jan et al., *American Journal of Pathology,* 162(5):1521-1528 (2003); and, EP 1403367. ANGPTL4 expression is also induced by PPAR gamma and alpha in adipose tissue, and is induced by starvation. See, e.g., Yoon et al., *Mol. Cell. Biol.,* 20:5343-5349 (2000); and, Kersten et al., *J. Biol. Chem.,* 275: 28488-28493 (20000). Expression of ANGPTL4 is upregulated during fasting, and abundance of the protein in plasma decreases with high fat feeding.

In addition, ANGPTL4 inhibits lipoprotein lipase (LPL) activity. See, e.g., EP1403367. Lipoprotein lipase (LPL) is a secreted glycoprotein that mediates lipoprotein metabolism by hydrolyzing triglycerides present in chylomicrons and very low density lipoproteins (VLDLs), to produce free fatty acids and phospholipids.

As provided herein, ANGPTL4 knockout mice have decreased levels of cholesterol and serum triglycerides compared to their gender-matched wild-type littermates. See sections entitled Transgenic Knockout Animals and Example 4, herein. In addition, intravenous injection of ANGPTL4 increases circulating plasma lipid levels in mice and increases levels of very low-density lipoprotein. See, e.g., Yoshida et al., *Journal of Lipid Research,* 43: 1770-1772 (2002), and see FIG. 10.

Methods of modulating serum levels of triglycerides or cholesterol in a subject are provided in the invention. For example, methods include administering an effective amount of a composition comprising an ANGPTL4 or ANGPTL4 agonist or an ANGPTL4 antagonist to a subject, thereby modulation the serum levels of triglycerides or cholesterol in a subject. In one embodiment, an ANGPTL4 or ANGPTL4 agonist is administered, which results in an accumulation of triglycerides or cholesterol in the serum. In another embodiment, an effective amount of an ANGPTL4 antagonist is administered to a subject, thereby reducing the level of at least one triglyceride, free fatty acids and/or cholesterol in the serum of the subject compared to the subject before treatment, or a subject with no treatment or reduced treatment. Mean serum cholesterol and triglyceride levels can be assayed as known in the art.

ANGPTL4 can also modulate adipocytes. For example, ANGPTL4 can stimulate pre-adipocyte proliferation or induce cell migration of pre-adipocytes. Adipose tissue consists primarily of adipocytes, which also play a critical role in energy homeostasis. Adipocytes synthesize and store lipids when nutrients are plentiful, and release fatty acids into the circulation when nutrients are required. White adipose tissue (WAT) and brown adipose tissue (BAT) are found in vertebrates. WAT stores and releases fat dependent on nutritional needs of the animal. WAT stored fat is used for (1) heat insulation (e.g., subcutaneous fat), (2) mechanical cushion (e.g., surrounding internal organs), and (3) as a source of energy. BAT burns fat, releasing the energy as heat through thermogenesis for maintaining homeothermy by increasing thermogenesis in response to lower temperatures and for maintaining energy balance by increasing energy expenditure in response to increases in caloric intake. See, e.g., Sears, I. B. et al. (1996) *Mol. Cell. Biol.* 16(7):3410-3419 (1996). Generally, BAT diminishes with age, but can be re-activated under certain conditions, e.g., prolonged exposure to cold, maintenance on a high fat diet and in the presence of noradrenaline producing tumors.

Adipogenesis involves morphological changes, growth arrest, expression of lipogenic enzymes, lipid accumulation and acquire sensitivity to various hormones, e.g., insulin. Methods are provided that include stimulating adipocyte proliferation by administering an effective amount of ANGPTL4 or an ANGPTL4 agonist. Cell proliferation can be assessed during culture using methods known in the art, including but not limited to, measuring the rate of DNA synthesis (see, e.g., Nakamura et al. *Biochem. Biophy. Res. Comm.* 122:1450 (1984), trypan blue dye exclusion/hemacytometer counting (see, e.g., Omiri et al. (1997) supra), or flow cytometry (see, e.g., Drakes (1997) supra). ANGPTL4 or ANGPTL4 agonists can be useful in inducing the proliferation of adipocytes in disorders where additional adipocytes would be beneficial, e.g., including, but not limited to, e.g., wasting diseases (e.g., such as in types of cancer, immunocompromised patients (e.g., AIDS sufferers, etc.), aging individual), etc. Methods are also provided that include inducing preadipocyte cell migration by administering an effective amount of ANGPTL4 or an ANGPTL4 agonist.

ANGPTL4 or ANGPTL4 agonists can also be combined with other factors that promote differentiation of adipocytes. These factors include, but are not limited to, e.g., IGF-1, insulin, glucocorticoids, 3,3',5-Triiodothyronine, retinoic acid, $PGF_{2\alpha}$, $PGI_2$, etc. Additional factors can also be combined with ANGPTL4 or ANGPTL4 agonist. For example, adipogenesis is subject to hormonal and transcriptional control. For example, adipogenesis can be mediated by a cascade of transcription factors including, e.g., members of the peroxisome proliferators-activated receptor (PPAR), e.g., (PPARα, γ) family, CCAAT/enhancer binding protein (C/EBP) family, and basic helix-loop-helix leucine zipper (bHLH) family, e.g., ADD1/SREBP1. See, e.g., Wu et al. *Current Opin. Cell Biol* 11:689-694 (1999); Rosen and Spiegelman *Annu Rev Cell Dev Biol* 16:145-171 (2000); Gregoire et al., *Physiological Reviews* 78(3) (1998); and, Kim and Spiegelman *Genes Devel* 10:1096-1107 (1996)). PPARγ acts in adipose tissue and promotes adipogenesis and lipid storage. See, e.g., Rosen et al., *Annu. Rev. Cell Dev. Biol.*, 16:145-171 (2000); Rosen et al., *Mol. Cell.* 4:611-617 (1999); Ren et al., *Genes Dev.* 16:27-32 (2002); Rosen et al., *Genes Dev.*, 16:22-26 (2002); and, Fukumura et al., *Circ. Res.* 93:e88-e97 (2003). PPAR also mediates lipoprotein lipase mRNA and protein levels in adipocytes and other cells (see, e.g., Gbaguidi et al., *FEBS Letters* 512:85-90 (2002)), and PPARs have also been implicated in cancer (see, e.g., Yoshimura et al., *Int. J. Cancer* 104:597-602 (2003); and, Kubota et al *Cancer Research* 58:3344-52 (1998)).

However, growth and/or formation of adipose tissue are often not desired. For example, obesity typically results when energy intake exceeds energy expenditure, resulting in the growth and/or formation of adipose tissue via hypertrophic and hyperplastic growth. Hypertrophic growth is an increase in size of adipocytes stimulated by lipid accumulation. Hyperplastic growth is defined as an increase in the number of adipocytes in adipose tissue.

Obesity is a chronic disease that is highly prevalent in modern society and is associated not only with a social stigma, but also with decreased life span and numerous medical problems, including adverse psychological development, reproductive disorders such as polycystic ovarian disease, dermatological disorders such as infections, varicose veins, *Acanthosis nigricans*, and eczema, exercise intolerance, insulin resistance, hypertension, hypercholesterolemia, cholelithiasis, osteoarthritis, orthopedic injury, thromboembolic disease, cancer, and coronary heart disease. Rissanen et al., *British Medical Journal,* 301: 835-837 (1990). Treatment of obesity involves using appetite suppressors and other weight-loss inducers, dietary modifications, and the like, but, similar to the patients with insulin resistance, the majority of obese patients undergo primary dietary failure over time, thereby failing to achieve ideal body weight. ANGPTL4 antagonists can be used to treat obesity and/or reducing total body mass in a subject, using an effective amount of an ANGPTL4 antagonist. Obesity can be determined by BMI and/or an obesity-determining property, which are known in the art and described herein. For example, treatment of obesity generally refers to reducing the BMI of the mammal to less than about 25.9, and maintaining that weight for at least 6 months. The treatment suitably results in a reduction in food or caloric intake by the mammal. In addition, treatment in this context refers to preventing obesity from occurring if the treatment is administered prior to the onset of the obese condition. Treatment includes the inhibition and/or complete suppression of lipogenesis in obese mammals, i.e., the excessive accumulation of lipids in fat cells or accumulation of fat cells, which is one of the major features of human and animal obesity, as well as loss of total body weight. A reduction in total body mass can be measured using standard techniques (e.g., scales). In one embodiment, adiposity (fat) of a subject is reduced. In this manner, conditions related to obesity can also be treated, e.g., cardiovascular disease, diabetes, etc.

ANGPTL4 is also implicated in the modulation of leptin, which is an adipocyte-derived hormone. Leptin, which is structurally related to cytokines, acts on receptors that belong to the cytokine-receptor superfamily. See, e.g., Zhang F, et al., *Nature* 387:206-209 (1997); Tartaglia L A, et al., *Cell* 83:1263-1271 (1995); and, Lee G-H, et al., *Nature* 379:632-635 (1996). Leptin is encoded by the gene affected in the obese (ob) mutation (Zhang F, et al., *Nature* 387:206-209 (1997)). The long form of the leptin receptor is encoded by the gene affected in the diabetic (db) mutation (Tartaglia L A, et al., *Cell* 83:1263-1271 (1995)). The leptin receptor, which there are several isoforms, is most closely related to the gp130 and LIFR signal transducing subunits that are activated by cytokines such as IL-6, LIF and CNTF and hormone receptors for growth hormone such as erythropoietin. See, e.g., Tartaglia L A, et al., supra. Lack of functional leptin or its receptor causes severe obesity. See, e.g., Zhang et al., supra; Lee et al., supra; and, Chen H et al, *Cell* 84:491-495 (1996). Leptin is known to act in certain regions of the brain (e.g., hypothalamus) to regulate food intake, energy expenditure and neuroendocrine function, e.g., it has been shown to be a key regulator of fat stores, where leptin levels increase with increasing fat stores. See, e.g., Zhang Y, et al., *Nature* 372:425-432 (1994); Halaas J L et al., *Science* 269:543-546 (1995); Campfield L A, et al., *Science* 269:546-549 (1995); and, Pellymounter M A, et al., *Science* 269:540-543 (1995).

Leptin was also found to be an angiogenic factor. See, e.g., Sierra-Honigmann et al., "Biological Action of Leptin as an Angiogenic Factor" *Science* 281:1683-1686 (1998); and, Bouloumie et al., *Circ. Res.* 83:1059-1066 (1998). Adipose tissue growth depends on neovascularization. See, e.g., Rupnick et al., *PNAS USA* 99(16):10730-10735 (2002). Leptin also plays a role in immunity. See, e.g., La Cava and Matarese, "The Weight of Leptin in Immunity" *Nature Reviews Immunology* 5:371-379 (2004). Other leptin activities include modulating reproduction, modulating hematopoiesis, modulating glucose metabolism, and modulating proinflammatory immune responses. See, e.g., Chelab et al., *Nature Genetics* 12:318-320 (1996); Stroebel et al., *Nature Genetics* 18:213-215 (1998); Clement et al., *Nature* 392:398-401 (1998); Cioffi et al., *Nature Medicine* 2: 585-589 (1996); Gainsford et al., *PNAS USA,* 93:14564-14568 (1996); Kamohara et al., *Nature* 389:374-377 (1997); Loffreda et al., *FASEB J.* 12:57-65 (1998); and, Lord et al., *Nature* 394:897-901 (1998).

ANGPTL4 is up regulated in ob/ob (leptin knockout) and db/db (leptin receptor knockout) mice. The invention provides methods for modulating leptin and/or leptin activities by administering an effective amount of an ANGPTL4, ANGPTL4 agonist or ANGPTL4 antagonist. Leptin levels can be assayed used standard techniques, e.g., SDS-PAGE, immunoblots, etc.

ANGPTL4, ANGPTL4 agonists and/or ANGPTL4 antagonists can be used in the treatment of diseases and disorders related to disruptions of lipid homeostasis and metabolism of fat which include, but are not limited to, e.g., metabolic diseases such as cardiac disorders, cardiovascular, endothelial or angiogenic disorders, dyslipidemia, hypertension, atherosclerosis, arteriosclerosis, coronary artery disease (CAD), coronary heart disease, hypercholesterolemia, heart failure, stroke, diabetes, pancreatic dysfunctions, osteoarthritis, gallstones, cancer, glaucoma, obesity, as well as related disorders such as adipositas, eating disorders, wasting syndromes (cachexia), sleep apnea, and others. For example, several human conditions are characterized by distinctive lipid compositions of tissues, cells, membranes, and extracellular regions or structures. For example, in atherosclerosis, cholesterol (unesterified, esterified, and oxidized forms) and other lipids accumulate in cells and in extracellular areas of the arterial wall and elsewhere. These lipids have potentially harmful biologic effects, for example, by changing cellular functions, including gene expression, and by narrowing the vessel lumen, obstructing the flow of blood. Regulation of lipid levels would provide numerous substantial benefits. The effects of administration of ANGPTL4, agonist or antagonist can be measured likewise by a variety of assays known in the art, including analysis of fat cells and tissue, such as fat pads, total body weight, triglyceride levels in muscle, liver, and fat, fasting and non-fasting levels of leptin, and the levels of free fatty acids and triglycerides in the blood. ANGPTL4 antagonist can also be use to inhibit migration of pre-adipocytes by administering an effective amount of an ANGPTL4 antagonist.

In certain aspects of the invention, it is desirable to combine the ANGPTL4, ANGPTL4 agonist or ANGPTL4 antagonist therapeutic agents with other therapeutic regimens. ANGPTL4 or ANGPTL4 agonists can be combined with the administrations of other factors, e.g., such as those described herein. As for antagonists, ANGPTL4 antagonists can be combined with the administration of, e.g., therapeutic agents to treat hyperlipidemia (and diseases associated with hyperlipidemia, e.g., obesity, hypercholesterolemia, atherosclerosis, cardiovascular disease, diabetes mellitus, hypothyroidism, Cushing's syndrome), e.g., including but not limited to, e.g., niacin, cholestyramine, colestipol, gemfibrozil, clofibrate, statins, fluvastatin (Lescol), pravastatin, simvastatin, rosuvastin calcium (ZD-4522), pitavastatin (NK104), premarin/pravachol (estrogen/pravastatin), ezetimbe/simvastatin, superstatin, Lipitor, CETi-1 vaccine, antibodies against CETP (cholesterol ester transfer protein), BMS-201038 (a microsomal triglyceride transport protein), FM-VP4 (cholesterol transport inhibitor), phyostanol, hypoglycemic agents, insulin, pramlintide, amylin, AC2993 synthetic exendin-4, Xenical (orlistat), ciliary neutrophic factor, Axokine, Metformin XT, Merformin, Glucovance (metformin/glyburide), dexlipotam (R+/−alpha-lipoic acid), PPAR agonists, beta-3-adrenergic receptor agonists, lipase inhibitors, ATL-962, leptin, anorectics or appetite suppressant, phentermine, Meridia (silbutramine), Wellbutrin (buproion), Procyglem (diazoxide), Tenuate (diethylpropion), Revia (naltrexon), Bontril (phendimetrazine), Zoloft (sertraline), ciliary neurotrophic factor (CNTF), Axokine, CB1-cannabinoid receptor antagonists, SR 141716, phytopharm, AOD9604, hGH 177-191, weight-loss agent, and derivatives thereof (e.g., salts, pegy-lated versions, etc.). See also, WO96/04260 (compounds for the treatment of Type II diabetes), WO94/01420, WO95/17394, WO97/36579, WO97/25042, WO99/08501, WO99/19313, and WO99/16758. Lifestyle changes can also be combined with the therapeutic agents of the invention. They include, but are not limited to, e.g., diet, exercise, limited cholesterol intake, smoking cessation, etc. See also, WO91/19702 (hypoglycemic and hypocholesterolemic agents). In certain aspects, ANGPTL4 antagonists can be combined with, e.g., cytokines and other proinflammatory molecules and several growth factors which inhibit adipogenesis. These include, but are not limited to, e.g., tumor necrosis factor (TNF)-α, IL-1, PDGF, FGF, EGF, transforming growth factor (TGF)-α, -β preadipocyte factor-1 (pref-1), etc. See, e.g., Gregoire et al., *Physiological Reviews* 78(3):783-809 (1998).

A "weight-loss agent" refers to a molecule useful in treatment or prevention of obesity. Such molecules include, e.g., hormones (catecholamines, glucagon, ACTH, and growth hormone combined with IGF-1; the Ob protein; clofibrate; halogenate; cinchocaine; chlorpromazine; appetite-suppressing drugs acting on noradrenergic neurotransmitters such as mazindol and derivatives of phenethylamine, e.g., phenylpropanolamine, diethylpropion, phentermine, phendimetrazine, benzphetamine, amphetamine, methamphetamine, and phenmetrazine; drugs acting on serotonin neurotransmitters such as fenfluramine, tryptophan, 5-hydroxytryptophan, fluoxetine, and sertraline; centrally active drugs such as naloxone, neuropeptide-Y, galanin, corticotropin-releasing hormone, and cholecystokinin; a cholinergic agonist such as pyridostigmine; a sphingolipid such as a lysosphingolipid or derivative thereof; thermogenic drugs such as thyroid hormone; ephedrine; beta-adrenergic agonists; drugs affecting the gastrointestinal tract such as enzyme inhibitors, e.g. tetrahydrolipostatin, indigestible food such as sucrose polyester, and inhibitors of gastric emptying such as threo-chlorocitric acid or its derivatives; β-adrenergic agonists such as isoproterenol and yohimbine; aminophylline to increase the .beta.-adrenergic-like effects of yohimbine, an $\alpha_2$-adrenergic blocking drug such as clonidine alone or in combination with a growth-hormone releasing peptide; drugs that interfere with intestinal absorption such as biguanides such as metformin and phenformin; bulk fillers such as methylcellulose; metabolic blocking drugs such as hydroxycitrate; progesterone; cholecystokinin agonists; small molecules that mimic ketoacids; agonists to corticotropin-releasing hormone; an ergot-related prolactin-inhibiting compound for reducing body fat stores (U.S. Pat. No. 4,783,469 issued Nov. 8, 1988); beta-3-agonists; bromocriptine; antagonists to opioid peptides; antagonists to neuropeptide Y; glucocorticoid receptor antagonists; growth hormone agonists; combinations thereof; etc.

Other Uses

ANGPTL4 also appears to be a negative regulator of inflammatory responses. In certain embodiments of the invention, ANGPTL4s or ANGPTL4 agonists can be used to inhibit the immune response, e.g., in the case of undesired or harmful immune response, e.g., in graft rejection or graft-versus-host diseases. ANGPTL4 antagonists can be useful in stimulating the immune system. For example, stimulating the immune system would be desired in leukemia, other types of cancer, immunocompromised patients (e.g., AIDS sufferers, etc.), etc.

ANGPTL4 is also implicated in cancer. ANGPTL4, when expressed in tumor cells, causes tumor cell proliferation, in vitro and in vivo (See, provisional application 60/589,782 filed concurrently with the present application, which is incorporated by reference for all purposes). When ANGPTL4 is expressed in tumors being treated with an anti-angiogenesis factor, e.g., anti-VEGF antibody, the tumor still maintains the ability to grow. It has also been shown to be upregulated in renal cancers. See, e.g., WO 02/07941; and, Le Jan et al., *American Journal of Pathology,* 162(5):1521-1528 (2003). In addition, ANGPTL4 is a proangiogenic factor (see, e.g., S. Le Jan et al., *Am. J. Pathol.,* 162(5):1521-1528 (2003)), which are targets for cancer therapy, and is an apoptosis survival factor for endothelial cells (see, e.g., Kim et al., *Biochem J.* 346:603-610 (2000). Like VEGF (Shweiki et al., *Proc. Natl. Acad. Sci, USA* 92:768-772 (1995), ANGPTL4 expression is increased in response to hypoxia. See, e.g., Le Jan et al., *American Journal of Pathology,* 162 (5):1521-1528 (2003). Researchers have reported connections between angiogenesis and adipogenesis or adipose tissue growth. See, e.g., Sierra-Honigmann et al., "Biological Action of Leptin as an Angiogenic Factor" *Science* 281:1683-1686 (1998); Rupnick et al., "Adipose tissue mass can be regulated through the vasculature" *Proc. Nat. Acad. Sci. USA,* 99(16):10730-10735 (2002); Kolonin et al., "Reversal of obesity by targeted ablation of adipose tissue" *Nature Medicine* Advance Online publication May 9, 2004: 1-8; and, Fukumura et al., "Paracrine Regulation of Angiogenesis and Adipocyte Differentiation During In Vivo Adipogenesis." *Circ. Res.* 93:e88-e97 (2003).

ANGPTL4 can also be used in diagnostic assays. Many different assays and assay formats can be used to detect the amount of ANGPTL4 in a sample relative to a control sample. These formats, in turn are useful in the diagnostic assays of the invention, which are used to detect the presence or onset of disorders described herein in a subject.

Any procedure known in the art for the measurement of soluble analytes can be used in the practice of the instant invention. Such procedures include but are not limited to competitive and non-competitive assay systems using techniques such as radioimmunoassay, enzyme immunoassays (EIA), e.g., ELISA, "sandwich" immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays. See, e.g., U.S. Pat. Nos. 4,845,026 and 5,006,459.

Transgenic Knockout Animals of ANGPTL4

Nucleic acids which encode ANGPTL4 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. The invention provides cDNA encoding an ANGPTL4 which can be used to clone genomic DNA encoding an ANGPTL4 in accordance with established techniques and the genomic sequences used to generate transgenic animals that contain cells which express DNA encoding ANGPTL4.

Any technique known in the art may be used to introduce a target gene transgene into animals to produce the founder lines of transgenic animals. Such techniques include, but are not limited to pronuclear microinjection (U.S. Pat. Nos. 4,873,191, 4,736,866 and 4,870,009); retrovirus mediated gene transfer into germ lines (Van der Putten, et al., *Proc. Natl. Acad. Sci., USA,* 82:6148-6152 (1985)); gene targeting in embryonic stem cells (Thompson, et al., *Cell,* 56:313-321 (1989)); nonspecific insertional inactivation using a gene trap vector (U.S. Pat. No. 6,436,707); electroporation of embryos (Lo, *Mol. Cell. Biol.,* 3:1803-1814 (1983)); and sperm-mediated gene transfer (Lavitrano, et al., *Cell,* 57:717-723 (1989)); etc.

Typically, particular cells would be targeted for ANGPTL4 transgene incorporation with tissue-specific enhancers. Transgenic animals that include a copy of a transgene encoding an ANGPTL4 introduced into the germ line of the animal at an embryonic stage can be used to examine the effect of increased expression of DNA encoding ANGPTL4 polypeptides. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of ANGPTL4 can be used to construct an ANGPTL4 "knock out" animal which has a defective or altered gene encoding an ANGPTL4 protein as a result of homologous recombination between the endogenous gene encoding ANGPTL4 and altered genomic DNA encoding ANGPTL4 introduced into an embryonic stem cell of the animal. In certain embodiments, the knock out animal is a mammal, e.g., a rodent such as a rat or mouse. For example, cDNA encoding an ANGPTL4 can be used to clone genomic DNA encoding an ANGPTL4 in accordance with established techniques. A portion of the genomic DNA encoding the ANGPTL4 can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, *Cell,* 51:503 (1987) for a description of homologous recombination vectors).

The vector is introduced into an embryonic stem cell line (e.g., by electroporation) and cells in which the introduced DNA has homologously recombined with the endogenous DNA are selected (see e.g., Li et al., *Cell,* 69:915 (1992)). The selected cells are then injected into a blastocyst of an animal (e.g., a mouse or rat) to form aggregation chimeras (see e.g., Bradley, in *Teratocarcinomas and Embryonic Stem Cells: A Practical Approach,* E. J. Robertson, ed. (IRL, Oxford, 1987), pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the gene encoding the ANGPTL4.

In addition, knockout mice can be highly informative in the discovery of gene function and pharmaceutical utility for a drug target, as well as in the determination of the potential on-target side effects associated with a given target. Gene function and physiology are so well conserved between mice and humans, since they are both mammals and contain similar numbers of genes, which are highly conserved between the species. It has recently been well documented, for example, that 98% of genes on mouse chromosome 16 have a human ortholog (Mural et al., *Science* 296:1661-71 (2002)).

Although gene targeting in embryonic stem (ES) cells has enabled the construction of mice with null mutations in many genes associated with human disease, not all genetic diseases are attributable to null mutations. One can design valuable mouse models of human diseases by establishing a method for gene replacement (knock-in) which will disrupt the mouse locus and introduce a human counterpart with mutation, Subsequently one can conduct in vivo drug studies targeting the human protein (Kitamoto et. Al., *Biochemical and Biophysical Res. Commun.*, 222:742-47 (1996)).

Uses of Transgenic Animals

In certain embodiments, the invention encompasses methods of screening compounds to identify those that mimic the ANGPTL4 (agonists) or prevent the effect of the ANGPTL4 (antagonists). Agonists that mimic an ANGPTL4 would be especially valuable therapeutically in the inducing activities of ANGPTL4, e.g., as described herein, and in those instances where a negative phenotype is observed based on findings with the non-human transgenic animal whose genome comprises a disruption of the gene which encodes for the ANGPTL4. Antagonists that prevent the effects of an ANGPTL4 would be especially valuable therapeutically in preventing ANGPTL4 activities, e.g., described herein, and in those instances where a positive phenotype is observed based upon observations with the non-human transgenic knockout animal. Screening assays for antagonist drug candidates are designed to identify compounds that bind or complex with the ANGPTL4 encoded by the genes identified herein, or otherwise interfere with the interaction of the encoded polypeptide with other cellular proteins, e.g., an ANGPTL4 receptor (e.g., $\alpha_v\beta_5$), lipolipase protein, etc.

For example, the effect of an antagonist to an ANGPTL4 can be assessed by administering an ANGPTL4 antagonist to a wild-type mouse in order to mimic a known knockout phenotype. Thus, one would initially knockout the ANGPTL4 gene of interest and observe the resultant phenotype as a consequence of knocking out or disrupting the ANGPTL4 gene. Subsequently, one could then assess the effectiveness of an antagonist to the ANGPTL4 by administering an antagonist to the ANGPTL4 to a wild-type mouse. An effective antagonist would be expected to mimic the phenotypic effect that was initially observed in the knockout animal.

Likewise, one could assess the effect of an agonist to an ANGPTL4, by administering an ANGPTL4 agonist to a non-human transgenic mouse in order to ameliorate a known negative knockout phenotype. Thus, one would initially knockout the ANGPTL4 gene of interest and observe the resultant phenotype as a consequence of knocking out or disrupting the ANGPTL4 gene. Subsequently, one could then assess the effectiveness of an agonist to the ANGPTL4 by administering an agonist to the ANGPTL4 to a non-human transgenic mouse. An effective agonist would be expected to ameliorate the negative phenotypic effect that was initially observed in the knockout animal.

In another assay for antagonists, mammalian cells or a membrane preparation expressing the receptor would be incubated with a labeled ANGPTL4 in the presence of the candidate compound. The ability of the compound to enhance or block this interaction could then be measured.

Antibodies

Antibodies of the invention include anti-ANGPTL4 antibodies or antigen-binding fragments of ANGPTL4, anti-$\alpha_v\beta_5$ antibodies or other antibodies described herein. Exemplary antibodies include, e.g., polyclonal, monoclonal, humanized, fragment, multispecific, heteroconjugated, multivalent, effecto function, etc., antibodies. Antibodies can be agonists or antagonists.

Polyclonal Antibodies

The antibodies of the invention can comprise polyclonal antibodies. Methods of preparing polyclonal antibodies are known to the skilled artisan. For example, polyclonal antibodies against ANGPTL4 are raised in animals by one or multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against ANGPTL4, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Typically, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies can be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that typically contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Typical myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against ANGPTL4. The binding specificity of monoclonal antibodies produced by hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In another embodiment, antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized and Human Antibodies

Antibodies of the invention can comprise humanized antibodies or human antibodies. A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a typical method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and Duchosal et al. *Nature* 355:258 (1992). Human antibodies can also be derived from phage-display libraries (Hoogenboom et al., *J. Mol. Biol.,* 227:381 (1991); Marks et al., *J. Mol. Biol.,* 222:581-597 (1991); Vaughan et al. *Nature Biotech* 14:309 (1996)).

Human antibodies can also be produced using various techniques known in the art, including phage display libraries (Hoogenboom and Winter, *J. Mol. Biol.,* 227:381 (1991); Marks et al., *J. Mol. Biol.,* 222:581 (1991)). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, K S, and Chiswell, D J., *Cur Opin in Struct Biol* 3:564-571 (1993). Several sources of V-gene segments can be used for phage display. For example, Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated, e.g., by essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905. The techniques of Cole et al. and Boerner et al. are also available for the preparation of human monoclonal antibodies (Cole et al., *Monoclonal Antibodies and Cancer Therapy,* Alan R. Liss, p. 77 (1985) and Boerner et al., *J. Immunol.,* 147(1):86-95 (1991)). Human antibodies may also be generated by in vitro activated B cells (see U.S. Pat. Nos. 5,567,610 and 5,229,275).

Antibody Fragments

Antibody fragments are also included in the invention. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science,* 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. SFv fusion proteins may be constructed to yield fusion of an effector protein at either the amino or the carboxy terminus of an sFv. See *Antibody Engineering,* ed. Borrebaeck, supra. The antibody fragment may also be a "linear antibody", e.g., as described in U.S. Pat. No. 5,641,870 for example. Such linear antibody fragments may be monospecific or bispecific.

Multispecific Antibodies (e.g., Bispecific)

Antibodies of the invention also include, e.g., multispecific antibodies, which have binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a cell antigen and the other arm directed against a cytotoxic trigger molecule such as anti-Fc-γRI/anti-CD15, anti-p185$^{HER2}$/Fc-γRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; BsAbs with one arm which binds specifically to an antigen on a cell and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. Fc-γRI, FcγRII or FcγRIII); BsAbs for use in therapy of infectious diseases such as anti-CD3/anti-herpes simplex virus (HSV), anti-T-cell receptor: CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the VEGF receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Heteroconjugate Antibodies

Bispecific antibodies include cross-linked or "heteroconjugate" antibodies, which are antibodies of the invention. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Multivalent Antibodies

Antibodies of the invention include a multivalent antibody. A multivalent antibody may be internalized (and/or catabolized) faster than a bivalent antibody by a cell expressing an antigen to which the antibodies bind. The antibodies of the invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Effector Function Engineering

It may be desirable to modify the antibody of the invention with respect to effector function, so as to enhance the effectiveness of the antibody in treating cancer, for example. For example, a cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced targeting activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

Immunoconjugates

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate). A variety of radionuclides are available for the production of radioconjugate antibodies. Examples include, but are not limited to, e.g., $^{212}$Bi, $^{131}$I, $^{131}$In, $^{90}$Y and $^{186}$Re.

Chemotherapeutic agents useful in the generation of such immunoconjugates have been described above. For example, BCNU, streptozoicin, vincristine, 5-fluorouracil, the family of agents known collectively LL-E33288 complex described in U.S. Pat. Nos. 5,053,394, 5,770,710, esperamicins (U.S. Pat. No. 5,877,296), etc. (see also the definition of chemotherapeutic agents herein) can be conjugated to the anti-ANGPTL4 or anti-angiogenesis antibodies or fragments thereof.

For selective destruction of a cell, the antibody may comprise a highly radioactive atom. A variety of radioactive isotopes are available for the production of radioconjugated anti-ANGPTL4 or fragments thereof. Examples include, but are not limited to, e.g., $^{211}$At, $^{131}$I, $^{125}$I, $^{90}$Y, $^{186}$Re, $^{188}$Re, $^{153}$Sm, $^{212}$Bi, $^{32}$P, $^{212}$Pb, $^{111}$In, radioactive isotopes of Lu, etc. When the conjugate is used for diagnosis, it may comprise a radioactive atom for scintigraphic studies, for example $^{99m}$tc or $^{123}$I, or a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $^{99m}$tc or $^{123}$I, $^{186}$Re, $^{188}$Re and $^{111}$In can be attached via a cysteine residue in the peptide. Yttrium-90 can be attached via a lysine residue. The IODOGEN method (Fraker et al *Biochem. Biophys. Res. Commun.* 80: 49-57 (1978) can be used to incorporate iodine-123. See, e.g., *Monoclonal Antibodies in Immunoscintigraphy* (Chatal, CRC Press 1989) which describes other methods in detail.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, sapaonaria officinalis inhibitor, gelonin, mitogellin, restrictocin, phenomycin, neomycin, and the tricothecenes. See, e.g., WO 93/21232 published Oct. 28, 1993.

Conjugates of the antibody and cytotoxic agent are made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208, 020) may be used.

Alternatively, a fusion protein comprising the anti-ANGPTL4 and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In certain embodiments, the antibody is conjugated to a "receptor" (such streptavidin) for utilization in cell pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In certain embodiments, an immunoconjugate is formed between an antibody and a compound with nucleolytic activity (e.g., a ribonuclease or a DNA endonuclease such as a deoxyribonuclease; Dnase).

Maytansine and Maytansinoids

The invention provides an antibody of the invention which is conjugated to one or more maytansinoid molecules. Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

For example, an anti-ANGPTL4 antibody or anti-$\alpha_v\beta_5$ antibody is conjugated to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. In one embodiment, maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., Cancer Research 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Typical coupling agents include N-succinimidyl-3-(2-pyridyldithio)propionate (SPDP) (Carlsson et al., Biochem. J. 173:723-737 [1978]) and N-succinimidyl-4-(2-pyridylthio) pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. The linkage is formed at the C-3 position of maytansinol or a maytansinol analogue.

Calicheamicin

Another immunoconjugate of interest comprises an anti-ANGPTL4 antibody or anti-$\alpha_v\beta_5$ antibody conjugated to one or more calicheamicin molecules. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated to is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

Liposomes and Nanoparticles

Polypeptides of the invention cane me formulated in liposomes. For example, antibodies of the invention may also be formulated as immunoliposomes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556. Generally, the formulation and use of liposomes is known to those of skill in the art.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the invention can be conjugated to the liposomes as described in Martin et al. J. Biol. Chem. 257: 286-288 (1982) via a disulfide interchange reaction. Nanoparticles or nanocapsules can also be used to entrap the polypeptides of the invention. In one embodiment, a biodegradable polyalkylcyanoacrylate nanoparticles can be used with the polypeptides of the invention.

Other Uses

The anti-ANGPTL4 antibodies have various utilities. For example, anti-ANGPTL4 antibodies may be used in diagnostic assays for ANGPTL4 or fragments of ANGPTL4, e.g., detecting its expression in specific cells, tissues, or serum, for disease detection, e.g., of the disorders described herein, etc. In one embodiment, ANGPTL4 antibodies are used for selecting the patient population for treatment with the methods provided herein. Various diagnostic assay techniques known in the art may be used, such as competitive binding assays, direct or indirect sandwich assays and immunoprecipitation assays conducted in either heterogeneous or homogeneous phases (Zola, *Monoclonal Antibodies: A Manual of Techniques*, CRC Press, Inc. (1987) pp. 147-158). The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. And Cytochem.*, 30:407 (1982).

Anti-ANGPTL4 antibodies also are useful for the affinity purification of ANGPTL4 from recombinant cell culture or natural sources. In this process, the antibodies against ANGPTL4 are immobilized on a suitable support, such a Sephadex resin or filter paper, using methods well known in the art. The immobilized antibody then is contacted with a sample containing the ANGPTL4 to be purified, and thereafter the support is washed with a suitable solvent that will remove substantially all the material in the sample except the ANGPTL4, which is bound to the immobilized antibody. Finally, the support is washed with another suitable solvent that will release the ANGPTL4 from the antibody.

Vectors, Host Cells and Recombinant Methods

The polypeptides of the invention can be produced recombinantly, using techniques and materials readily obtainable.

For recombinant production of a polypeptide of the invention, e.g., an ANGPTL4, an anti-ANGPTL4 antibody, or an anti-$\alpha_v\beta_5$ antibody, the nucleic acid encoding it is isolated and inserted into a replicable vector for further cloning (amplification of the DNA) or for expression. DNA encoding the polypeptide of the invention is readily isolated and sequenced using conventional procedures. For example, a DNA encoding a monoclonal antibody is isolated and sequenced, e.g., by using oligonucleotide probes that are capable of binding specifically to genes encoding the heavy and light chains of the antibody. Many vectors are available. The vector components generally include, but are not limited to, one or more of the following: a signal sequence, an origin of replication, one or more marker genes, an enhancer element, a promoter, and a transcription termination sequence.

Signal Sequence Component

Polypeptides of the invention may be produced recombinantly not only directly, but also as a fusion polypeptide with a heterologous polypeptide, which is typically a signal sequence or other polypeptide having a specific cleavage site at the N-terminus of the mature protein or polypeptide. The heterologous signal sequence selected typically is one that is recognized and processed (i.e., cleaved by a signal peptidase) by the host cell. For prokaryotic host cells that do not recognize and process the native polypeptide signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the polypeptide of the invention.

Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, typically primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding a polypeptide of the invention, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid Yrp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

Promotor Component

Expression and cloning vectors usually contain a promoter that is recognized by the host organism and is operably linked to a nucleic acid encoding a polypeptide of the invention. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldyhyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldyhyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription of polypeptides of the invention from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and typically Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the rous sarcoma virus long terminal repeat can be used as the promoter.

Enhancer Element Component

Transcription of a DNA encoding a polypeptide of this invention by higher eukaryotes is often increased by inserting an enhancer sequence into the vector. Many enhancer sequences are now known from mammalian genes (globin, elastase, albumin, α-fetoprotein, and insulin). Typically, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the polypeptide-encoding sequence, but is typically located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide of the invention. One useful transcription termination component is the bovine growth hormone polyadenylation region. See WO94/11026 and the expression vector disclosed therein.

Selection and Transformation of Host Cells

Suitable host cells for cloning or expressing DNA encoding the polypeptides of the invention in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. Typically, the *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide of the invention-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated polypeptides of the invention are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/−DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for polypeptide of the invention production and cultured in conventional nutrient media modified as appropriate for inducing promoters, selecting transformants, or amplifying the genes encoding the desired sequences.

Culturing the Host Cells

The host cells used to produce polypeptides of the invention may be cultured in a variety of media. Commercially available media such as Ham's F10 (Sigma), Minimal Essential Medium ((MEM), (Sigma), RPMI-1640 (Sigma), Dulbecco's Modified Eagle's Medium ((DMEM), Sigma), normal growth media for hepatocytes (Cambrex), growth media for pre-adipocytes (Cambrex), etc. are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Polypeptide Purification

When using recombinant techniques, a polypeptide of the invention, e.g., ANGPTL4, anti-ANGPTL4 antibody, or an anti-$\alpha_v\beta_5$ antibody can be produced intracellularly, in the periplasmic space, or directly secreted into the medium. Polypeptides of the invention may be recovered from culture medium or from host cell lysates. If membrane-bound, it can be released from the membrane using a suitable detergent solution (e.g. Triton-X 100) or by enzymatic cleavage. Cells employed in expression of a polypeptide of the invention can be disrupted by various physical or chemical means, such as freeze-thaw cycling, sonication, mechanical disruption, or cell lysing agents.

It may be desired to purify a polypeptide of the invention from recombinant cell proteins or polypeptides. The following procedures are exemplary of suitable purification procedures: by fractionation on an ion-exchange column; ethanol precipitation; reverse phase HPLC; chromatography on silica, chromatography on heparin SEPHAROSE™ chromatography on an anion or cation exchange resin (such as a polyaspartic acid column, DEAE, etc.); chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of polypeptides of the invention. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular polypeptide of the invention produced.

For example, an antibody composition prepared from the cells can be purified using, for example, hydroxylapatite chromatography, gel electrophoresis, dialysis, and affinity chromatography, with affinity chromatography being the typical purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification, e.g., those indicated above, are also available depending on the antibody to be recovered. See also, Carter et al., *Bio/*

*Technology* 10:163-167 (1992) which describes a procedure for isolating antibodies which are secreted to the periplasmic space of *E. coli*.

Covalent Modifications to Polypeptides of the Invention

Covalent modifications of a polypeptide of the invention, e.g., ANGPTL4, or polypeptide agonist or polypeptide antagonist, are included within the scope of this invention. They may be made by chemical synthesis or by enzymatic or chemical cleavage of the polypeptide, if applicable. Other types of covalent modifications of the polypeptide are introduced into the molecule by reacting targeted amino acid residues of the polypeptide with an organic derivatizing agent that is capable of reacting with selected side chains or the N- or C-terminal residues, or by incorporating a modified amino acid or unnatural amino acid into the growing polypeptide chain, e.g., Ellman et al. *Meth. Enzym.* 202:301-336 (1991); Noren et al. *Science* 244:182 (1989); and, & US Patent applications 20030108885 and 20030082575.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is typically performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to a polypeptide of the invention. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.*, pp. 259-306 (1981).

Removal of any carbohydrate moieties present on a polypeptide of the invention may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al. *Arch. Biochem. Biophys.* 259:52 (1987) and by Edge et al. *Anal. Biochem.*, 118:131 (1981). Enzymatic cleavage of carbohydrate moieties, e.g., on antibodies, can be achieved by the use of a variety of endo- and exo-glycosidases as described by Thotakura et al. *Meth. Enzymol.* 138:350 (1987).

Another type of covalent modification of a polypeptide of the invention comprises linking the polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Pharmaceutical Compositions

Therapeutic formulations of molecules of the invention, ANGPTL4, ANGPTL4 agonist or ANGPTL4 antagonist, used in accordance with the invention are prepared for storage by mixing a molecule, e.g., a polypeptide, having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or nonionic surfactants such as TWEEN™, PLURONICS™ or polyethylene glycol (PEG).

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980). See also Johnson et al., *Nat. Med.,* 2:795-799 (1996); Yasuda, *Biomed. Ther.,* 27:1221-1223 (1993); Hora et al., *Bio/Technology,* 8:755-758 (1990); Cleland, "Design and Production of Single Immunization Vaccines Using Polylactide Polyglycolide Microsphere Systems," in *Vaccine Design: The Subunit and Adjuvant Approach,* Powell and Newman, eds, (Plenum Press: New York, 1995), pp. 439-462; WO 97/03692, WO 96/40072, WO 96/07399; and U.S. Pat. No. 5,654,010.

In certain embodiments, the formulations to be used for in vivo administration are sterile. This is readily accomplished by filtration through sterile filtration membranes.

Sustained-release preparations may be prepared. Suitable examples of sustained-release preparations include semipermeable matrices of solid hydrophobic polymers containing a polypeptide of the invention, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), poly-lactic-coglycolic acid (PLGA) polymer, and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37EC, resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. See also, e.g., U.S. Pat. No. 6,699,501, describing capsules with polyelectrolyte covering.

It is further contemplated that a therapeutic protein agent of the invention (ANGPTL4, ANGPTL4 agonist or ANGPTL4 antagonist) can be introduced to a subject by gene therapy. Gene therapy refers to therapy performed by the administration of a nucleic acid to a subject. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. See, e.g., Ad-ANGPTL4-SiRNA described herein. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 (1986)). The oligonucleotides can be modified to enhance their uptake, e.g. by substituting their negatively charged phosphodiester groups by uncharged groups. For general reviews of the methods of gene therapy, see, for example, Goldspiel et al. *Clinical Pharmacy* 12:488-505 (1993); Wu and Wu *Biotherapy* 3:87-95 (1991); Tolstoshev *Ann. Rev. Pharmacol. Toxicol.* 32:573-596 (1993); Mulligan *Science* 260:926-932 (1993); Morgan and Anderson *Ann. Rev. Biochem.* 62:191-217 (1993); and May *TIBTECH* 11:155-215 (1993). Methods commonly known in the art of recombinant DNA technology which can be used are described in Ausubel et al. eds. (1993) *Current Protocols in Molecular Biology*, John Wiley & Sons, NY; and Kriegler (1990) *Gene Transfer and Expression, A Laboratory Manual*, Stockton Press, NY.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. For example, in vivo gene transfer techniques include but are not limited to, e.g., transfection with viral (typically retroviral) vectors and viral coat protein-liposome mediated transfection (Dzau et al., *Trends in Biotechnology* 11, 205-210 (1993)). For example, in vivo nucleic acid transfer techniques include transfection with viral vectors (such as adenovirus, Herpes simplex I virus, lentivirus, retrovirus, or adeno-associated virus) and lipid-based systems (useful lipids for lipid-mediated transfer of the gene are DOTMA, DOPE and DC-Chol, for example). Examples of using viral vectors in gene therapy can be found in Clowes et al. *J. Clin. Invest.* 93:644-651 (1994); Kiem et al. *Blood* 83:1467-1473 (1994); Salmons and Gunzberg Human *Gene Therapy* 4:129-141 (1993); Grossman and Wilson *Curr. Opin. in Genetics and Devel.* 3:110-114 (1993); Bout et al. *Human Gene Therapy* 5:3-10 (1994); Rosenfeld et al. *Science* 252:431-434 (1991); Rosenfeld et al. *Cell* 68:143-155 (1992); Mastrangeli et al. *J. Clin. Invest.* 91:225-234 (1993); and Walsh et al. *Proc. Soc. Exp. Biol. Med.* 204:289-300 (1993).

In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

Dosage and Administration

Dosages and desired drug concentrations of pharmaceutical compositions of the invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In *Toxicokinetics and New Drug Development*, Yacobi et al., Eds., Pergamon Press, New York 1989, pp. 42-96.

Depending on the type and severity of the disease, about 1 µg/kg to 50 mg/kg (e.g. 0.1-20 mg/kg) of ANGPTL4, ANGPTL4 agonist or ANGPTL4 antagonist, is an initial candidate dosage for administration to the patient, whether, for example, by one or more separate administrations, or by continuous infusion. When in vivo administration of an ANGPTL4 or, agonist or antagonist thereof, is employed, normal dosage amounts may vary from about 10 ng/kg to up to 100 mg/kg of mammal body weight or more per day, preferably about 1 mg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue. For repeated administrations over several days or longer, depending on the condition, the treatment is sustained until a desired suppression of disease symptoms occurs. However, other dosage regimens may be useful. Typically, the clinician will administered a molecule(s) of the invention until a dosage(s) is reached that provides the required biological effect. The progress of the therapy of the invention is easily monitored by conventional techniques and assays.

The therapeutic composition of the invention can be administered by any suitable means, including but not limited to, parenteral, subcutaneous, intraperitoneal, intrapulmonary, intracerobrospinal, subcutaneous, intra-articular, intrasynovial, intrathecal, oral, topical, and intranasal administration. Parenteral infusions include intramuscular, intravenous, intraarterial, intraperitoneal, or subcutaneous administration. In addition, the therapeutic composition is suitably administered by pulse infusion, particularly with declining doses of the antibody. In certain embodiments, the therapeutic composition is given by injections, e.g., intravenous or subcutaneous injections, depending in part on whether the administration is brief or chronic.

As described herein, ANGPTL4, ANGPTL4 agonist or ANGPTL4 antagonist, can be combined with one or more therapeutic agents. The combined administration includes coadministration, using separate formulations or a single pharmaceutical formulation, and consecutive administration in either order. Use of multiple agents are also included in the invention. For example, an ANGPTL4 or ANGPTL4 agonist may precede, follow, alternate with administration of the additional therapeutic agent, or may be given simultaneously therewith. In one embodiment, there is a time period while both (or all) active agents simultaneously exert their biological activities.

In certain embodiments, the treatment of the invention involves the combined administration of an ANGPTL4 antagonist and one or more therapeutic agent. The invention also contemplates administration of multiple inhibitors. The combined administration includes coadministration, using separate formulations or a single pharmaceutical formulation, and consecutive administration in either order. For example, an ANGPTL4 antagonist may precede, follow, alternate with administration of the additional therapeutic agent, or may be given simultaneously therewith. In one embodiment, there is a time period while both (or all) active agents simultaneously exert their biological activities.

For the prevention or treatment of disease, the appropriate dosage of ANGPTL4, ANGPTL4 agonist or ANGPTL4 antagonist, will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments. In a combination therapy regimen, the compositions of the invention are administered in a therapeutically effective amount or a therapeutically synergistic amount. As used herein, a therapeutically effective amount is such that co-administration of ANGPTL4, ANGPTL4 agonist or ANGPTL4 antagonist, and one or more other therapeutic agents, or administration of a composition of the invention, results in reduction or inhibition of the targeting disease or condition. A therapeutically synergistic amount is that amount of ANGPTL4, ANGPTL4 agonist or ANGPTL4 antagonist, and one or more other therapeutic agents, e.g., described herein, necessary to synergistically or significantly reduce or eliminate conditions or symptoms associated with a particular disease.

Articles of Manufacture

In another embodiment of the invention, an article of manufacture containing materials useful for the methods and treatment of the disorders described above is provided. The article of manufacture comprises a container, a label and a package insert. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an ANGPTL4, ANGPTL4 agonist or ANGPTL4 antagonist. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, and syringes. Optionally, a set of instructions, generally written instructions, is included, which relates to the use and dosage of ANGPTL4, agonist or antagonist for a disorder described herein. The instructions included with the kit generally include information as to dosage, dosing schedule, and route of administration for the treatment the disorder. The containers of ANGPTL4, ANGPTL4 agonist or ANGPTL4 antagonist may be unit doses, bulk packages (e.g., multi-dose packages), or sub-unit doses.

Deposit of Materials

The following material has been deposited with the American Type Culture Collection, 10801 University Boulevard, Manassas, Va. 20110-2209, USA (ATCC):

| Material | ATCC Deposit No. | Deposit Date |
|---|---|---|
| ANGPTL4 (NL2-DNA 22780-1078) | 209284 | Sep. 18, 1997 |

The deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

Example 1

ANGPTL4 Induces Cell-Adhesion and Proliferation of Human Hepatocytes

Generation of Adenoviral Vectors and Transduction:

Adenoviral constructs have been constructed by cloning the Not1-Not1 cDNA insert into the polylinker site of the Ad-easy vector construction kits from Stratagene (LaJolla, Calif.), essentially as described by the manufacturer. See, e.g., Hesser et al., *Blood*, 104(1):149-158 (2004).

Generation of hAngptl4(23-406) (PUR9384), mAngptl4 (184-410)-IgG (PUR9388) and mAngptl4(23-410) (PUR9452) Single Flag Tagged Protein:

Harvested cell culture fluid was passed overnight onto anti-flag M2 resin (Sigma#A-2220). The column was washed to base-line with PBS then eluted with 50 mM Na Citrate pH3.0. This volume was concentrated on Amicon-15 10,000MWCO (Millipore #UFC901024). The final step was dialysis into 1 mM HCl/Super Q $H_2O$ and 0.2 um filtration. A 4-20% tris/glycine (Invitrogen#EC6028box) SDS page gel+/−10 mM DTT was used to determine purity. Correct proteins were identified by either Mass Spec or Edman's n-terminal sequencing.

Generation of hAngptl4(184-406)-IgG (PUR 9441) n-Terminal Flag Tag Followed in Series by an n-Terminal hu Fc Tag:

Harvested cell culture fluid was passed overnight onto ProSep A (Amersham #113111835). The column was washed to base-line with PBS. Then a four column volume 0.5M TMAC/PBS pH 7.5 wash step was followed by a PBS wash to base line. The elution step was a 50 mM Na Citrate pH 3.0 bump. This volume was concentrated on Amicon-15 10,000MWCO (Millipore #UFC901024). The final step was dialysis into 1 mM HCl/Super Q $H_2O$ and 0.2 um filtration. A 4-20% tris/glycine (Invitrogen#EC6028box) SDS page gel+/−10 mM DTT is used to determine purity. Correct proteins were identified by either Mass Spec or Edman's n-terminal sequencing. Recombinant proteins can also be made using standard techniques known in the art.

Generation of Ad-ANGPTL4-SiRNA:

4 potential ANGPTL4-SiRNA molecules (Qiagen) were generated based on the full length hANGPTL4 sequence. One ANGPTL4-SiRNA was selected based on the ability of the SiRNA to inhibit hANGPTL4 expression. It targeted the following DNA target sequence GTGGCCAAGCCTGC-CCGAAGA (SEQ ID NO:3) of ANGPTL4, e.g. r(GGC-CAAGCCUGCCCGAAGAUU) (SEQ ID NO:4) and/or r(UCUUCGGGCAGGCUUGGCCAC) (SEQ ID NO:5). The SiRNA was cloned into CMVpShuttle-H1.1 transfer vector with an RNA promoter, e.g., H1 promoter (GenScript). The SiRNA expression cassette was then cloned to generate an adenoviral AdhANGPTL4-SiRNA construct. Adenoviral constructs have been constructed by cloning the Not1-Not1 cDNA insert into the polylinker site of the Ad-easy vector construction kits from Stratagene (LaJolla, Calif.), essentially as described by the manufacturer. See e.g., Hesser et al., *Blood*, 104(1):149-158 (2004).

Expression of ANGPTL4 was verified by Western blotting analysis using an anti-FLAG antibody. One strongly expressing clone was selected and titers were amplified according to the manufactures instruction. Viral preparations were purified by CsCl centrifugation and tested for revertants by PCR. Viral titers were determined by 96 well cell lysis experiments according to the manufacturers instructions. These vectors, along with the supplied pShuttleCMV-lacZ, were recombined, in BJ5183 electro competent bacteria with the AdEasy vector containing the Ad5 genome deleted for E1 and E3 regions. Primary viral stocks were prepared by transiently transfecting the recombined AdEasy plasmids into host HEK293 cells. Adenovirus stocks were further amplified in HEK293 cells and purified using CsCl gradient purification method as described by the manufacturer. Adenovirus working titers were obtained by Elisa assay.

Generation of mANGPTL4:

293 cells were transiently transfected with a construct which contained a nucleic acid encoding the full length mANGPTL4 (1-410). mANGPTL4 was purified from the supernatant and used for experiments.

Cell Adhesion of Hepatocytes:

The ability of ANGPTL4 to induce cell adhesion of primary hepatocytes was evaluated in 96-well plates. Plates were coated with murine Angptl4 subsequence 23-410, fibronectin or a control protein NL4 at various concentrations, e.g., no coating, 0.3 µg/ml, 3.0 µg/ml or 30 µg/ml in 60 µl at 4° C. overnight. Excess protein was removed and coated wells were blocked with 200 µl of 3% BSA in PBS for 37° C. for 1½ hours. After incubation, the supernatant was aspirated and washed once with PBS.

The primary human hepatocytes were prepared and grown in normal growth medium (Cambrex). The cells were washed 3 times with PBS. The cells were trypsinized followed by a trypsin neutralization solution (Clonetics). The cells were then resuspended in normal growth medium (Cambrex). Cells were seeded at $1.5 \times 10^4$ cells/well in 200 µl total volume. The cells were split in 5% serum 24 hours before dosing. Cells were incubated in wells for 37° C. for 2 hours. The supernatant was removed. Cell attachment was measured using a crystal violet assay. 50 µl of 10% formalin solution was added to well and fixed for 10 minutes. The cells were washed carefully once with PBS. 50 μl of 0.5% Crystal violet solution was added that was filtered before use. Solution was incubated in the wells for 30 minutes or more at room temperature. Wells were washed 3 to 5 times with PBS. PBS was removed from the wells and dried. The 96 well plate was read at an $OD_{550}$. See FIG. 4. The PNAG method of Landegren can also be used. See, Landegren, U. (1984) *J. Immunol. Methods* 67:379-388. As seen in FIG. 4, recombinant mAngptl4 (23-410) induces cell-adhesion of primary hepatocytes in vitro.

Proliferation of Hepatocytes:

The proliferation effect of Angptl4 on primary human hepatocytes was examined. Adenoviral constructs of Ad-human (h)Angptl4, Ad-LacZ and Ad-Angptl3 were prepared. See, e.g., Hesser et al, *Blood* 104(1):149-158 (2004). Primary human hepatocytes were transduced with either a construction comprising the adenovirus-Angptl4 construct (Ad-Angptl4), the adenovirus-LacZ construct (Ad-LacZ) as a control or the adenovirus-Angptl3 construct (Ad-Angptl3) at the multiplicity of infection (MOI) of 10, 100 and 1000. After 5 days of growing the hepatocytes in normal hepatocyte growth medium (Cambrex), the cells were counted. As indicated in FIG. 5, the Ad-Angptl4 induces hepatocyte proliferation in vitro at MOI of 10.

Example 2

ANGPTL4 Induces Proliferation of Pre-Adipocytes

Pre-Adipocyte Proliferation:

The ability of ANGPTL4 to induce pre-adipocyte proliferation was evaluated. Human pre-adipocytes (visceral or subcutaneous) were grown on 6 well dishes (Falcon, Primaria) by splitting cells at a density of 30,000 cells/well in a volume of 3 ml of growth medium containing serum (preadipocyte growth medium (Cambrex)). 500 μl of COS cell condition medium from COS cells that were transduced with adenoviral constructs, e.g., Ad-LacZ (4), Ad-human (h) Angptl4 (23-406) (5) or Ad-human (h)Angptl3 (full length protein) (6), or recombinant proteins (recombinant murine Angptl4 (23-410) (2); IgG-mAngptl4 (184-410) (3) or nothing added (1) at the following concentrations (rmAngptl4 (23-410) (5 μg/ml); IgG-mAngptl4 (5 μg/ml)) were added directly after seeding the cells. The cells were grown for 5 days at 37° C. in 5% $CO_2$ incubator. The cells were trypsinized with 500 μl of 1×trypsin for 3 to 5 minutes. The cell mixture (0.5 ml) was pipetted into 9.5 ml of isotonic buffer solution and counted in a cell counter vial (considering the dilution factor of 20). As indicated in FIG. 6, Panel A, both recombinant murine Angptl4 (23-410) (2) and conditioned COS cell media containing hAngptl4 (23-406) (SEQ ID NO: 8) (5) induces primary human visceral pre-adipocyte proliferation. FIG. 6, Panel B illustrates that both recombinant murine Angptl4 (23-410) (2) and conditioned COS cell media containing hAngptl4(23-406) (SEQ ID NO: 8) (5) induces primary human subcutaneous pre-adipocyte proliferation.

FACS Analysis of Angptl4 Binding to Human Primary Adipocytes:

Binding of ANGPTL4 to human primary adipoctyes was examined by FACS analysis. Primary human subcutaneous adipocytes were plated in 10 cm cultured dishes at 500,000 to $1 \times 10^6$ cells/sample well. The cells were split the day before the FACS. The cells were washed once with PBS and then 10 ml of 20 mM EDTA in PBS was added and incubated for 10 to 20 minutes. After 20 minutes, cells were scraped from plate. 10 ml of 5% FCS in PBS was added and cells were transferred to a 50 ml Falcon tube. The cells were spun down at 1.8 K rpm for 5 minutes at 4° C. The supernatant was removed and the cells were resuspended in 1 ml of 5% FCS in PBS. 100 μl of cell suspension was distributed into a 5 ml FACS tubes containing 1 μg of protein and incubated for 30 minutes or greater on ice. The following proteins were used: mAngptl4 (23-410), PUR 9452, 0.428 mg/ml (2 μl/sample); hAngptl4 (23-406) (SEQ ID NO: 8), PUR 9384, +/−90 μg/ml (10 μl/sample); mAngptl4 (184-410)-IgG, PUR 9388, 8.5 mg/ml (0.2 μl/sample); hAngptl4 (184-406)-IgG, PUR 9441, 1.5 mg/ml (1 μl/sample); and control FLAG-BAP (Sigma) 0.1 mg/ml (2 μl/sample). After incubation, tubes were filled with 5 ml of 5% FCS in PBS on ice. The cells were spun down for 5 minutes at 2K rpm. The supernatant was removed. Anti-FLAG-FITC antibody (Sigma) was added (2 μl of antibody (100 μg/ml stock) and incubated on ice for 5 minutes or greater. The final antibody concentration was 1 μg/ml. 5 ml of 5% FCS in PBS was added and cells were spun down 5 minutes at 1.8 K rpm at 4° C. The supernatant was removed and cells were resuspended in 0.25 ml PBS with 5% FCS on ice. 0.05% sodium azide may be also present to prevent receptor internalization. 1 μl of 1:50 diluted stock of propidium iodide (PI) was added per sample. The cells were then subject to FACS. As indicated in FIG. 7, under these conditions, both human Angptl4 forms, rhAngptl4 (23-406), and rhIgG-hAngptl4 (184-406) bind more efficiently to subcutaneous adipocytes compared to the murine ortholog.

Example 3

Angptl4 Induces Migration of Primary Human Subcutaneous Pre-Adipocytes

Angptl4 Induces Cell Migration:

We examined Angptl4 ability to induce cell migration of primary human subcutaneous pre-adipocytes. Cell motility was measured as described (see, e.g., Camenish et al., *J. Biol. Chem.*, 277(19):17281-17290 (2002)) using HTS Multiwell tissue culture inserts with 3 μm pore size (Becton Dickinson, NJ). hANGPTL4 (1-406) (SEQ ID NO: 2) was diluted in 50/50/0.1% BSA to 5, 1 and 0.2 μg/ml. As a positive control, membranes were incubated with either 10% fetal calf serum (FCS) containing medium or 0.1 μg/ml of recombinant human PDGF-BB (R&D Systems). PBM/0.1% BSA was used as a negative control. Primary human adipocytes were washed three times with PBS, harvested and suspended at about $2-5 \times 10^5$ cells/ml in PBM/0.1% BSA. The following cell preparations were tested, where ANGPTL4 is indicated as NL2.

| | Adipocyte | |
|---|---|---|
| FIG. 8, Panel A | NL2 5 μg | PBM/0.1% BSA |
| | NL2 0.5 μg | +10% FBS |
| | NL2 0.2 μg | +10% FBS |
| | PDGF-BB 0.1 μg | PBM/0.1% BSA |
| FIG. 8, Panel B and C | NL2 6.0 μg | PBM/0.1% BSA |
| | NL2 1.5 μg | PBM/0.1% BSA |
| | NL2 0.375 μg | PBM/0.1% BSA |
| | PDGF-BB 0.1 μg | PBM/0.1% BSA |

The preparations were added to the bottom chamber and the preparations were incubated at 37° C. for 19 hours.

The cell suspension (250 μl) was added to the upper chamber and the cells were allowed to migrate overnight at 37° C. in a 5% $CO_2$ humidified incubator. After incubation, medium was aspirated from the both top and bottom chambers, and cells that had migrated to the lower surface of the membrane were fixed with methanol (400 µl of MeOH for 30 minutes at 4° C., remove MeOH and air dry for 40 minutes) and stained with YO-PRO-1 iodide (Molecular Probes, OR) (400 µl YO-PRO-1 iodide at 10 µm (1:100 from 1 mM stock)). Migration results are quantitated in terms of the average number of cells/microscopic field at a 20-fold magnification using the Open/ab software (Improvision, MA). As seen in FIG. 8, Panel A, hAngptl4 added to primary human subcutaneous pre-adipocytes induces them to migrate. FIG. 8, Panel B illustrates migration at 7 hours. FIG. 8, Panel C graphically illustrates the migration of adipocytes after 7 hours of treatment with either no serum (1), 10% fetal calf serum (FCS) (2), PDGF-BB (3), mANGPTL4 (4).

Example 4

Variant of Angptl4

A variant ANGPTL4 was made using a standard mutagenesis kit (e.g., QuikChange XL Site-Directed Mutagenesis Kit (Invitrogen, Carlsbad, Calif.)) following the manufacturer's protocol. Two amino acid substitutions were made in the human ANGPTL4 sequence (see, e.g., FIG. 2). The substitutions were at position 162 and 164 (R162G and R164E) (SEQ ID NO: 28), resulting in a RKR to GKE change. ANGPTL4 protein (L280 plasmid, aa 1-406 (SEQ ID NO: 2)) or variant ANGPTL4 was isolated from the supernatant of transiently transfected COS-7 cells. For purification, the supernatant was loaded on a nickel column. Protein was detected by Western blot with an anti-FLAG-HRP antibody. See, FIG. 3, Panel B. When the substitutions were made and the variant ANGPTL4 was compared to native or wild type ANGPTL4 protein, the variant ANGPTL4 was found to have a higher molecular weight than native ANGPTL4 by Western blotting. The substitution from RKR to GKE at position 162 and 164 of the native protein prevented proteolytic degradation of ANGPTL4.

Example 5

Angptl4 Binds to Integrin αVβ5

Angiopoietins are secreted factors that regulate angiogenesis by binding to the endothelial cell specific tyrosine kinase receptor Tie2 via their fibrinogen (FBN)-like domain. The coiled-coil domain present in the family of secreted ligands was found to be necessary for ligant oligomerization (see, e.g., Procopio et al., *J. Biol. Chem.*, 274:30196-201 (1999)).

Similar to the angiopoietins, ANGPTL3 and ANGPTL4 are secreted glycoproteins, each consisting of an N-terminal signal peptide, followed by a coiled-coil domain and a C-terminal FBN-like domain. It was determined that ANGPTL3 binds to $\alpha_v\beta_3$ through the FBN-like domain. We determined that ANGPTL4 binds to $\alpha_v\beta_5$. 293-1953 cell line that is stably transfected with $\alpha_v\beta_5$ integrin was tested for the ability to bind or adhere to ANGPTL4 coated plates. Cells were harvested and diluted to $10^5$ cells/ml in serum-free medium containing, PBS, 1% BSA, 1 mM $CaCl_2$ and 1 mM $MgCl_2$. Cells were preincubated with or without anti-integrin $\alpha_v\beta_5$ antibodies (MAB 1961 (Chemicon, Temecula, Calif.)) or peptides for 15 minutes at 37° C. Recombinant mANGPTL4, BSA or vitronectin (1 µg, 3 µg, 10 µg, or 30 µg/ml) were coated on to Nunc Maxisorp 96-well flat-bottomed microtiter plates overnight at 4° C. and blocked with 200 µl of 3% BSA in phosphate buffer saline (PBS), pH 7.4, for 1.5 hours at 37° C. Cell suspensions ($5\times10^4$ cells/100 µl/well ($5\times10^5$/ml)) were added to the coated wells and the plates were incubated at 37° C. for 5.5 hours. Non-adherent cells were removed by PBS washes and cell attachment was measured by adding 200 µl of CyQuant GD Dye (Molecular Probes (Invitrogen detection Technologies (Carlsbad, Calif.)) (1:400)/cell lysis buffer and incubated for 2-5 minutes. The sample fluorescence was measured using 480 nm excitation and 520 nm emission maxima. The PNAG method of Lanndegren can be used (see, e.g., Landegren, J. Immunol. Methods, 67:379-388 (1984)). Cells expressing $\alpha_v\beta_5$ displayed adherence to ANGPTL4 and vitronectin (USBiological, Swampscott, Mass.), a positive control, compared to BSA, a negative control. See FIG. 9, Panel A.

To determine whether the $\alpha_v\beta_5$ integrin was sufficient to mediate ANGPTL4 cell adhesion, blocking antibodies were tested for their ability to inhibit the adhesion in the cell adhesion assay. Functional blocking antibodies (anti-$\alpha_v\beta_5$ antibody (MAB 1961 (Chemicon, Temecula, Calif.)) or anti-hANGPTL4 antibodies) were added to 293-1953 cells prior to incubation with the protein coated (BSA (1), vitronectrin (2) or ANGPTL4(3)) wells. See See FIG. 9, Panel B. Anti-$\alpha_v\beta_5$ and anti-ANGPTL4 antibodies abolished ANGPTL4 cell adhesion activity.

Additional experiments were performed to confirm that ANGPTL4 binds $\alpha_v\beta_5$. ELISA experiments were performed to detect if mANGPTL4, IgG-hANGPTL4-Nterminal (1-183) and/or IgG-hANGPTL4-Cterminal (184-406) binds to $\alpha_v\beta_5$ (USBiological, 37K, Swampscott, Mass.) coated plates. 100 µl/well of integrin $\alpha_v\beta_5$ diluent (1 µg/ml coating buffer (50 mM carbonate/bicarbonate, pH 9.6)) with coating buffer was incubated overnight at 4° C. The plates were washed three times with wash buffer (PBS, pH 7.4, 0.05% Tween-20), and 100 µl/well of blocking buffer (PBS, pH 7.4, 0.5% BSA) was added for 1 hour at room temperature with gentle agitation. Various amounts (0, 0.070 µg, 0.22 µg, 0.66 µg, 2 µg, or 6 µg) of samples, mANGPTL4, IgG-hANGPTL4-Nterminal (1-183) and/or IgG-hANGPTL4-Cterminal (184-406), were prepared in sample buffer (0.5% BSA, 50 mM Tris, pH 7.4, 0.05% Tween 20, 1 mM $MnCl_2$, 50 µM $CaCl_2$, 50 µM $MgCl_2$, 100 mM NaCl) and incubated for 30 minutes. Samples were added to plates (100 µl/well in the amounts incubated above) and incubated for 2 hours at room temperature with gentle agitation. Plates were washed with buffer and 100 µl/well anti-Flag-horseradish peroxidase (HRP) (100 ng/ml) (Jackson, #109-036-098) in assay buffer (PBS, pH7.4, 0.5% BSA, 0.05% Tween 20) was added and incubated for 1 hour at room temperature with gentle agitation. The plates were washed. 100 µl/well of tetramethylbenzidine (TMB) (Moss, Inc.) was added and incubated in the plates until good color was developed at room temperature. 100 µl/well Stop solution (1 M $H_3PO_4$) was added to stop the reaction. The plates were read at 630 nm. mANGPTL4, IgG-hANGPTL4-Nterminal and IgG-hANGPTL4-C-terminal bound to $\alpha_v\beta_5$ coated plates, although slightly more of IgG-hANGPTL4-Cterminal bound to the plates. See, FIG. 9, Panel C.

Anti-ANGPTL4 antibodies inhibit binding of ANGPTL4 to $\alpha_v\beta_5$ coated plates. ELISA experiments were performed. 100 µl/well of integrin $\alpha_v\beta_5$ diluent (1 µg/ml coating buffer (50 mM carbonate/bicarbonate, pH 9.6)) with coating buffer was incubated overnight at 4° C. The plates were washed three times with wash buffer (PBS, pH 7.4, 0.05% Tween-20), and 100 µl/well of blocking buffer (PBS, pH 7.4, 0.5% BSA) was added for 1 hour at room temperature with gentle agitation. 0.6 µg to 6.0 µg of samples, mANGPTL4, IgG-hANGPTL4-Nterminal (1-183) and/or IgG-hANGPTL4-Cterminal (183-406), in sample buffer (0.5% BSA, 50 mM Tris, pH 7.4, 0.05% Tween 20, 1 mM $MnCl_2$, 50 µM $CaCl_2$, 50

μMMgCl$_2$, 100 mM NaCl) were incubated with anti-AN-GPTL4 antibodies (1.5 μg) or anti-Dscr (1.5 μg) for 30 minutes. After incubation, 100 μl/well of sample+/−antibody was incubated with the plates for 2 hours at room temperature with gentle agitation. Plates were washed with buffer and 100 μl/well anti-Flag-HRP (100 ng/ml) in assay buffer (PBS, pH7.4, 0.5% BSA, 0.05% Tween 20) was added and incubated for 1 hour at room temperature with gentle agitation. The plates were washed and 100 μl/well of TMB was added and incubated in the plates until good color was developed at room temperature. 100 μl/well Stop solution (1 M H$_3$PO$_4$) was added to stop the reaction. The plates were read at 630 nm. Anti-ANGPTL4 antibodies reduced the amount of mANGPTL4, IgG-hANGPTL4-Nterminal and IgG-hANGPTL4-Cterminal binding to the $\alpha_v\beta_5$ coated plates compared to anti-Dscr antibody, 5G7 monoclonal antibody or medium. See, FIG. 9, Panel D.

In another experiment, binding of ANGPTL4 and integrin $\alpha_v\beta_5$ was shown by ELISA. In this experiment, 80 μl/well of hANGPTL4-C terminal, vitronectin or BSA (5 μg/ml) was added to plates in coating buffer (50 mM carbonate/bicarbonate, pH 9.6) and incubated overnight at 4° C. The plates were washed (wash buffer: PBS, pH 7.4, 0.05% Tween-20) and 100 μl/well of blocking buffer (PBS, pH 7.4, 0.5% BSA) with either media, anti-hANGPTL4 antibodies (15 μg/100 μl), or anti-Dscr antibodies (15 μg/100 μl) was added and incubated for 1 hour at room temperature with gentle agitation. The plates were washed and $\alpha_v\beta_5$ 100 μl (3-9 μg/ml) was added and incubated for 2 hours at room temperature with gentle agitation. The plates were washed and 1 μg/ml (1:1000) of anti-$\alpha_v\beta_5$ antibody (Chemicon) (5 μg/100 μl) was added in assay buffer (PBS, pH7.4, 0.5% BSA, 0.05% Tween 20) and incubated for 1 hour at room temperature with gentle agitation. After incubation, the plates were washed and 100 μl/well horseradish peroxidase (HRP) anti-mouse (1:5000) was added in assay buffer. The plates were washed and 100 μl/well tetramethylbenzidine (TMB) was added and incubated at room temperature until there was good color development. The reaction was stopped with 100 μl/well 1 M H$_3$PO$_4$ and plates were read at 630 nm. $\alpha_v\beta_5$ binds to ANGPTL4 (lane 1) and vitronectrin (lane 4) coated plates. The binding is blocked with an anti-ANGPTL4 antibodies (lane 2) but not when a control antibody anti-Dscr is used (lane 3) or a control protein is coated on the plates (lane 5). See, FIG. 9, Panel E.

Hence, these findings demonstrate that recombinant ANGPTL4 binds specifically to the $\alpha_v\beta_5$ integrin.

Example 6

Angptl4 Increases Triglycerides in a Mouse when Injected Intravenously

Triglycerides levels were determined in C57B1-6 mice injected with various adenovirus constructs that include ANGPTL4. C57B1-6 mice were injected intravenously in the tail with either (1) adenovirus GFP construct, (2) adenovirus Gd construct, (3) adenovirus ANGPTL4 (1-406) construct, (4) adenovirus ANGPTL4 (1-183) construct, (5) adenovirus ANGPTL4 (184-406) construct, (6) adenovirus ANGPTL4 variant construct; (7) adenovirus ANGPTL4 (1-408) construct and (8) adenovirus control construct. Triglycerides levels in (mg/dl) were measured from blood samples from the mice, seven days after injection. As seen in FIG. 10, the ANGPTL4 N-terminal construct (1-183) has the most pronounced affect on triglyceride levels along with full length ANGPTL4 construct and the ANGPTL4 variant construct.

Example 7

Generation and Analysis of Mice Comprising an ANGPTL4 Gene Disruption

To investigate the role of an ANGPTL4, disruptions in an ANGPTL4 gene were produced by homologous recombination. Specifically, transgenic mice comprising disruptions in ANGPTL4 gene (i.e., knockout mice) were created by either gene targeting or gene trapping. Mutations were confirmed by southern blot analysis to confirm correct targeting on both the 5' and 3' ends. Gene-specific genotyping was also performed by genomic PCR to confirm the loss of the endogenous native transcript as demonstrated by RT-PCR using primers that anneal to exons flanking the site of insertion. Targeting vectors were electroporated into 129 strain ES cells and targeted clones were identified. Targeted clones were microinjected into host blastocysts to produce chimeras. Chimeras were bred with C57 animals to produce F1 heterozygotes. Heterozygotes were intercrossed to produce F2 wildtype, heterozygote and homozygote cohorts which were used for phenotypic analysis. Rarely, if not enough F1 heterozygotes were produced, the F1 hets were bred to wildtype C57 mice to produce sufficient heterozygotes to breed for cohorts to be analyzed for a phenotype. All phenotypic analysis was performed from 12-16 weeks after birth.

Results

Generation and Analysis of Mice Comprising ANGPTL4 Gene Disruptions:

In these knockout experiments, the gene encoding ANGPTL4 (PRO197 polypeptide designated as DNA 22780-1078; UNQ171) was disrupted. The gene specific information for these studies is as follows: the mutated mouse gene corresponds to nucleotide reference: NM_020581. ACCESSION:NM_020581 NID:10181163; or *Mus musculus* angiopoietin-like 4 (Angptl4); protein reference: Q9Z1P8. ACCESSION:Q9SZ1P9 NID; or *Mus musculus* (Mouse). NG27 (HEPATIC ANGIOPOIETIN-RELATED PROTEIN) (HYPOTHETICAL PROTEIN 425018-1) (FIBRINOGEN/ANGIOPOIETIN-RELATED PROTEIN) (ANGIOPOIETIN-LIKE PROTEIN) (ANGIOPOIETIN-LIKE 4). MOUSESTRNRDB; the human gene sequence reference: NM_139314. ACCESSION: NM_139314 NID:21536397 *Homo sapiens* angiopoietin-like 4 (ANGPTL4); the human protein sequence corresponds to reference: Q9BY76. ACCESSION:Q9BY78 NID: or *Homo sapiens* (Human). Angiopoietin-related protein 3 precursor (Angiopoietin-like 4) (Hepatic fibrinogen/angiopoietin-related protein) (HFARP) (Angiopoietin-like protein PP1158). HUMANSTRNRDB.

The disrupted mouse gene is Angptl4 (angiopoietin-like 4), which is the ortholog of human ANGPTL4. Aliases include those described herein and BK89, Bk89, FIAF, NG27, Ng27, HFARP, Farp-pending, fibrinogen/angiopoietin-related protein, major histocompatibility complex region NG27, ARP4, PGAR, PPARG, PP1158, ANGPTL2, fasting-induced adipose factor, PPARG angiopoietin related protein, hepatic angiopoietin-related protein, and hepatic fibrinogen/angiopoietin-related protein.

Targeted or gene trap mutations were generated in strain 129SvEVBrd-derived embryonic stem cells (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example, when very few F1 mice were obtained from the chimera, F1 heterozygous mice were crossed to 129SvEVBrd/C57 hybrid mice to yield additional heterozygous animals for the intercross to generate the F2 mice. Phenotypic analysis was performed on mice from this generation as described below.

|  | wt | het | hom | Total |
|---|---|---|---|---|
| Observed | 18 | 38 | 11 | 67 |
| Expected | 16.75 | 33.5 | 16.75 | 67 |

Chi-Sq. = 2.76
Significance = 0.26294 (hom/n) = 0.16
Avg. Litter Size = 7

Retroviral insertion (OST) occurred disrupting the gene between coding exons 2 and 3 (NCBI accession NM_020581.1)

Wild-type expression of target gene was detected in embryonic stem (ES) cells and in all adult tissue samples tested by RT-PCT, except tail. RT-PCR analysis revealed that the transcript was absent in the (−/−) mouse analyzed.

1. Phenotypic Analysis

Overall Phenotypic Summary:

Mutation of the gene encoding the ortholog of human angiopoietin-like 4 (ANGPTL4) resulted in decreased cholesterol and triglyceride levels in (−/−) mice. In addition, the male (−/−) mice exhibited an enhanced glucose tolerance in Glucose Tolerance Test. The mutant (−/−) mice also exhibited immunological abnormalities including elevated mean serum IgM levels and mean absolute neutrophil counts when compared with their (+/+) littermates. Transcript was absent by RT-PCR.

Cardiovascular Phenotypic Analysis/Metabolism-Blood Chemistry:

In the area of cardiovascular biology, phenotypic testing was performed to identify potential targets for the treatment of cardiovascular, endothelial or angiogenic disorders such as hypertension, atherosclerosis, heart failure, stroke, various coronary artery diseases, dyslipidemias such as high cholesterol (hypercholesterolemia) and elevated serum triglycerides (hypertriglyceridemia), cancer and/or obesity. The phenotypic tests include the measurement of serum cholesterol and triglycerides. In addition, blood chemistry phenotypic analysis also included glucose tolerance tests to measure insulin sensitivity and changes in glucose metabolism. Abnormal glucose tolerance test results are indicative of but may not be limited to the following disorders or conditions: Diabetes Type 1 and Type 2, Syndrome X.

The phenotypic tests in this instance included the measurement of serum cholesterol and triglycerides.

Blood Lipids

Procedure:

A cohort of 4 wild type and 8 homozygote males were used in these assays. Mean serum cholesterol and triglyceride levels were measured and compared with gender matched (+/+) littermates. Concurrent testing of glucose tolerance was performed since this test is the standard for defining impaired glucose homeostasis in mammals. The glucose tolerance test was performed using a Lifescan glucometer. Animals were injected IP at 2 g/kg with D-glucose delivered as a 20% solution and blood glucose levels were measured at 0, 30, 60 and 90 minutes after injection. The COBAS Integra 400 (Roche) was used for running blood chemistry tests on mice.

Results:

The male and female homozygous mutant mice exhibited a notably decreased mean triglyceride level when compared with their gender-matched wild-type littermates and the historical means. These mutants also showed decreased mean serum cholesterol levels when compared with their wild-type littermates. Concurrently, male (−/−) mice exhibited an enhanced glucose tolerance in the presence of normal fasting glucose at all 3 intervals tested when compared with their gender-matched (+/+) littermates and the historical means, whereas, female (−/−) mice showed a decreased mean serum glucose level. In summary, these knockout mice exhibited a positive phenotype with regards to lipid and/or glucose metabolism. Thus, mutant mice deficient in the ANGPTL4 gene can serve as a model for treatment of cardiovascular disease. Antagonists of ANGPTL4 or its encoding gene would play an important role in regulating blood lipids and in particular in maintaining normal cholesterol and triglyceride metabolism. Such inhibitors or antagonists of ANGPTL4 would be useful in the treatment of such cardiovascular diseases associated with dyslipidemia as: hypertension, atherosclerosis, heart failure, stroke, various coronary artery diseases, obesity, and/or diabetes.

Immunology Phenotypic Analysis:

Immune related and inflammatory diseases are the manifestations or consequences of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or a combination of these.

Though the genesis of these diseases often involved multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host animal. T cells include helper T cells and cytotoxic T cells. Helper T cells proliferate extensively following recognition of an antigen-MHC complex on an antigen presenting cell. Helper T cells also secrete a variety of cytokines, e.g., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. See, e.g., *Current Protocols in Immunology*, ed. John E. Coligan, 1994, John Wiley & Sons, Inc.

Many immune related diseases are known and have been extensively studied. Such diseases include immune-mediated inflammatory diseases (e.g., rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Serum Immunoglobulin Isotyping Assay:

The Serum Immunoglobulin Isotyping Assay was performed using a Cytometric Bead Array (CBA) kit. This assay was used to rapidly identify the heavy and light chains isotypes of a mouse monoclonal antibody in a single sample. The values expressed are "relative fluorescence units" and are based on the detection of kappa light chains. Any value <6 is not significant.

Results: The serum immunoglobulin isotyping assay revealed that mutant (−/−) mice exhibited an elevation of IgM serum immunoglobulins compared to their gender-matched (+/+) littermates. IgM immunoglobulins are the first to be produced in a humoral immune response for neutralization of bacterial toxins and are particularly important in activating the complement system. Likewise, IgG immunoglobulins have neutralization effects and to a lesser extent are important for activation for the complement system. In addition, the (−/−) mice exhibited an increased mean absolute neutrophil count when compared with their (+/+) littermates and the historical mean. The observed phenotype suggests that ANGPTL4 is a negative regulator of inflammatory responses. These immunological abnormalities suggest that inhibitors (antagonists) of ANGPTL4 may be important agents which could stimulate the immune system (such as T cell proliferation) and would find utility in the cases where this effect would be beneficial to the individual such as in the case of leukemia, and other types of cancer, and in immunocompromised patients, such as AIDS sufferers. Accordingly, ANGPTL4 or agonists thereof may play a role in inhibiting the immune response and would be useful candidates for suppressing harmful immune responses, e.g., in the case of graft rejection or graft-versus-host diseases.

Example 8

Preparation of Antibodies that Bind to Angptl4

Techniques for producing the polyclonal antibodies and monoclonal antibodies are known in the art and are described herein. Antigens (or immunogens) that may be employed include purified protein of the invention, protein fragments, fusion proteins containing such protein, and cells expressing recombinant protein and/or protein fragments on the cell surface. Selection of the antigen can be made by the skilled artisan without undue experimentation.

Mice, such as Balb/c, are immunized with the antigen emulsified in complete Freund's adjuvant and injected subcutaneously or intraperitoneally in an amount from 1-100 micrograms. Alternatively, the antigen is emulsified in MPL-TDM adjuvant (Ribi Immunochemical Research, Hamilton, Mont.) and injected into the animal's hind food pads. The immunized mice are then boosted 10 to 12 days later with additional antigen emulsified in the selected adjuvant. Thereafter, for several weeks, the mice might also be boosted with additional immunization injections. Serum samples may be periodically obtained from the mice by retro-orbital bleeding for testing ELISA assays to detect the antibodies.

After a suitable antibody titer has been detected, the animals "positive" for antibodies can be injected with a final intravenous injection of the given ligand. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the antigen. Determination of "positive" hybridoma cells secreting the desired monoclonal antibodies against ANGPTL4 herein is well within the skill in the art.

The positive hybridoma cells can be injected intraperitoneal into syngeneic Balb/c mice to produce ascites containing the anti-ANGPTL4 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

For example, polyclonal rabbit antibodies were generated by immunization of rabbit with 500 µg of recombinant human ANGPTL4 protein (23-406) generated in *E. Coli* on days 1, 40 and 70. Serum was harvested in day 80 and 120 post immunization and antibodies were purified by protein-A sephadex columns.

Example 9

Blocking or Neutralizing Antibodies

Antibodies against the antigens described herein, e.g., ANGPTL4, can be identified by a variety of techniques known in the art, e.g., an ELISA. For example, plates can be coated with the polypeptide of interest, e.g., ANGPTL4 or a fragment thereof, and incubated with antibodies generated against that polypeptide, e.g., ANGPTL4 (see, e.g., description in U.S. Pat. Nos. 6,348,350, 6,372,491 and 6,455,496). Bound antibody can be detected by various methods.

Antagonist (e.g., blocking or neutralizing) antibodies can be identified by competition assays and/or activity assays. For example, expression of ANGPTL4 stimulates cell hepatocyte or pre-adipocyte proliferation, adipocyte migration, regulates triglyceride amounts, or binds to $\alpha_v\beta_5$ integrin. Determination of a blocking or neutralizing antibody to ANGPTL4 can be shown by the ability of the antibody to block these activities, e.g., (see, e.g., FIG. 9, Panel B, D and E). For example, hepatocytes or pre-adipocytes cells can be plated and incubated with supernatant from COST cells transduced with Ad-hAngptl4 along with an anti-ANGPTL4 antibody, or a control antibody or PBS. After several days, the cells can be trypsinized and counted. Antibodies that reduce the numbers of cells are identified as blocking or neutralizing antibodies. ANGPTL4 was also shown to induce hepatocyte adhesion and pre-adipocyte migration, thus determination of a blocking or neutralizing antibody to ANGPTL4 can be shown by the ability of the antibody to block the hepatocyte adhesion and/or pre-adipocyte cell migration. ANGPTL4 was also shown to be a proangiogenic factor. See, e.g., Le Jan et al., *American Journal of Pathology*, 164(5): 1521-1528 (2003). Thus, blocking or neutralizing antibodies to ANGPTL4 can be identified by using the antibodies in combination with ANGPTL4 in angiogenesis assays, e.g., CAM assay.

The specification is considered to be sufficient to enable one skilled in the art to practice the invention. It is understood that the examples and embodiments described herein are for illustrative purposes only. The invention is not to be limited in scope by the construct deposited, since the deposited embodiment is intended as a single illustration of certain aspects of the invention and any constructs that are functionally equivalent are within the scope of the invention. The deposit of material herein does not constitute an admission that the written description is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

We claim:

1. A method of stimulating proliferation of pre-adipocytes in a human subject for the treatment of a wasting disease in said human subject, the method comprising: administering a composition comprising an effective amount of a mature ANGPTL4 to a population of pre-adipocytes in a human subject, thereby inducing the proliferation of pre-adipocytes in said human subject, wherein the amount of ANGPTL4 in the composition is sufficient to stimulate proliferation of the pre-adipocytes and treat a wasting disease in said subject.

2. The method of claim 1, wherein the composition comprises the ANGPTL4 with a carrier.

3. The method of claim 1, wherein the ANGPTL4 comprises the amino acid sequence shown as SEQ ID NO: 8.

4. The method of claim 1, wherein the ANGPTL4 comprises the amino acid sequence shown as SEQ ID NO: 29.

* * * * *